US005534533A

United States Patent [19]

Ohtani et al.

[11] Patent Number: 5,534,533

[45] Date of Patent: Jul. 9, 1996

[54] CARBOXYLATE DERIVATIVES EXHIBITING PHOSPHOLIPASE $A_2$ INHIBITORY ACTIVITY

[75] Inventors: Mitsuaki Ohtani, Nara; Toshiyuki Kato, Suita; Yozo Hori, Hirakata, all of Japan

[73] Assignee: Shionogi & Co., Ltd., Osaka, Japan

[21] Appl. No.: 313,890

[22] Filed: Sep. 28, 1994

[30] Foreign Application Priority Data

Oct. 1, 1993 [JP] Japan .................................... 5-246732
Jul. 6, 1994 [JP] Japan .................................... 6-154937

[51] Int. Cl.[6] ......................... A61K 31/40; C07D 209/48

[52] U.S. Cl. .......................... 514/372; 514/255; 514/329; 514/330; 514/417; 514/621; 544/382; 544/383; 544/391; 546/221; 546/223; 546/226; 546/237; 548/213; 548/473; 548/475; 548/476

[58] Field of Search .................................... 514/621, 255, 514/329, 330, 372, 417; 564/169; 544/382, 383, 391; 546/221, 223, 226, 237; 548/213, 473, 475, 476

[56] References Cited

U.S. PATENT DOCUMENTS 4,067,892 1/1978 Thorne et al. ........................... 560/9 X

FOREIGN PATENT DOCUMENTS 0547231 6/1993 European Pat. Off. .
2241296 3/1975 France .

*Primary Examiner*—Jacqueline Haley
*Attorney, Agent, or Firm*—Wenderoth, Lind & Ponack

[57] ABSTRACT

Novel carboxylate derivatives exhibiting phospholipase $A_2$ inhibitory activity are disclosed. Specifically, the following compounds of the formula and pharmaceutically acceptable salts thereof are disclosed:

(I)

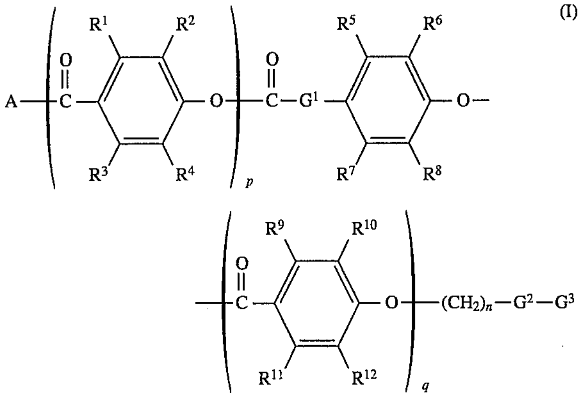

wherein A is hydroxy, amino, or lower alkylamino; $R^1$ to $R^{12}$ are independently hydrogen, methyl, methoxy, or hydroxy, provided that all of $R^1$ to $R^{12}$ are not hydrogen; $G^1$ is a single bond, or a group of $-(CH_2)_xO(CH_2)_y-$ wherein x and y are independently 0–5; $G^2$ is a single bond, oxygen, sulfur, carbonyl, etc.; $G^3$ is alkyl, aryl, or a group of the formula:

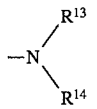

wherein $R^{13}$ and $R^{14}$ are independently hydrogen, alkyl, aryl, etc.; or $R^{13}$ and $R^{14}$ may be taken together with the adjacent nitrogen atom to form a heterocyclic group or a group of the formula:

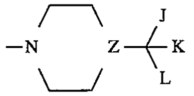

wherein Z is a carbon atom or a nitrogen atom,

J, K, and L are independently hydrogen or aryl, etc.; p and q are independently 0, 1, or 2; and n is an integer of 1 to 8.

8 Claims, No Drawings

CARBOXYLATE DERIVATIVES EXHIBITING PHOSPHOLIPASE $A_2$ INHIBITORY ACTIVITY

The present invention relates to novel phospholipase $A_2$ inhibitors. More particularly, this invention is directed to carboxylic acid derivatives consisting of aromatic rings straight-chained structure and having phospholipase $A_2$ inhibitory activity.

Phospholipase $A_2$ is an enzyme which exists in cells and secretory liquid of many animals, in particular, venom of snakes, mammalian pancreas, blood platelet of various animals, arthritis exudate of higher animals or the like. This enzyme specifically hydrolyzes phospholipids. For example, the enzyme specifically hydrolyzes C-2 positioned fatty acid esters of 1, 2-diacylglycerol phospholipid to form lysoglycerol phospholipids and fatty acids. It has been pointed out that, in association with this enzymatic activity, phospholipase $A_2$ can show toxicity to vascular nerve, muscle, arthrosis, heart, lung, trachea or the like, induce convulsion, vasoconstriction, tracheal constriction, edema or the like, and cause arthritis, sepsis, asthma, respiratory insufficiency or the like.

If the enzymatic activity of phospholipase $A_2$ could be inhibited various diseases caused by or associated with said activity would be treated. From such a point of view, the present applicant has disclosed natural thielocin, a phospholipase $A_2$ inhibitor in Japanese Patent Publication (Kokai) No. 286088/1990, Japanese Patent Publication (Kokai) No. 117346/1992, etc. and synthetic thielocin homologs in WO 93/01157.

It has recently been found that phospholipase $A_2$ includes intracellular $PLA_2$ ($cPLA_2$) and secretory $PLA_2$ ($sPLA_2$) which can be clearly discriminated. It is well known that intracellular $PLA_2$ more preferentially hydrolyzes phospholipids containing arachidonate ester in the 2 position than the secretory $PLA_2$. However, there is no report on the inhibitory activity of the $cPLA_2$.

Paying attention to the structure of natural thielocin derivatives which can inhibit phospholipase $A_2$ activity, the present inventors have found novel compounds which inhibit both $cPLA_2$ and $sPLA_2$ by chemical modification of said natural thielocin. The compounds of the present invention can be expected to reduce the action of a substance inducing inflammation by suppressing the isolation of arachidonic acid from phospholipid and inhibiting thereby the production of various prostaglandins and leukotrienes called arachidonate cascade.

The present invention relates to a compound represented by the formula:

(I)

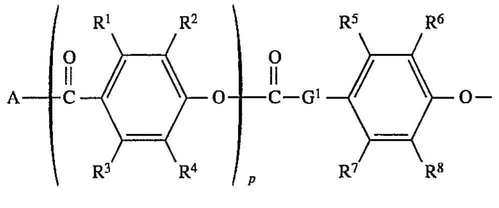

-continued

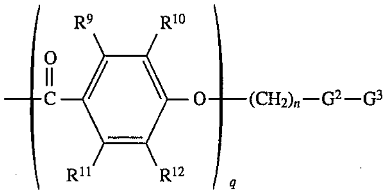

wherein A is hydroxy, amino, or lower alkylamino;

$R^1$ to $R^{12}$ are independently hydrogen, methyl, methoxy, or hydroxy, provided that all of $R^1$ to $R^{12}$ are not hydrogen;

$G^1$ is a single bond, or a group of $-(CH_2)_xO(CH_2)_y-$ wherein x and y are independently an integer of from 0 to 5;

$G^2$ is a single bond, oxygen, sulfur, carbonyl, sulfinyl, or sulfonyl;

$G^3$ is alkyl, alkenyl, aryl, arylalkyl, arylalkenyl, bicyclo [3.1.1 ]heptenyl, bicyclo[2,2,1 ]heptyl, bornyl, chromanyl, or a group of the formula:

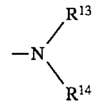

wherein $R^{13}$ and $R^{14}$ are independently hydrogen, alkyl, aryl,$-SO_2-$B in which B is aryl or alkyl, $-CO-$D in which D is aryl or alkoxy, or $-CH_2-$E in which E is aryl or a heterocyclic group; or $R^{13}$ and R14 may be taken together with the adjacent nitrogen atom to form a heterocyclic group or a group of the formula:

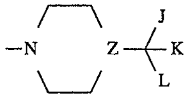

wherein Z is a carbon atom or a nitrogen atom, J, K, and L are independently hydrogen or aryl, provided that when Z is a carbon atom, one of J, K, or L may be combined with Z to form a double bond;

p and q are independently 0, 1, or 2; and n is an integer of 1 to 8; or a pharmaceutically acceptable salt thereof.

The preferable compounds of the present invention are the compounds of the formula (I) wherein $G^1$ is a single bond, p is 0 and q is 1. The more preferable compounds of the present invention are the compounds of the formula (I) wherein A is amino group or hydroxy group. The most preferable compounds of the present invention are the compounds of the formula (I) wherein $G^2$ is oxygen atom and $G^3$ is phenyl optionally substituted, particularly, the compound 102 of Example 47 as explained below.

In the present specification and claims, each group especially denotes the following groups.

The "alkyl" means a straight or branched $C_1$–$C_{10}$ alkyl and includes illustratively methyl, ethyl, propyl, n-butyl, i-butyl, t-butyl, n-pentyl, n-hexyl, i-hexyl, n-heptyl, t-heptyl, i-heptyl, n-octyl, i-octyl, 3,7-dimethyloctyl, n-nonyl, n-decyl, and the like, and preferably methyl. Said alkyl group may optionally have one or more substituents selected from a halogen atom, an alkoxy group and phenyl group.

The "lower alkyl" moiety in the "lower alkylamino" means a straight or branched $C_1$–$C_6$ alkyl and includes illustratively methyl, ethyl, propyl, n-butyl, i-butyl, t-butyl, n-pentyl, n-hexyl, and the like, and the "lower alkyl amino" includes, for example, methylamino, ethylamino, dimethylamino, diethylamino, ethylmethylamino, and the like.

The "alkoxy" means a straight or branched $C_1$–$C_6$ alkyloxy and includes illustratively methoxy, ethoxy, propoxy, t-butoxy, and the like, preferably methoxy.

The "halogen" illustratively includes fluoro, chloro, bromo, iodo, and the like.

The "aryl" includes, for example, phenyl, naphthyl, and the like, and preferably phenyl group. Said aryl group may optionally have one or more substituents selected from halogen atom, an alkyl group, an alkoxy group, trifluoromethyl group, an alkylenedioxy group, an acyl group, carboxyl group, an alkoxycarbonyl group, carbamoyl group, hydroxymethyl group, nitrile group and benzhydryl group. The preferable substituent may be carboxy group, carbamoyl group, a halogen atom, methyl, methoxy and trifluoromethyl. Thus, the preferable aryl may be, for example, 2-fluorophenyl, 3-fluorophenyl, 4-fluorophenyl, 2,3-difluorophenyl, 2,6-difluorophenyl, 4-chlorophenyl, 2,4-dichlorophenyl, 4-bromophenyl, 2,4-dibromophenyl, 4-methylphenyl, 4-ethylphenyl, 3,5-di-t-butylphenyl, 2 -methoxyphenyl, 3-methoxyphenyl, 4-methoxyphenyl, 2,3-dimethoxyphenyl, 2,6-dimethoxyphenyl, 2,4-dimethoxyphenyl, 3,4-dimethoxyphenyl, 3,5-dimethoxyphenyl, 3,4-methylenedioxyphenyl, 3,4-ethylenedioxyphenyl, 2-acetylenephenyl, 3-acetylphenyl, 4-acetylphenyl, 2-carboxyphenyl, 3-carboxyphenyl, 4-carboxyphenyl, 2 -methoxycarbonylphenyl, 3-methoxycarbonylphenyl, 4-methoxycarbonylphenyl, 2-ethoxycarbonylphenyl, 3-ethoxycarbonylphenyl, 4-ethoxycarbonylphenyl, 2-carbamoylphenyl, 3-carbamoylphenyl, 4-carbamoylphenyl, 6-benzhydrylphenyl, 4-trifluoromethylphenyl, and the like.

The "arylalkyl" means the above mentioned alkyl group substituted by the above mentioned aryl group, for example, benzyl, phenethyl, and the like. Both the "aryl" moiety and "alkyl" moiety in said arylalkyl group may have one or more substituents as mentioned above.

The "alkenyl" means a straight or branched $C_2$–$C_8$ alkenyl and includes illustratively vinyl, allyl, propenyl and the like. Said alkenyl may optionally have one or more substituents selected from a halogen atom, an alkoxy group and phenyl group. Said phenyl may still have any substituent selected from a halogen atom, an alkoxy group, an alkylenedioxy group, and the like.

The "arylalkenyl" means the above mentioned alkenyl group substituted by the above mentioned aryl group, for example, phenylvinyl, diphenylvinyl, phenylallyl, phenylpropenyl, and the like. Both the "aryl" moiety and "alkenyl" moiety in said arylalkenyl group may have one or more substituents as mentioned above.

The "alkylenedioxy" means, for example, methylenedioxy, ethylenedioxy, and the like.

The "acyl" means, for example, formyl, acetyl, propionyl, and the like.

The "alkoxy" moiety in the "alkoxycarbonyl" is the same as the above mentioned alkoxy group.

The pharmaceutically acceptable salt of the present invention means, for example, salts with an alkali metal such as sodium, potassium, or salts with an alkaline earth metal such as calcium.

The "heterocyclic group" means a cyclic group which has one or more heteroatoms selected from oxygen atom, sulfur atom and nitrogen atom in the cycle moiety, and which may be condensed with a carbocyclic group, and includes, for example, pyrrolyl, indolyl, isoindolyl, pyrazolyl, carbazolyl, benzimidazolyl, phenoxatinyl, phenoxazinyl, benzisoxazolyl, benzothiazolyl, benzoxazolyl, phthalimidoyl, o-benzoic sulfimidoyl and the like, and preferably phthalimidoyl or o-benzoic sulfimidoyl.

The compounds of the present invention also include the compounds of the formula (I) wherein the moiety of the formula: $-(CH_2)_n-G^2-G^3$ is the following groups of the formulae:

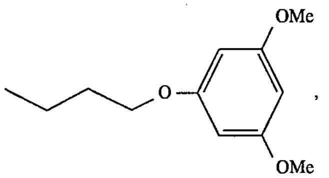

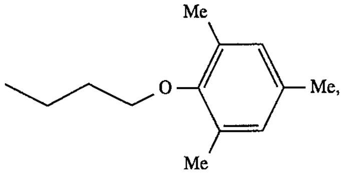

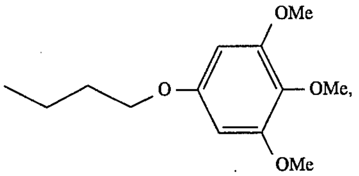

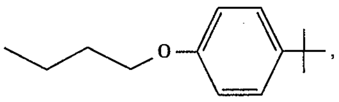

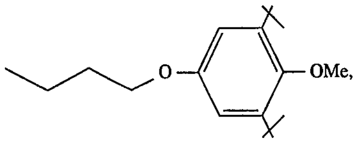

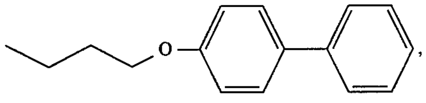

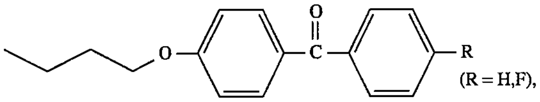

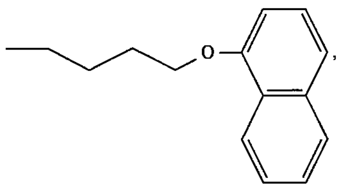

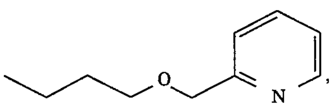

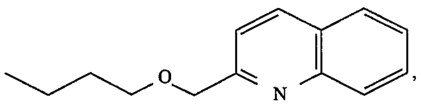

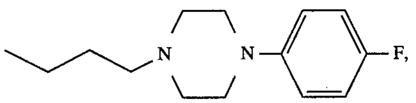

-continued
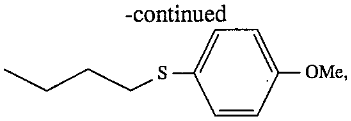
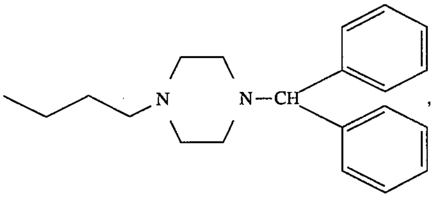
,
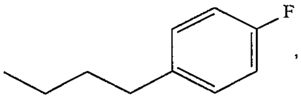
,
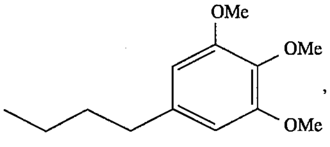
,
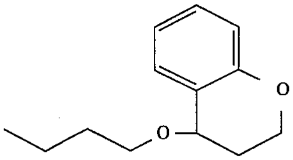
,
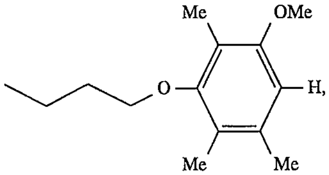
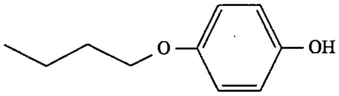
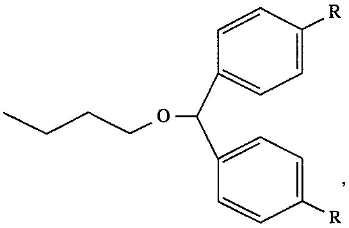
,
(R = H,F)
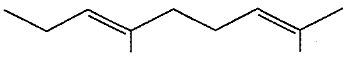
,
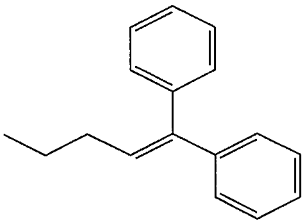
,
-continued
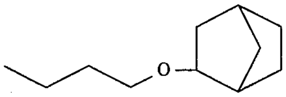
,
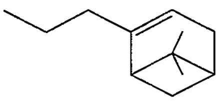
,
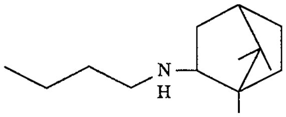
,
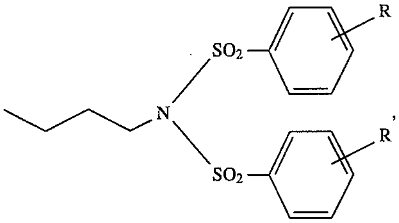
, (R = H,F)
Further, the compounds of the present invention include the compounds of the formula:

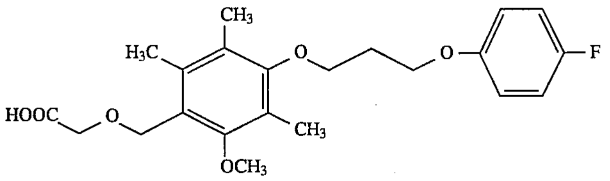

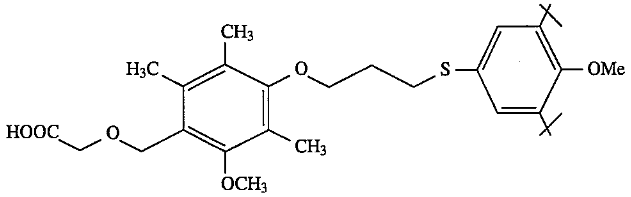

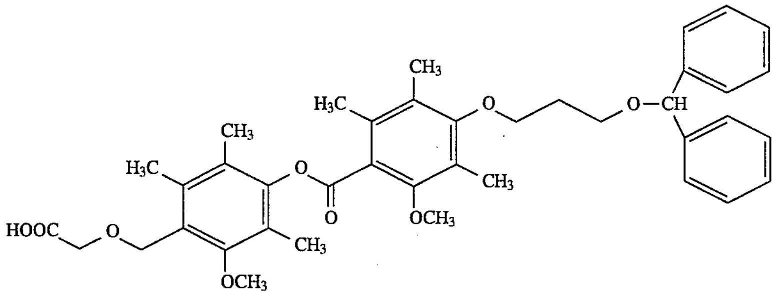

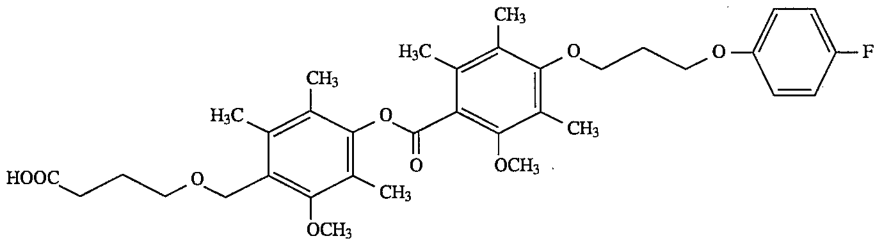

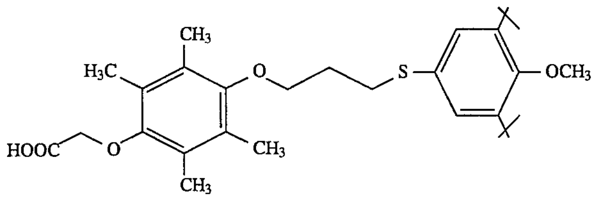

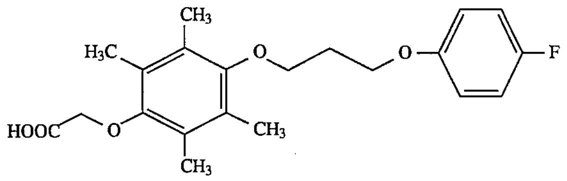

The compounds of the present invention may be prepared by a conventional method.

As shown in the following reaction scheme, the general synthesis of the compounds of the present invention is based on the synthesis of the ethers A which are prepared by the coupling reaction of the phenolic hydroxy group of the aromatic compounds represented by the formula B with the halogen compounds represented by the formula C or those having the same reactivity. Amides are prepared by amidation of the ethers A according to a conventional method.

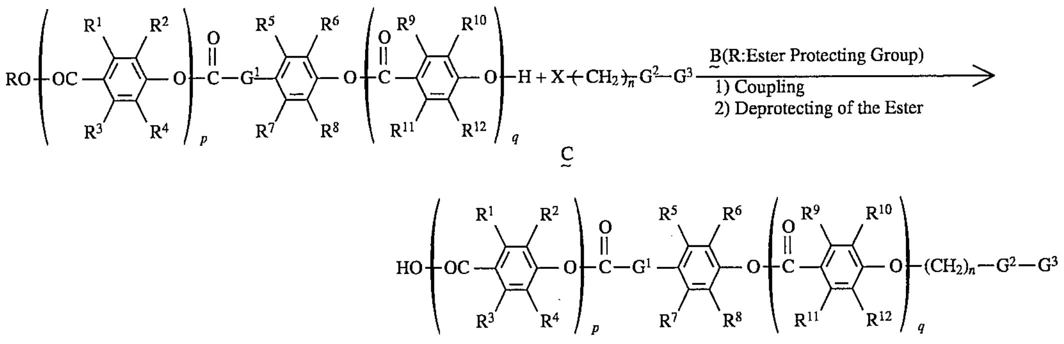

A wherein $R^1$ to $R^{12}$, $G^1$, $G^2$, $G^3$, p, q and n are as defined above.

Synthesis of Compound A of the Present Invention

1) Coupling:

The ether formation reaction by coupling of the phenol derivative B with compound C is effected under anhydrous conditions in the presence of a base such as sodium hydroxide, potassium hydroxide, sodium carbonate, potassium carbonate, sodium hydride, potassium hydride, n-butyllithium or the like, at 0°–200° C., preferably 60°–120° C. in a solvent such as tetrahydrofuran (THF), dimethyl sulfoxide (DMSO), N, N-dimethylformamide (DMF), N, N-dimethylacetamide (DMA) or the like. Compound C is a compound which can usually form an ether with a phenol and illustratively includes halogen compounds (X=Halogens), sulfonates ($X{=}OSO_2CH_3$, $OSO_2C_6H_5$, $OSO_2C_6H_4CH_3$, $OSO_2CF_3$) and the like.

2) Deprotection of the Ester:

Deprotection of the ester can be effected by hydrolysis with an acid or alkali or by hydrogenation with catalytic reduction. One of these methods may be selected, depending upon the character of the ester protecting group R. The acid includes hydrochloric acid, sulfuric acid, trifluoroacetic acid and the like, and the alkali includes sodium hydroxide, potassium hydroxide and the like. The hydrogenation for deprotection is effected under 1–20 atm of hydrogen atmosphere using a catalyst such as palladium, platinum, rhodium or the like at 0°–40° C. in a solvent such as methanol, ethanol, dioxane, acetic acid, water or mixture thereof.

Synthesis of Intermediate B

Many of the thielocin derivatives and thielavin derivatives obtained from a culture broth of *Thielavia terricola* (RF-143), a kind of fungus, have fundamentally a structure of the formula B or its free acid, and those natural compounds can be chemically modified into the compounds of the formula B. These compounds can be prepared by chemical synthesis, and the present inventors have disclosed the synthesis and synthetic methods of many compounds (WO 93/01157).

In case that $G^1$ is $-(CH_2)_x\,0\,(CH_2)_y-$ in which x and y are independently an integer from 0–5, compound B can be prepared from a hydroquinone derivative. The phenol derivative B has usually a popular ester-protecting group R, but it can be removed by deprotection by hydrolysis with a usually used acid or alkali after coupling reaction with compound C, as shown in the reaction scheme above.

Number of the benzene ring of compound B is 1–3 (p, q=0, 1, 2), and most of the synthesis of these phenols and esters B have been disclosed in detail in the Japanese Patent publications as described above.

Synthesis of Intermediate C

Compound C is prepared from methylene derivative D and derivative $G^3$—Z.

$$X-(CH_2)_n-Y + G^3-Z \longrightarrow X-(CH_2)_n-G^2-G^3$$

D C or $$X-(CH_2)_n-Y + G^3-Z \longrightarrow Y-(CH_2)_n-G^2-G^3$$

D E

In the formula above, $G^2$, $G^3$ and n have the same meanings as above.

Y in the above formula includes halogens and sulfonates similarly to X, and additionally includes a group changeable into X in the subsequent steps. In the latter case, the reaction for producing compound C advances via Intermediate E and finally Y is replaced by X. Illustrative examples of such Y is hydroxy group and an appropriately protected hydroxy group including tetrahydropyranyl (THP) ether, which is usually used.

Z in the derivative $G^3$—Z is defined as a nucleophilic reagent such as alcohols, thiols, and amines, and is combined with $G^3$ to form a substituted phenol, substituted thiophenol, substituted aniline, substituted piperazine and the like. The reaction from compound D to compound C can be effected substantially according to the same manner as in the synthetic method producing compound A with compound B and compound C. Particularly, the coupling is effected in a solvent such as DMF, THF or the like in the presence of a base such as sodium hydride, triethylamine or the like. Thus obtained compound C contains a new functional group $G^2$.

Compound C may be produced as above, but some of compound C include commercially available products such as 4'-bromo-4-chlorobutyrophenone.

The pharmaceutical compositions of the present invention can be applied via oral route and via parenteral route such as intravenous, percutaneous route or the like, and the compounds of the present invention may be formulated into peroral formulations, injections, ointments or the like.

Appropriate dose of the compounds of the present invention varies depending upon the desired therapeutic effect, route of the administration, age and body weight of patients, seriousness of the disease and usually is 1 mg to 1000 mg per day. In general, the daily dose is administered once or in two or three divisions. Accordingly, the pharmaceutical compositions of the present invention can be formulated into a unit dosage form containing its divisional dose of the compound of the present invention.

The following detailed examples and preparations are presented by way of illustration of certain specific embodiments of the invention. The examples and preparations are representative only and should not be construed as limiting the invention in any respect.

In the following examples and preparations, "TLC" means thin layer chromatography.

Preparation 1

Synthesis of Compound 2:

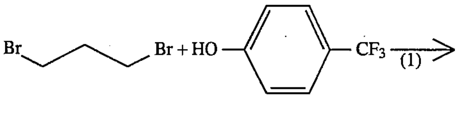

63 64

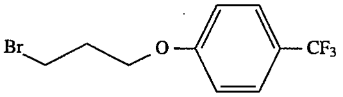

2

To a solution of p-trifluoromethylphenol 64 (2.0 g, 12.3 mmol) in dimethylformamide (15 ml) was added sodium hydride (60% oil suspension) (543 mg, 12.3 mmol×1.1), and the resultant mixture was stirred at room temperature for 1 hour. This was slowly added dropwise to a solution of 1, 3-dibromopropane 63 (12.5 ml, 12.3 mmol×10) in dimethylformamide (30 ml). The reaction mixture was stirred at 80° C. for 3 hours, chilled and partitioned into ethyl acetate and water. The organic layer was washed with water three times and once with saturated brine, dried and concentrated. The residue was heated at 40° C. to 100° C. under reduced pressure to remove excess of the dibromopropane. The residue was purified by chromatography on a column of silica gel [$SiO_2$ 8 g, developed with hexane-ethyl acetate (1:0)–(19:1)] to give oily product 2. The product was dried in vacuo and crystallized to give compound 2 as colorless crystals (1.64 g, yield 47%).

Melting point 26°–29° C.

$^1$HNMR ($CDCl_3$):δ2.35 (quin, J=6.0 Hz, 2H), 3.62 (t, J=6.2 Hz, 2H), 4.16 (t, J=6.0 Hz, 2H), 6.97 (d, J=8.4 Hz, 2H), 7.55 (d, J=8.4 Hz, 2H)

IR (Nujol): 1617, 1593, 1520, 1470, 1393, 1252, 1214, 1162, 1118, 1170, 1158, 1122, 1110, 920, 837, 637, 624 $cm^{-1}$ Preparation 2

Synthesis of Compound 5:

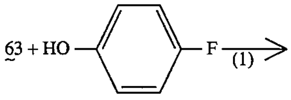

65

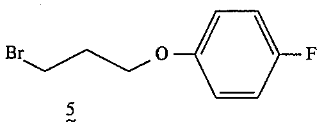

5

1, 3-Dibromopropane 63 and p-fluorophenol 65 were treated in the same manner as in Preparation 1, and the crude product obtained was purified by chromatography on a column of silica gel [$SiO_2$, developed with hexane-ethyl acetate (1:0)–(19:1 )] to give compound 5. as an oil (yield 41%).

$^1$H NMR ($CDCl_3$): δ2.31 (quin, J=6.2 Hz, 2H), 3.61 (t, J=6.2 Hz, 2H), 4.07 (t, J=5.9 Hz, 2H), 6.78–7.06 (m, 4H)

TLC Rf=0.5 (ethyl acetate:hexane=1:9)

Preparation 3

Synthesis of Compound 8:

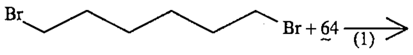

66

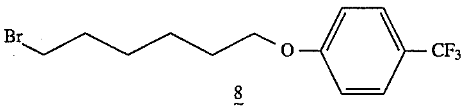

8

1, 6-Dibromohexane 66 and p-trifluoromethylphenol 64 were treated in the same manner as in Preparation 1, and the crude product obtained was purified by chromatography on a column of silica gel [$SiO_2$, developed with hexane-ethyl acetate (1:0)–(97:3)] to give compound 8 as an oil (yield 4.5%).

$^1$H NMR ($CDCl_3$): δ1.46–1.65 (m, 4H), 1.74–1.98 (m, 4H), 3.43 (t, J=7.7 Hz, 2H), 4.00 (t, J=6.3 Hz, 2H), 6.94 (d, J=9.2 Hz, 2H), 7.53 (d, J=9.2 Hz, 2H)

TLC Rf =0.65 (ethyl acetate:hexane=1:9)

Preparation 4

Synthesis of Compound 11:

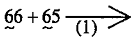

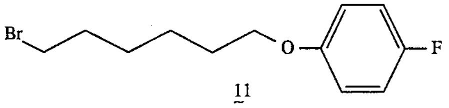

11

1, 6-Dibromohexane 66 and p-fluorophenol 65 were treated in the same manner as in Preparation 1 and the crude product obtained was purified by chromatography on a column of silica gel [Lober B manufactured by Merck, developed with hexane-ethyl acetate (1:0)–(9:1)] to give compound 11 as an oil (yield 20%).

$^1$H NMR ($CDCl_3$): δ1.43–1.61 (m, 4H), 1.70–1.87 (m, 4H), 3.43 (t, J=6.9 Hz, 2H), 3.92 (t, J=6.4 Hz, 2H), 6.76–7.02 (m, 4H)

TLC RF=0.5 (ethyl acetate:hexane=1:9)

Preparation 5

Synthesis of Compound 14:

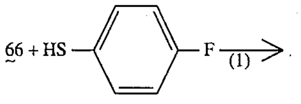

67

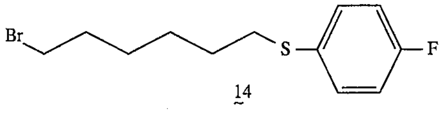

14

To a solution of p-fluorothiophenol 67 (2.13 ml, 20.0 mmol) in 1, 6-dibromohexane 66 (15.3 ml, 20.0 mmol×5) was added triethylamine (2.79 ml, 20.0 mmol), and the resultant mixture was stirred for 1 hour. The reaction mixture was dissolved in methylene chloride, and the solution was washed with 1N hydrochloric acid and water sequentially, dried, and concentrated. The residue was heated at 40° C.–130° C. in vacuo to remove excess of the dibromohexane. The resultant residue was purified by chromatography on a column of silica gel [$SiO_2$ 50 g, developed with hexane-ethyl acetate (1:0)–(9:1)] to give compound 14 (1.6 g) as an oil. (yield 27%)

$^1$H NMR ($CDCl_3$):δ1.38–1.70 (m, 6H), 1.77–1.93 (m, 2H), 2.87 (t, J=7.0 Hz, 2H), 3.40 (t, J=6.6 Hz, 2H), 6.92–7.06 (m, 2H), 7.26–7.39 (m, 2H)

TLC Rf=0.35 (ethyl acetate:hexane=1.19)

Preparation 6

Synthesis of Compound 17:

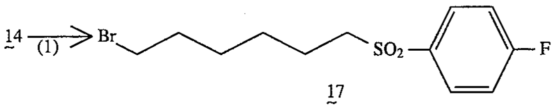

17

To a solution of compound 14 (582 mg, 2.0 mmol) in methylene chloride (10 ml) was added m-chloroperbenzoic acid (828 mg, 2.0 mmol×1.2) at room temperature. The mixture was stirred for 10 minutes and filtered to remove the insoluble material. The filtrate was concentrated and partitioned into ethyl acetate and aqueous sodium thiosulfate solution. The organic layer was washed with water, 5% aqueous sodium hydrogencarbonate solution and water sequentially, dried and concentrated to give compound 17 (660 mg) as an oil (yield 100%).

$^1$H NMR ($CDCl_3$): δ1.34–1.55 (m, 4H), 1.64–1.92 (m, 4H), 3.02–3.17 (m, 2H), 3.38 (t, J=6.7 Hz, 2H), 7.19–7.34 (m, 2H), 7.86–7.99 (m, 2H)

TLC Rf=0.1 (ethyl acetate:hexane=1:9)

Preparation 7

Synthesis of Comound 2.0:

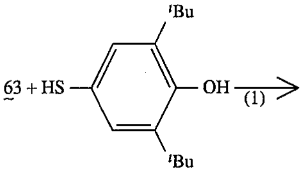

68

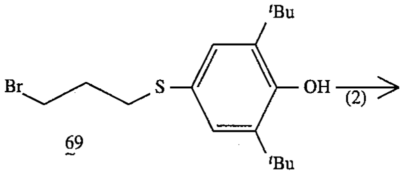

69

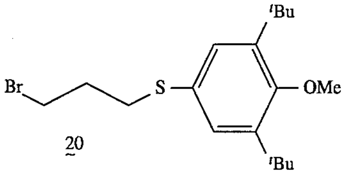

20

(1) 1, 3-Dibromopropane 63 and the known compound 68 were treated in the same manner as in Preparation 5 (1) to give crude product 69. This product was subjected to the next reaction.

TLC Rf=0.45 (ethyl acetate:hexane=1:19)

(2) To a solution of the crude product 69 in acetone were added anhydrous potassium carbonate (10 equivalents) and dimethyl sulfate (5 equivalents), and the mixture was slightly refluxed for 2 hours. The reaction mixture was filtered to remove the inorganic material. The filtrate was concentrated and the residue was partitioned into hexane and 1N hydrochloric acid. The organic layer was washed with water, dried and concentrated. The residue was purified by chromatography on a column of silica gel [$SiO_2$, developed with hexane] to give compound 20 as an oil (yield 31%).

$^1$H NMR ($CDCl_3$): δ1.42 (s, 18H), 2.14 (quin, J=6.7 Hz, 2H), 3.02 (t, J=6.8 Hz, 2H), 3.54 (t, J=6.5 Hz, 2H), 3.68 (s, 3H), 7.26 (s, 2H)

TLC Rf=0.8 (ethyl acetate:hexane=1:19)

Preparation 8

Synthesis of Comound 29:

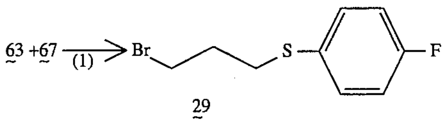

29

(1) 1, 3-Dibromopropane 63 and p-fluorothiophenol 67 were treated in the same manner as in Preparation 5, and the crude product obtained was purified by chromatography on a column of silica gel [$SiO_2$, developed with hexane] to give compound 29 as an oil (yield 70%).

$^1$H NMR ($CDCl_3$): δ2.11 (quin, J=6.6 Hz, 2H), 3.02 (t, J=6.8 Hz, 2H), 3.52 (t, J=6.4 Hz, 2H), 6.92–7.07 (m, 2H), 7.30–7.43 (m, 2H)

TLC Rf=0.3 (hexane)

Preparation 9

Synthesis of Comound 32:

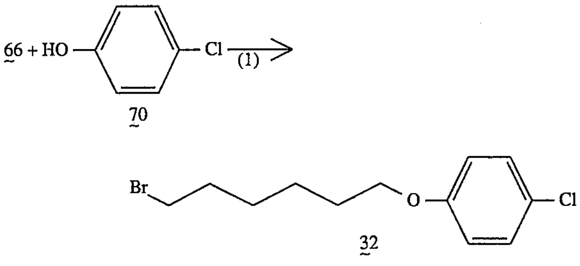

70

32

(1) 1, 6-Dibromohexane 66 and p-chlorophenol 70 were treated in the same manner as in Preparation 1, and the crude product obtained was purified by chromatography on a column of silica gel [$SiO_2$, developed with hexane-ethyl acetate (1:0)–(99:1)] to give compound 32 as colorless crystals (yield 57%).

Melting point 25°–27° C.

$^1$H NMR ($CDCl_3$): δ1.44–1.62 (m, 4H), 1.72–1.98 (m, 4H), 3.43 (t, J=7.7 Hz, 2H), 3.93 (t, J=6.3 Hz, 2H), 6.75–6.88 (m, 2H), 7.18–7.28 (m, 2H)

TLC Rf=0.2 (hexane)

Preparation 10

Synthesis of Comound 35:

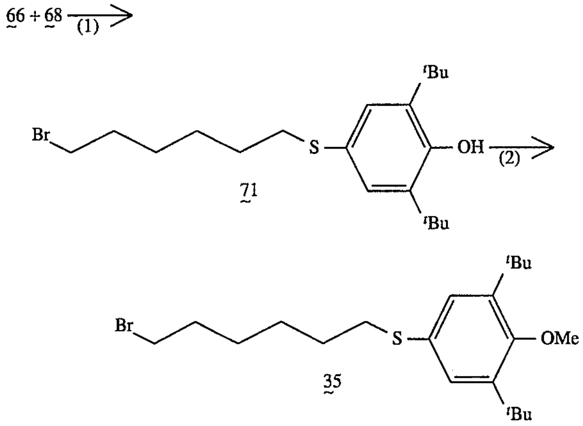

71

35

(1) 1, 6-Dibromohexane 66 and compound 68 were treated in the same manner as in Preparation 5 to give crude product 71. This product was subjected to the next reaction as it is.

TLC Rf=0.4 (ethyl acetate:hexane=1.9)

(2) To a solution of crude product 71 in dimethylformamide were added dimethyl sulfate (3 equivalents) and sodium hydride (1.5 equivalents) and the resultant mixture was stirred at room temperature for 1 hour. To the reaction mixture were poured a mixture of 1N hydrochloric acid and ether, and the resultant mixture was partitioned. The organic layer was washed with water and saturated brine sequentially, dried and concentrated. The residue was purified by chromatography on a column of silica gel [$SiO_2$, developed with hexane-ethyl acetate (1:0)–(999:1)] to give compound 35 as an oil. (yield 27%).

$^1$H NMR ($CDCl_3$): δ1.22–1.93 (m, 26H), 2.87 (t, J=6.2 Hz, 2H), 3.40 (t, J=6.7 Hz, 2H), 3.67 (s, 3H), 7.23 (s, 2H)

TLC Rf=0.6 (ethyl acetate; hexane=1:19)

Preparation 11

Synthesis of Comound 41:

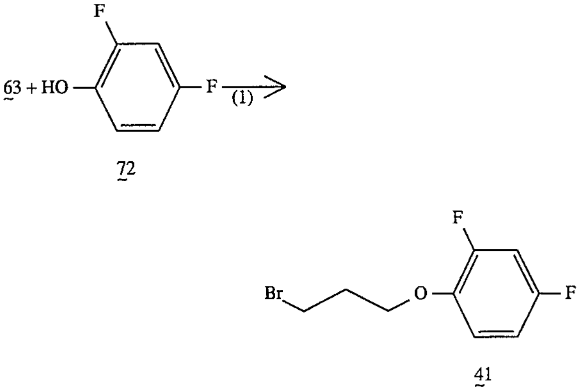

72

41

1, 3-Dibromopropane 63 and 2, 4-difluorophenol 72 were treated in the same manner as in Preparation 1, and the crude product obtained was purified by chromatography on a column of silica gel [$SiO_2$, developed with hexane-ethyl acetate =(1:0)–(19:1) to give compound 41 as an oil(yield 56%).

$^1$H NMR ($CDCl_3$): δ2.33 (quin, J=6.2 Hz, 2H), 3.63 (t, J=6.2 Hz, 2H), 4.14 (t, J=6.0 Hz, 2H), 6.73–7.02 (m, 3H)

TCL Rf=0.5 (ethyl acetate:hexane=1:4)

Preparation 12

Synthesis of Compound 48:

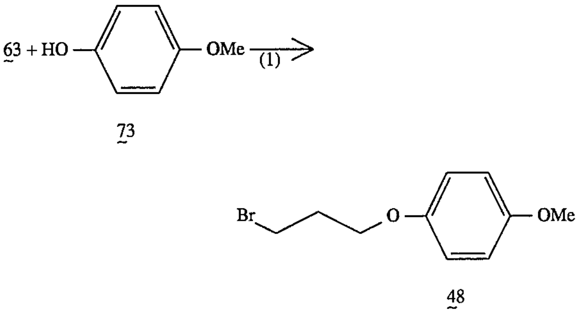

73

48

1, 3-Dibromopropane 63 and p-methoxyphenol 73 were treated in the same manner as in Preparation 1, and the crude product obtained was purified by chromatography on a column of silica gel [$SiO_2$, developed with hexane-ethyl acetate (1:0)–(19:1)] to give compound 48 as an oil (yield 69%).

$^1$H NMR ($CDCl_3$): δ2.29 (quin, J=6.1 Hz, 2H), 3.60 (t, J=6.5 Hz, 2H), 3.77 (s, 3H), 4.05 (t, J=5.8 Hz, 2H), 6.84 (s, 4H)

TCL Rf=0.55 (ethyl acetate:hexane=1:4)

Preparation 13

Synthesis of Comound 51:

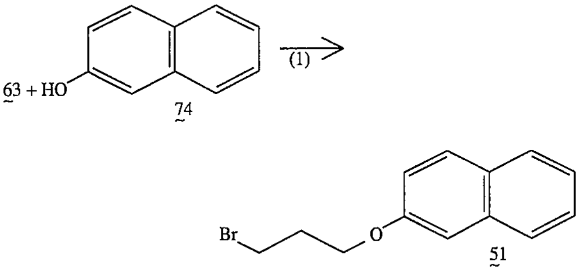

74

51

1, 3-Dibromopropane 63 and β-naphthol 74 were treated in the same manner as in Preparation 1, and the crude product obtained was purified by chromatography on a column of silica gel [$SiO_2$, developed with hexane] to give compound 51 as an oil (yield 70%).

$^1$H NMR ($CDCl_3$): δ2.39 (quin, J=6.1 Hz, 2H), 3.65 (t, J=6.5 Hz, 2H), 4.23 (t, J=6.0 Hz, 2H), 7.08–7.51 (m, 4H), 7.70–7.81 (m, 3H)

TCL Rf=0.6 (ethyl acetate:hexane=1:4)

Preparation 14

Synthesis of Comound 56:

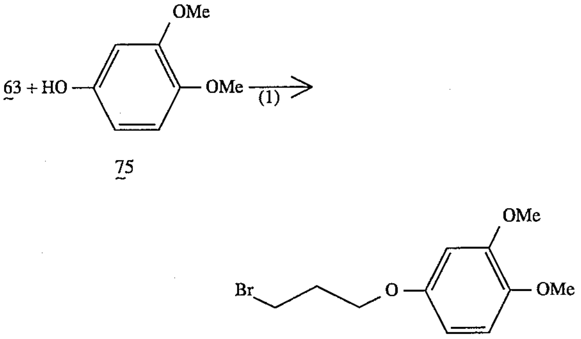

75

56

1, 3-Dibromopropane 63 and 3, 4-dimethoxyphenol 75 were treated in the same manner as in Preparation 1, and the crude product obtained was purified by chromatography on a column of silica gel [$SiO_2$, developed with hexane-ethyl acetate (1:0)–(9:1)] to give compound 56 as an oil (yield, 36%).

$^1$H NMR ($CDCl_3$): δ2.30 (quin, J=6.1 Hz, 2H), 3.61 (t, J=6.4 Hz, 2H), 3.84 (s, 3H), 3.86 (s, 3H), 4.06 (t, J=5.9 Hz, 2H), 6.41 (dd, J=8.6 Hz, 2.8 Hz, 1H), 6.52 (d, J=2.8 Hz, 1H), 6.78 (d, J=8.6 Hz, 1 H)

TCL Rf=0.15 (ethyl acetate:hexane=1:4)

Preparation 15

Synthesis of Comound 60:

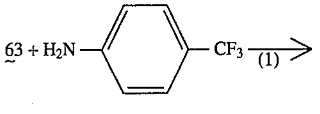

76

-continued

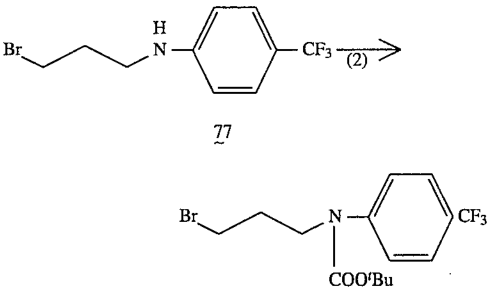

77

60

(1) 1, 3-Dibromopropane 63 and p-trifluoromethylaniline 76 were treated in the same manner as in Preparation 5, and the crude product obtained was purified by chromatography on a column of silica gel [Lober B manufactured by Merck, developed with hexane-ethyl acetate (1:0)–(9:1)] to give compound 77 as an oil (yield 52%).

$^1$H NMR ($CDCl_3$): δ2.16 (quin, J=6.4 Hz, 2H), 3.39 (t, J=6.6 Hz, 2H), 3.51 (t, J=6.2 Hz, 2H), 4.22 (brs, 1H), 6.63 (d, J=9.0 Hz, 2H), 7.41 (d, J=8.8 Hz, 2H)

TCL Rf=0.55 (ethyl acetate:hexane=1:4)

(2) To a solution of compound 77 in methanol was added di-tert-butyl dicarbonate (3 mol equivalents), and the mixture was allowed to react at 55° C. for 42 hours. The reaction mixture was partitioned into ethyl acetate and dilute hydrochloric acid. The organic layer was washed with water, 5% aqueous sodium hydrogencarbonate solution, water and saturated brine sequentially, dried and concentrated. The residue was purified by chromatography on a column of silica gel [$SiO_2$, developed with toluene] to give compound 60 as an oil(.yield 54%)

$^1$H NMR ($CDCl_3$): δ1.46 (s, 9H), 2.14 (quin, J=7.0 Hz, 2H), 3.39 (t, J=6.4 Hz, 2H), 3.83 (t, J=7.1 Hz, 2H), 7.34 (d, J=8.2 Hz, 2H), 7.60 (d, J=8.2 Hz, 2H).

TCL Rf=0.5 (ethyl acetate:hexane=1:9)

EXAMPLE 1

4-[4-[3-(4-Trifluoromethylphenoxy)propyloxy]-2-methoxy-3,5,6-trimethylphenylcarboxy]-2-methoxy-3,5,6-trimethylbenzoic acid (4)

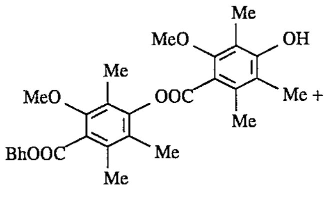

1

Bh = benzhydryl

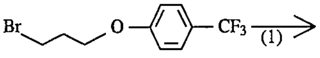

2

-continued

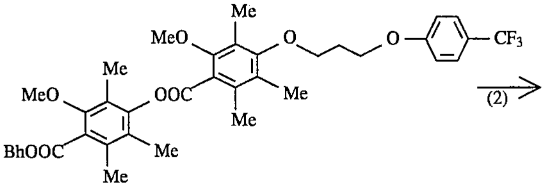

3

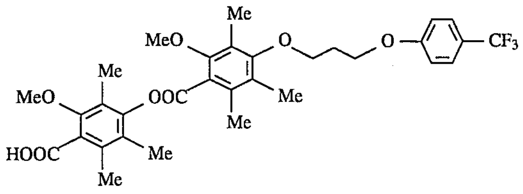

(1) To a solution of compound 1 (described in the specification of the International Publication WO93/01157) (3.70 g, 6.5 mmol) in dimethylformamide (100 ml) was added sodium hydride (60% oily suspension) (286 mg, 6.5 mmol×1.1) with ice cooling, and the mixture was stirred with ice cooling for 1 hour as it is. To this mixture was added compound 2 (2.02 g, 6.5 mmol×1.1) obtained in Preparation 1, and the mixture was stirred at 100° C. for 1 hour. After cooling, the reaction mixture was partitioned into ethyl acetate-2N and hydrochloric acid. The organic layer was washed with water three times and with saturated brine, dried and concentrated to give oily crud product. The oily crude product obtained was purified by chromatography on a column of silica gel [Lober B manufactured by Merck, developed with toluene] to give compound 3 (4.5 g) as an oil (yield 90%).

$^1$H NMR ($CDCl_3$): δ2.08 (s, 3H), 2.12–2.40 (m, 17H), 3.56 (s, 3H), 3.78 (s, 3H), 3.95 (t, J=6.1 Hz, 2H), 4.31 (t, J=6.1 Hz, 2H), 7.01 (d, J=8.6 Hz, 2H), 7.19 (s, 1H), 7.26–7.50 (m, 10H), 7.57 (d, J=8.6 Hz, 2H)

TCL Rf=0.65 (ethyl acetate:benzene =1:9)

(2) To a solution of compound 3 (4.5 g, 5.83 mmol)in methylene chloride (18 ml) were added anisole (3.2 ml, 5.83 mmol×5) and trifluoroacetic acid (13.5 ml, 5.83 mmol×30) sequentially under ice cooling, and the resultant mixture was stirred at room temperature for 1 hour. The reaction mixture was concentrated, and the residue was dissolved in methylene chloride and concentrated, followed by this procedure was repeated once more to remove excess of the trifluoroacetic acid. The residue was recrystallized from ether-hexane to give compound 4 (2.74 g) as colorless crystals. (yield 70%)

Melting point 76°–79° C. (decomposition)

$^1$H NMR ($CDCl_3$): δ2.15–2.40 (m, 20H), 3.80 (s, 3H), 3.85 (s, 3H), 3.96 (t, J=6.0 Hz, 2H), 4.32 (t, J=6.0 Hz, 2H), 7.01 (d, J=8.4 Hz, 2H), 7.57 (d, J=8.4 Hz, 2H)

IR (Nujol): 1733, 1614, 1577, 1520, 1329, 1262, 1160, 1100, 987, 844 cm$^{-1}$

Elementary Analysis (%) for $C_{32}H_{35}F_3O_8$

Calcd: C, 63.57; H, 5.84; F, 9.43

Found: C, 63.68; H, 6.06; F, 9.17

EXAMPLE 2

4-[4-[3-(4-Fluorophenoxy)propyloxy]-2-methoxy-3,5,6-trimethylphenylcarboxy]-2-methoxy-3,5,6-trimethylbenzoic acid (7)

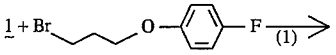

5

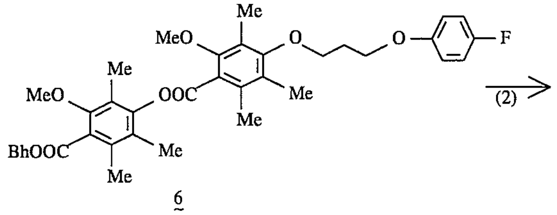

6

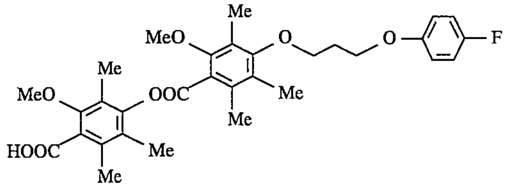

7

(1) Compound 1 was allowed to react with compound 5 which was obtained in Preparation 2, in the same manner as in Example 1 (1), and the crude product obtained was purified by chromatography on a column of silica gel [$SiO_2$, developed with hexane-ethyl acetate (9:1)] to give compound 6 as an oil (yield 100%).

$^1$H NMR ($CDCl_3$): δ2.08 (s, 3H), 2.15–2.39 (m, 17H), 3.56 (s, 3H), 3.78 (s, 3H), 3.94 (t, J=6.2 Hz, 2H), 4.22 (t, J=5.9 Hz, 2H), 6.83–7.03 (m, 4H), 7.19 (s, 1H), 7.28–7.50 (m, 10H)

TCL Rf=0.47 (ethyl acetate:hexane=1:2)

(2) Compound 6 was allowed to react in the same manner as in Example 1 (2) to give crude product 7. The crude product was recrystallized from methylene chloride-hexane to give compound 7 (yield 84%) as colorless crystals.

Melting point 134°–135° C.

$^1$H NMR ($CDCl_3$:CD3OD=9:1): δ2.16–2.40 (m, 20H), 3.80 (s, 3H), 3.82 (s, 3H), 3.96 (t, J=6.0 Hz, 2H), 4.23 (t, J=5.9 Hz, 2H), 6.85–7.07 (m, 4H)

IR (Nujol): 3440, 1722, 1575, 1507, 1206, 1164, 1095 cm$^{-1}$

Elementary Analysis (%) for $C_{31}H_{35}FO_8$•$0.2H_2O$

Calcd: C, 66.70; H, 6.39; F, 3.40

Found: C, 66.54; H, 6.35; F, 3.45

EXAMPLE 3

4-[4-[6-(4-Trifluoromethylphenoxy)hexyloxy]-2-methoxy-3,5,6-trimethylphenylcarboxy]-2-methoxy-3,5,6-trimethylbenzoic acid (10)

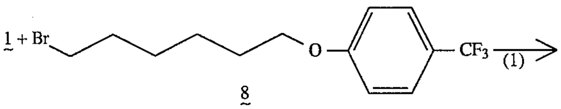

8

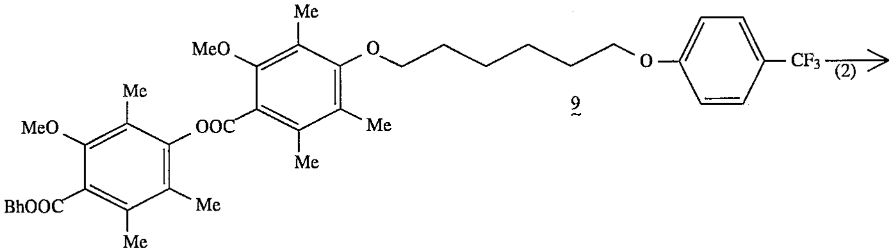

9

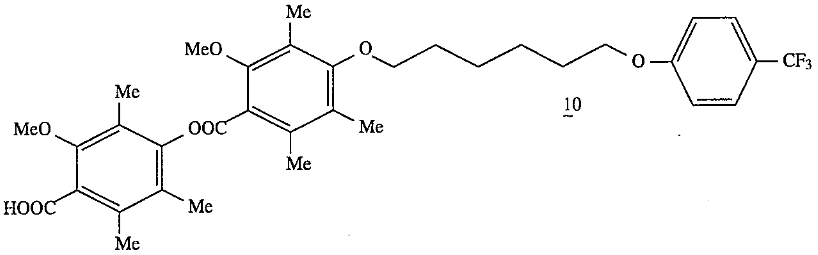

10

(1) Compound 1 was allowed to react with compound 8 obtained in Preparation 3, in the same manner as in Example 1 (1), and the crude product obtained was purified by chromatography on a column of silica gel [$SiO_2$, developed with hexane-ethyl acetate (9:1)-(4:1)] to give compound 9 as a foam (yield 92%).

$^1$H NMR ($CDCl_3$): δ1.51–1.70 (m, 4H), 1.80–1.97 (m, 4H), 2.08 (s, 3H), 2.17–2.29 (m, 12H), 2.34 (s, 3H), 3.56 (s, 3H), 3.70–3.83 (m, 5H), 4.03 (t, J=6.4 Hz, 2H), 6.90–7.01 (m, 2H), 7.19 (s, 1H), 7.27–7.60 (m, 12H)

TLC Rf=0.5 (ethyl acetate:hexane=1:2)

(2) Compound 9 was treated in the same manner as in Example 1 (2), and the crude product obtained was recrystallized from methylene chloride-hexane to give compound 10 as colorless crystals (yield 83%).

$^1$H NMR ($CDCl_3$): δ1.54–1.67 (m, 4H), 1.79–1.94 (m, 4H), 2.17–2.32 (m, 15H), 2.36 (s, 3H), 3.76 (t, J=6.5 Hz, 2H), 3.81 (s, 3H), 3.86 (s, 3H), 4.04 (t, J=6.3 Hz, 2H), 6.96 (d, J=8.4 Hz, 2H), 7.54 (d, J=8.4 Hz, 2H)

IR (Nujol): 1745, 1705, 1617, 1575, 1520, 1158 $cm^{-1}$

Elementary Analysis (%) for $C_{35}H_{41}F_3O_8$

Calcd: C, 65.00; H, 6.39; F, 8.81

Found: C, 64.77; H, 6.36; F, 8.77

EXAMPLE 4

4-[4-[6-(4-Fluorophenoxy)hexyloxy]-2-methoxy-3,5,6-trimethylphenylcarboxy]-2-methoxy-3,5,6-trimethylbenzoic acid (13)

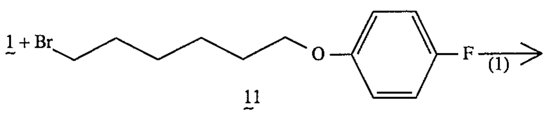

11

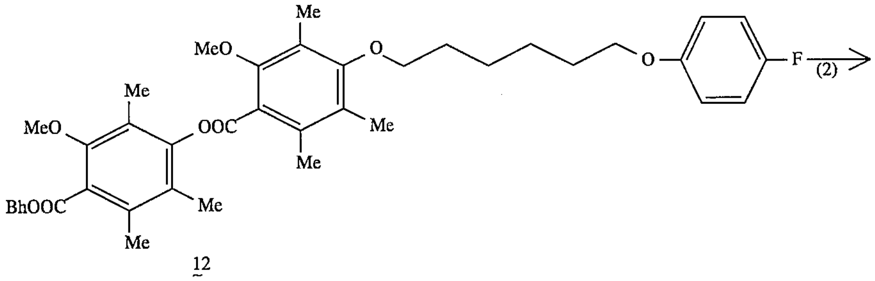

12

-continued

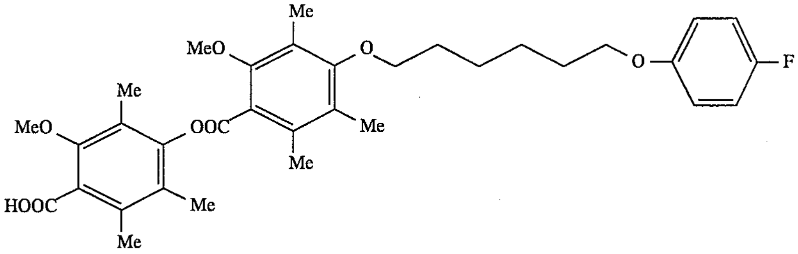

13

(1) Compound 1 was allowed to react with compound 11 obtained in Preparation 4, in the same manner as in Example 1 (1), and the crude product obtained was purified by chromatography on a column of silica gel [$SiO_2$, developed with hexane-ethyl acetate (9:1)] to give compound 12 as an oil (yield 72%).

$^1$H NMR ($CDCl_3$): δ1.51–1.67 (m, 4H), 1.78–1.93 (m, 4H), 2.04–2.38 (m, 18H), 3.56 (s, 3H), 3.70–3.83 (m, 5H), 3.95 (t, J=6.4 Hz, 2H), 6.79–7.02 (m, 4H), 7.19 (s, 1H), 7.23–7.50 (m, 10H)

TLC Rf=0.7 (ethyl acetate:hexane=1:2)

(2) Compound 12 was treated in the same manner as in Example 1 (2), and the crude product obtained was recrystallized from ether-hexane to give compound 13 as colorless crystals (yield 72%)

Melting point 147°–148° C.

$^1$H NMR ($CDCl_3$): δ1.52–1.68 (m, 4H), 1.76–1.93 (m, 4H), 2.18–2.40 (m, 18H), 3.76 (t, J=6.4 Hz, 2H), 3.81 (s, 3H), 3.86 (s, 3H), 3.95 (t, J=6.2 Hz, 2H), 6.79–7.02 (m, 4H)

IR (Nujol): 1743, 1700, 1574, 1505, 1324, 1291, 1210, 1155, 1097, 1075 $cm^{-1}$ Elementary analysis (%) for $C_{34}H_{41}FO_8$ Calcd: C, 68.44; H, 6.93; F, 3.18

Found: C, 68.25; H, 6.95; F, 3.22

EXAMPLE 5

4-[4-[6-(4-Fluorophenylthio)hexyloxy]-2-methoxy-3,5,6-trimethylphenylcarboxy]-2-methoxy-3,5,6-trimethylbenzoic acid (16)

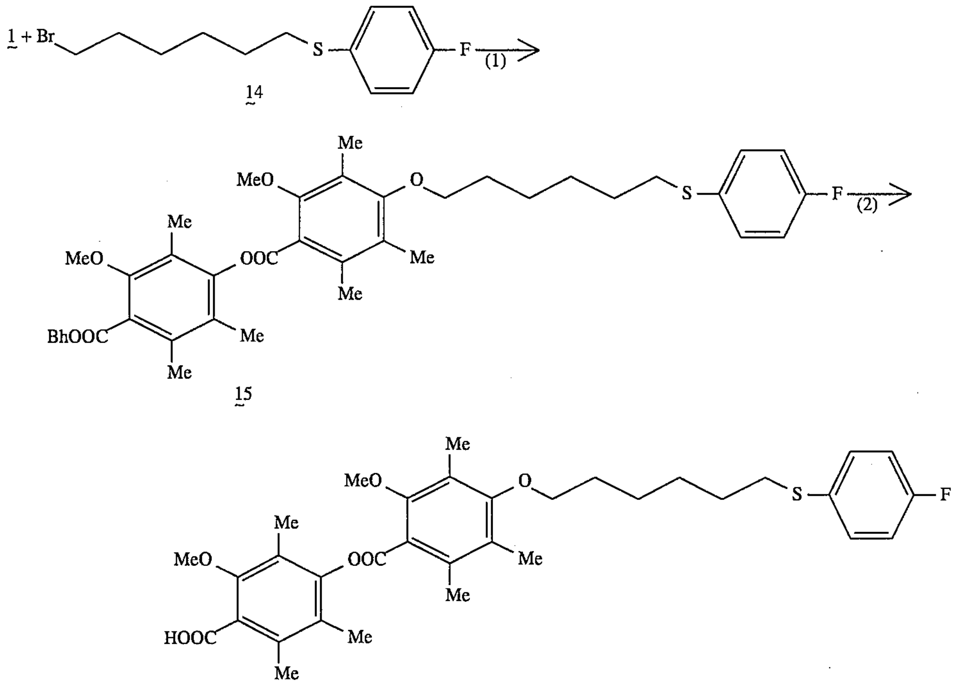

14

15

16

(1) Compound 1 was allowed to react with compound 14 obtained in Preparation 5, in the same manner as in Example 1 (1), and the crude product obtained was purified by chromatography on a column of silica gel [$SiO_2$, developed with hexane-ethyl acetate (19:1)-(4:1)] to give oily compound 15 as an oil (yield 100%).

$^1$H NMR ($CDCl_3$): δ1.46–1.91 (m, 8H), 2.08 (s, 3H), 2.16–2.28 (m, H), 2.34 (s, 3H), 2.90 (t, J=7.2 Hz, 2H), 3.56 (s, 3H), 3.72 (t, J=7.2 Hz, 2H), 3.79 (s, 3H), 6.92–7.07 (m, 2H), 7.19 (s, 1H), 7.27–7.50 (m, 12H)

TCL Rf=0.5 (ethyl acetate:hexane=1:2)

(2) Compound 15 was treated in the same manner as in Example 1 (2), and the crude product obtained was recrystallized from methylene chloride-hexane to give compound 16 as colorless crystals (yield 98%).

Melting point 137°–140° C.

$^1$H NMR ($CDCl_3$): δ1.48–1.90 (m, 8H), 2.16–2.49 (m, 18H), 2.90 (t, J=7.2 Hz, 2H), 3.73 (t, J=6.4 Hz, 2H), 3.81 (s, 3H), 3.86 (s, 3H), 6.92–7.08 (m, 2H), 7.30–7.40 (m, 2H)

IR (Nujol): 1743, 1712, 1575, 1490, 1323, 1280, 1217, 1159, 1095 $cm^{-1}$

Elementary analysis for $C_{34}H_{41}FO_7S \cdot 0.4H_2O$

Calcd: C, 65.87; H, 6.80; F, 3.06; S, 5.17

Found: C, 65.60; H, 6.71; F, 3.21; S, 5.10

EXAMPLE 6

4-[4-[6-(4-Fluorophenylsulfonyl) hexyloxy]-2-methoxy-3,5,6-trimethylphenylcarboxy]-2-methoxy-3,5,6-trimethylbenzoic acid (19)

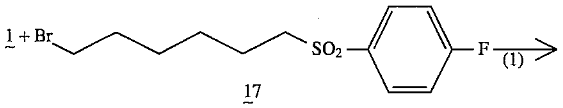

17

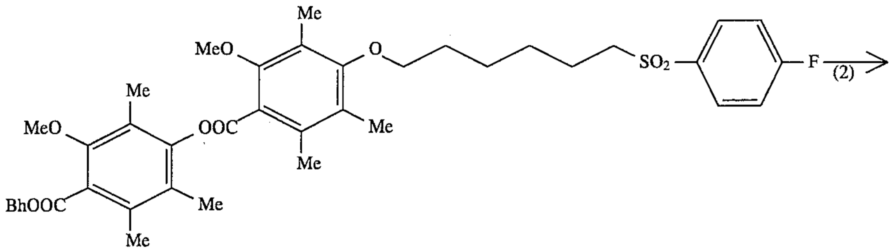

18

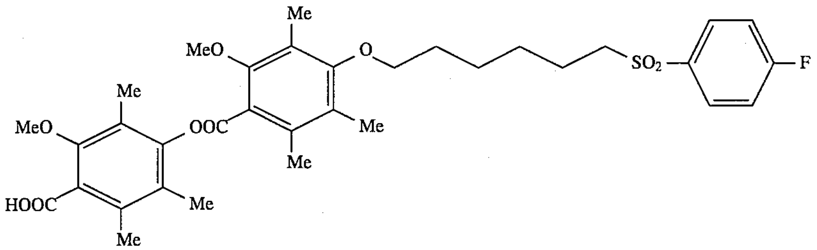

17

(1) Compound 1 was allowed to react with compound 17 obtained in Preparation 6, in the same manner as in Example 1 (1), and the crude product obtained was purified by chromatography on a column of silica gel [$SiO_2$, developed with hexane-ethyl acetate (19:1)–(2:1)] to give compound 18 as a gelatinous substance (yield 100%).

$^1$H NMR ($CDCl_3$): δ1.43–1.61 (m, 4H), 1.70–1.88 (m, 4H), 2.08 (s, 3H), 2.13–2.28 (m, 12H), 2.34 (s, 3H), 3.05–3.18 (m, 2H), 3.56 (s, 3H), 3.70 (t, J=6.2 Hz, 2H), 3.79 (s, 3H), 7.07–7.50 (m, 13H), 7.89–8.01 (m, 2H)

TLC Rf=0.16 (ethyl acetate:hexane=1:2)

(2) Compound 18 was treated in the same manner as in Example 1 (2), and the crude product obtained was recrystallized from methylene chloride-hexane to give compound 19 as colorless crystals (yield 96%).

$^1$H NMR ($CDCl_3$:$CD_3OD$=9:1): δ1.47–1.61 (m, 4H), 1.71–1.89 (m, 4H), 2.16–2.41 (m, 18H), 3.09–3.11 (m, 2H), 3.68–3.79 (m, 2H), 3.81 (s, 3H), 3.83 (s, 3H), 7.22–7.38 (m, 2H), 7.90–8.01 (m, 2H)

IR (Nujol): 3170, 1728, 1590, 1493, 1281, 1235, 1164 $cm^{-1}$

EXAMPLE 7

4-[4-[3-(3, 5-Di-tert-butyl-4-methoxyphenylthio) propyloxy]-2-methoxy-3,5,6-trimethylphenylcarboxy]-2-methoxy-3,5,6-trimethylbenzoic acid (22)

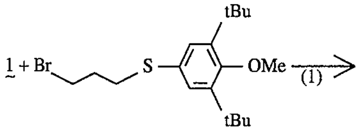

20

-continued

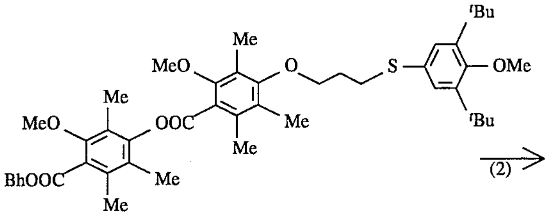

21

-continued

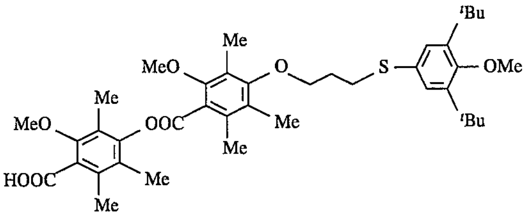

22

(1) Compound 1 was allowed to react with compound 20 obtained in Preparation 7, in the same manner as in Example 1 (1), and the crude product obtained was purified by chromatography on a column of silica gel [$SiO_2$, developed with hexane-ethyl acetate (19:1)–(4:1)] to give compound 21 as a foam (yield 100%).

$^1$H NMR ($CDCl_3$): δ1.42 (s, 18H), 2.07–2.28 (m, 17H), 2.34 (s, 3H), 3.16 (t, J=7.1 Hz, 2H), 3.56 (s, 3H), 3.68 (s, 3H), 3.79 (s, 3H), 3.86 (t, J=6.2 Hz, 2H), 7.19 (s, 1H), 7.24–7.50 (m, 12H)

TLC Rf=0.5 (ethyl acetate:hexane=1:2)

(2) Compound 21 was treated in the same manner as in Example 1 (2), and the crude product obtained was purified by chromatography on a column of silica gel [$SiO_2$, developed with methylene chloride-methanol (1:0)–(4:1)] and was lyophilized from benzene to give compound 22 as powders (yield 81%).

$^1$H NMR ($CDCl_3$: $CD_3OD$ =9:1): δ1.43 (s, 18H), 2.04–2.32 (m, 17H), 2.35 (s, 3H), 3.16 (t, J=7.2 Hz, 2H), 3.69 (s, 3H), 3.81 (s, 3H), 3.83 (s, 3H), 3.88 (t, J=6.0 Hz, 2H), 7.30 (s, 2H)

IR (Nujol): 1740, 1695, 1570, 1406, 1156, 1098, 1073 $cm^{-1}$

Elementary Analysis for $C_{40}H_{50}O_8S{\bullet}0.6H_2O$

Calcd: C, 68.08; H, 7.88; S, 4.54

Found: C, 67.81; H, 7.75; S, 4.44

EXAMPLE 8

4-[4-(4-Fluorobenzyloxy)-2-methoxy-3,5,6-trimethylphenylcarboxy]-2-methoxy-3,5,6-trimethylbenzoic acid (25)

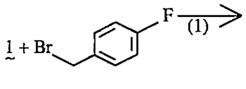

23

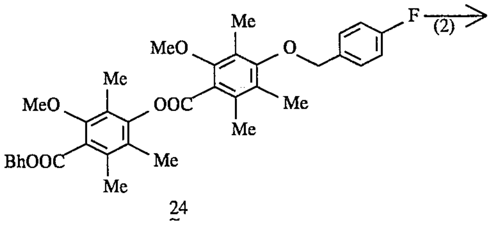

24

-continued

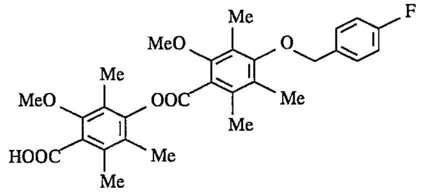

25

(1) Compound 1 was allowed to react with p-fluorobenzyl bromide 23 in the same manner as in Example 1 (1), and the crude product obtained was purified by chromatography on a column of silica gel [$SiO_2$, developed with hexane-ethyl acetate (19:1)–(9:1)] and recrystallized from ether-hexane to give compound 24 as colorless crystals (yield 92%).

Melting point 151°–153° C.

$^1$H NMR ($CDCl_3$): δ2.09 (s, 3H), 2.17–2.29 (m, 12H), 2.37 (s, 3H), 3.57 (s, 3H), 3.81 (s, 3H), 4.76 (s, 2H), 7.04–7.17 (m, 2H), 7.19 (s, 1H), 7.29–7.52 (m, 12H)

IR (Nujol): 1738, 1725, 1605, 1573, 1510, 1324, 1279, 1162, 1095, 1074, 986 $cm^{-1}$ Elementary Analysis (%) for $C_{42}H_{41}FO_7$ Calcd: C, 74.54; H, 6.11; F, 2.81

Found: C, 74.48; H, 6.16; F, 2.86

(2) Compound 24 was treated in the same manner as in Example 1 (2), and the crude product obtained was recrystallized from methylene chloride-hexane to give compound 25 as colorless crystals (yield 96%).

Melting point 209°–211° C.

$^1$H NMR ($CDCl_3$:$CD_3OD$=9:1): δ2.17–2.33 (m, 15H), 2.37 (s, 3H), 3.82 (s, 3H), 3.83 (s, 3H), 4.78 (s, 2H), 7.05–7.19 (m, 2H), 7.43–7.52 (m, 2H)

IR (Nujol): 1737, 1700, 1605, 1575, 1515, 1326, 1224, 1159, 1100, 1077, 986 $cm^{-1}$ Elementary Analysis (%) for $C_{29}H_{31}FO_7$ Calcd: C, 68.22; H, 6.12; F, 3.72

Found: C, 67.93; H, 6.13; F, 3.76

EXAMPLE 9

4-[4-Benzyloxy-2-methoxy-3,5,6-trimethylphenylcarboxy) 2-methoxy-3,5,6-trimethylbenzoic acid (28)

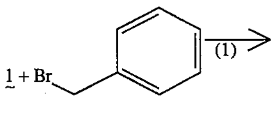

26

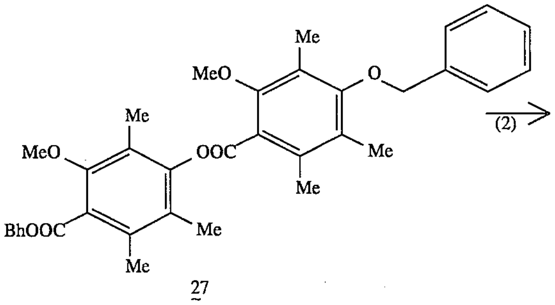

27

-continued

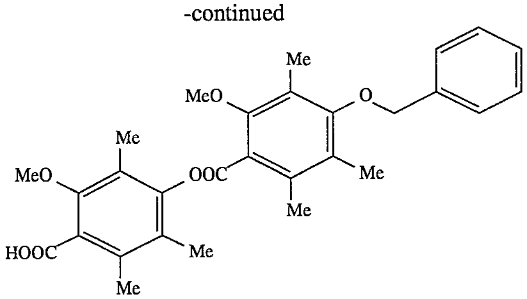

28

(1) Compound 1 was allowed to react with benzyl bromide 26 in the same manner as in Example 1 (1), and the crude product obtained was purified by chromatography on a column of silica gel $SiO_2$, developed with toluene-ethyl acetate (99:1)] and recrystallized from ether-hexane to give compound 27 as colorless crystal (yield 84%).

Melting point 183°–185° C.

$^1$H NMR ($CDCl_3$): δ2.09 (s, 3H), 2.16–2.30 (m, 12H), 2.37 (s, 3H), 3.58 (s, 3H), 3.81 (s, 3H), 4.80 (s, 2H), 7.20 (s, 1H), 7.28–7.55 (m, 15H)

IR (Nujol): 1760, 1723, 1573, 1156 $cm^{-1}$

Elementary Analysis (%) for $C_{42}H_{42}O_7$

Calcd: C, 76.57; H, 6.43

Found: C, 76.83; H, 6.55

(2) Compound 27 was treated in the same manner as in Example 1 (2), and the crude product obtained was recrystallized from methylene chloride-hexane to give compound 28 as olorless crystals (yield 76%).

Melting point 200°–202° C.

$^1$H NMR ($CDCl_3$): δ2.13–2.42 (m, 18H), 3.82 (s, 3H), 3.86 (s, 3H), 4.81 (s, 2H), 7.35–7.55 (m, 5H)

IR (Nujol): 1739, 1699, 1573, 1320, 1280, 1223, 1162, 1100, 1080 $cm^{-1}$

Elementary Analysis (%) for $C_{29}H_{32}O_7$

Calcd: C, 70.71; H, 6.55

Found: C, 70.80; H, 6.71

EXAMPLE 10

4-[4-[3-(4-Fluorophenylthio)propyloxy]-2-methoxy-3,5,6-trimethylphenylcarboxy]-2-methoxy-3,5,6-trimethylbenzoic acid (31)

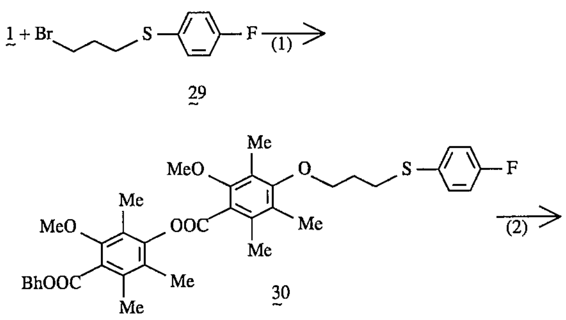

29

30

-continued

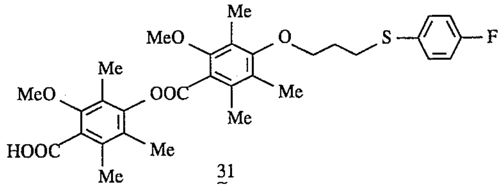

31

(1) Compound 1 was allowed to react with compound 29 obtained in Preparation 8, in the same manner as in Example 1 (1), and the crude product obtained was recrystallized from ether-hexane to give compound 30 as colorless crystals (yield 93%).

Melting point 133°–134° C.

$^1$H NMR ($CDCl_3$): δ2.03–2.31 (m, 17H), 2.34 (s, 3H), 3.15 (t, J=7.2 Hz, 2H), 3.56 (s, 3H), 3.79 (s, 3H), 3.85 (t, J=6.2 Hz, 2H), 6.96–7.06 (m, 2H), 7.19 (s, 1H), 7.27–7.50 (m, 12H)

IR (Nujol): 1742, 1727, 1588, 1577, 1489, 1324, 1280, 1226, 1163, 1097 $cm^{-1}$ Elementary Analysis (%) for $C_{44}H_{45}FO_7{}^S$ Calcd: C, 71.72; H, 6.16; F, 2.58; S, 4.35

Found: C, 71.31; H, 6.20; F, 2.80; s, 4.53

(2) Compound 30 was treated in the same manner as in Example 1 (2), and the crude product obtained was purified by chromatography on a column of silica gel [$SiO_2$, developed with methylene chloride-methanol (1:0)–(4:1)] and lyophilized from benzene to give compound 31 as powders (yield 94%).

$^1$H NMR ($CDCl_3$: $CD_3OD$=9:1): δ2.02–2.30 (m, 17H), 2.35 (s, 3H), 3.17 (t, J=7.0 Hz, 2H), 3.76–3.92 (m, 8H), 6.95–7.09 (m, 2H), 7.33–7.48 (m, 2H)

IR (Nujol): 1738, 1701, 1589, 1575, 1491, 1.324, 1279, 1222, 1158, 1099, 1077 $cm^{-1}$

EXAMPLE 11

4-[4-[6-(4-Chlorophenoxy)hexyloxy]-2-methoxy-3,5,6-trimethylphenylcarboxy]-2-methoxy-3,5,6-trimethylbenzoic acid (34)

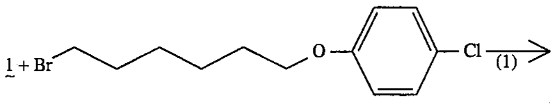

32

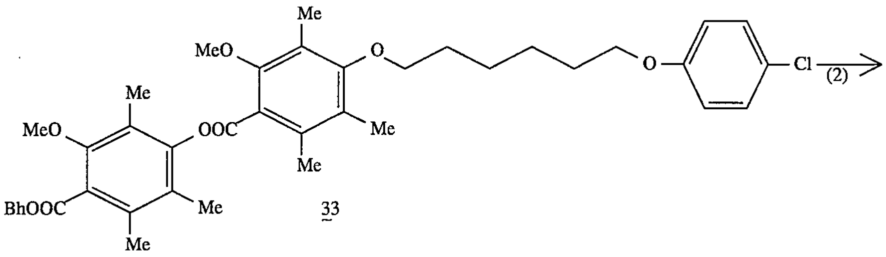

33

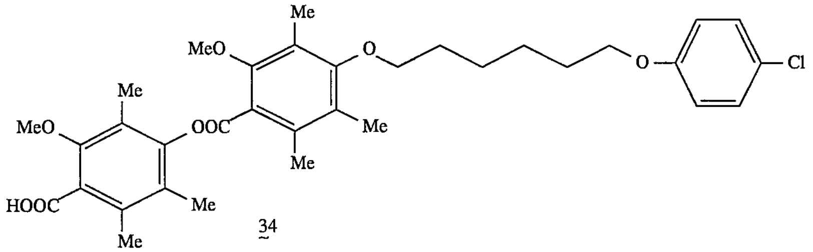

34

(1) Compound 1 was allowed to react with compound 32 obtained in Preparation 9, in the same manner as in Example 1 (1), and the crude product obtained was purified by chromatography on a column of silica gel [$SiO_2$, developed with hexane-ethyl acetate (19:1)-(4:1)] to give compound 33 as a foam (yield 98%).

$^1$H NMR ($CDCl_3$): δ1.50–1.68 (m, 4H), 1.77–1.94 (m, 4H), 2.08 (s, 3H), 2.20 (s, 6H), 2.25 (s, 6H), 2.34 (s, 3H), 3.56 (s, 3H), 3.68–3.84 (m, 5H), 3.96 (t, J=6.4 Hz, 2H), 6.77–6.89 (m, 2H), 7.16–7.48 (m, 13H)

Elementary Analysis (%) for $C_{47}H_{51}Cl0_8$

Calcd: C, 72.43; H, 6.60; Cl, 4.55

Found: C, 72.33; H, 6.69; Cl, 4.64

(2) Compound 33 was treated in the same manner as in Example 1 (2), and the crude product obtained was recrystallized from ether-hexane to give compound 34 as colorless crystals (yield Melting point 167°–168° C.

$^1$H NMR ($CDCl_3$: $CD_3OD$=9:1): δ1.51–1.67 (m, 4H), 1.79–1.95 (m, 4H), 2.16–2.31 (m, 15H), 2.35 (s, 3H), 3.70–3.94 (m, 8H), 3.97 (t, J=6.4 Hz, 2H), 6.77–6.89 (m, 2H), 7.18–7.29 (m, 2H)

IR (Nujol): 1744, 1702, 1597, 1578, 1493, 1324, 1289, 1245, 1156, 1099, 1076 $cm^{-1}$

EXAMPLE 12

4-[4-[6-(3,
5-Di-tert-butyl-4-methoxyphenylthio)hexyloxy]-2-methoxy-3, 5,
6-trimethylphenylcarboxy]-2-methoxy-3, 5,
6-trimethylbenzoic acid (37)

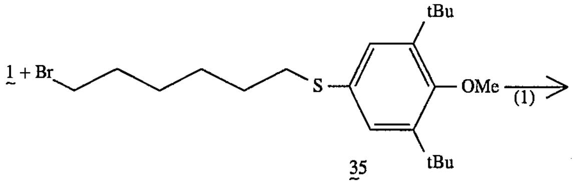

35

-continued

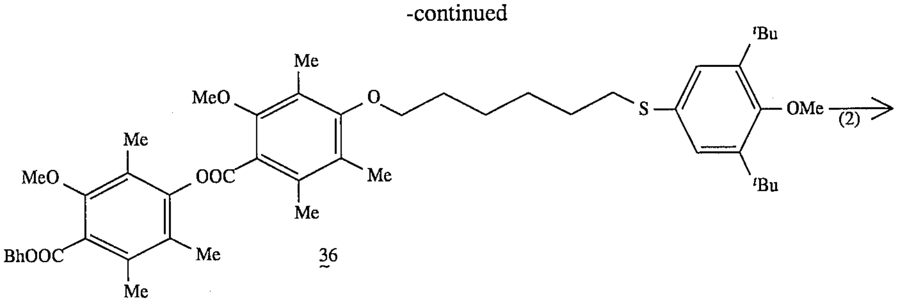

36

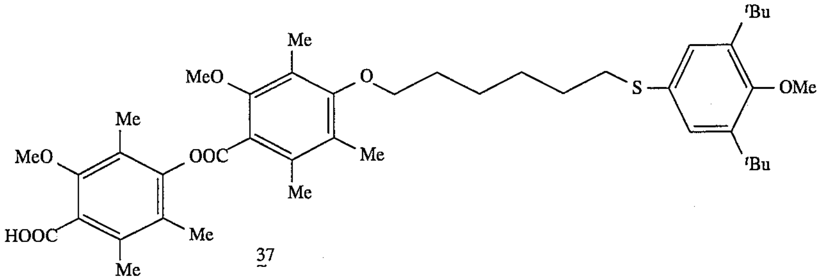

37

(1) Compound 1 was allowed to react with compound 35 obtained in Preparation 10, in the same manner as in Example 1 (1), and the crude product obtained was purified by chromatography on a column of silica gel [$SiO_2$, developed with hexane-ethyl acetate (19:1)] to give compound 36 as a foam (yield 97%).

$^1$H NMR ($CDCl_3$): δ1.42 (s, 18H), 1.49–1.90 (m, 8H), 2.08 (s, 3H),2.16–2.27 (m, 12H), 2.34 (s, 3H), 2.91 (t, J=7.1 Hz, 2H), 3.56 (s, 3H), 3.68 (s, 3H), 3.73 (t, J=6.4 Hz, 2H), 3.79 (s, 3H), 7.19 (s, 1H), 7.23–7.50 (m, 12H)

TLC Rf=0.55 (ethyl acetate:hexane=1:2)

(2) Compound 36 was treated in the same manner as in Example 1 (2), and the crude product obtained was purified by chromatography on a column of silica gel [$SiO_2$, developed with methylene chloride-methanol (1:0)–(49:1)] and lyophilized from benzene to give compound 37 as powders (yield 98%).

$^1$H NMR ($CDCl_3$: $CD_3OD$=9:1): δ1.42 (s, 18H), 1.49–1.62 (m, 4H), 1.64–1.92 (m, 4H), 2.17–2.30 (m, 15H), 2.34 (s, 3H), 2.92 (t, J=7.2 Hz, 2H), 3.68 (s, 3H), 3.75 (t, J=6.6 Hz, 2H), 3.81 (s, 3H), 3.82 (s, 3H), 7.25 (s, 2H)

IR (Nujol): 1744, 1701, 1574, 1410, 1323, 1279, 1222, 1157, 1100, 1078 $cm^{-1}$ Elementary Analysis (%) for $C_{43}H_{60}O_8S{\cdot}H_2O$ Calcd: C, 68.41; H, 8.28; S, 4.25

Found: C, 68.27; H, 7.96; S, 3.86

EXAMPLE 13

4-[6-(3,5-Di-tert-butyl-4-methoxyphenylthio)hexyloxy]-2-methoxy-3,5,6-trimethylbenzoic acid (40)

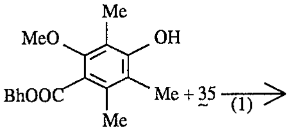

38

-continued

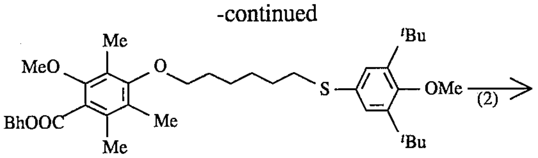

39

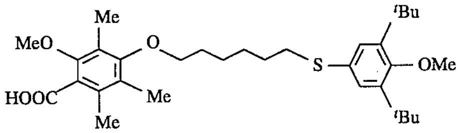

40

(1) Compound 38 (described in the specification of the International Publication WO93/01157) was allowed to react with compound 35 obtained in Preparation 10, in the same manner as in Example 1 (1), and the crude product obtained was purified by chromatography on a column of silica gel [$SiO_2$, developed with hexane-ethyl acetate (49:1)–(19:1)] to give compound 39 as an oil (yield 100%).

$^1$H NMR ($CDCl_3$): δ1.41 (s, 18H), 1.46–1.92 (m, 8H), 2.02 (s, 3H), 2.11 (s, 3H), 2.17 (s, 3H), 2.90 (t, J=7.0 Hz, 2H), 3.52 (s, 3H), 3.62–3.73 (m, 5H), 7.18 (s, 1H), 7.21–7.50 (m, 12H)

TLC Rf=0.55 (ethyl acetate:hexane=1:4)

(2) Compound 39 was treated in the same manner as in Example 1 (2), and the crude product obtained was purified by chromatography on a column of silica gel [$SiO_2$, developed with methylene chloride-methanol (49:1)–(9:1)]. The product was dissolved in benzene and concentrated, followed by such procedure was repeated once more to give compound 40 as an oil (yield 98%).

$^1$H NMR ($CDCl_3$: $CD_3OD$=9:1): δ1.42 (s, 18H), 1.46–1.86 (m, 8H), 2.13 (s,3H), 2.17 (s, 3H), 2.21 (s, 3H), 2.91 (t, J=7.1 Hz, 2H), 3.62–3.75 (m, 5H), 3.77 (s, 3H), 7.24 (s, 2H)

IR (Film): 2739, 2684, 2604, 1734, 1700, 1575, 1458, 1408, 1222, 1112, 1010, 679 $cm^{-1}$ Elementary Analysis (%) for $C_{32}H_{48}O_5S{\cdot}0.2$ Benzene Calcd: C, 71.16; H, 8.85; S, 5.72
Found: C, 71.19; H, 8.79; S. 5.53

EXAMPLE 14

4-[4-[3-(2, 4-difluorophenoxy)propyloxy]-2-methoxy-3, 5, 6-trimethylphenylcarboxy]-2-methoxy-3, 5, 6-trimethylbenzoic acid (43)

1 +
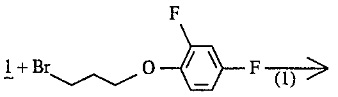

41

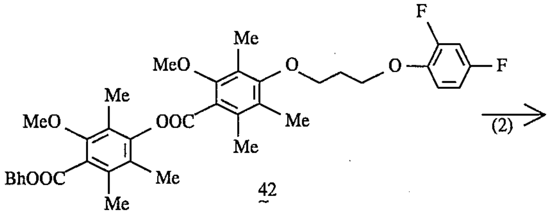

42

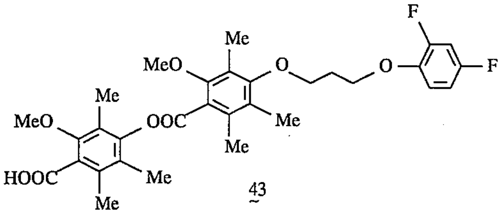

43

(1) Compound 1 was allowed to react with compound 41 obtained in Preparation 11, in the same manner as in Example 1 (1), and the crude product obtained was purified by chromatography on a column of silica gel [$SiO_2$, developed with hexane-ethyl acetate (19:1)-(9:1)] to give compound 42 as a foam (yield 100%).

$^1$H NMR ($CDCl_3$): δ2.08 (s, 3H), 2.15–2.37 (m, 17H), 3.56 (s, 3H), 3.79 (s, 3H), 3.96 (t, J=6.0 Hz, 2H), 4.30 (t, J=6.0 Hz, 2H), 6.75–7.04 (m, 3H), 7.19 (s, 1H), 7.26–7.50 (m, 10H)

TLC Rf=0.45 (ethyl acetate:hexane=1:2)

(2) Compound 42 was treated in the same manner as in Example 1 (2), and the crude product obtained was recrystallized from methylene chloride-hexane to give compound 4.3 as colorless crystal (yield 94 % ).

Melting point 99°–101° C.

$^1$H NMR ($CDCl_3$: $CD_3OD$=9:1): δ2.17–2.40 (m, 20H), 3.81 (s, 3H), 3.82 (s, 3H), 3.98 (t, J=6.0 Hz, 2H), 4.31 (t, J=6.0 Hz, 2H), 6.26–7.08 (m, 3H)

IR (Nujol): 1735, 1714, 1699, 1602, 1574, 1515, 1322, 1284, 1261, 1215, 1177, 1097 $cm^{-1}$ Elementary Analysis (%) for $C_{31}H_{34}F_2O_8$•0.1$H_2O$
Calcd: C, 64.82; H, 6.00; F, 6.61
Found: C, 64.60; H, 6.00; F, 6.52

EXAMPLE 15

4-[3-(4-Fluorophenoxy)propyloxy]-2-methoxy-3,5,6-trimethylbenzoic acid (45)

38 + 5 (1)

-continued

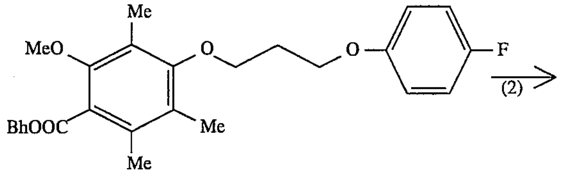

44

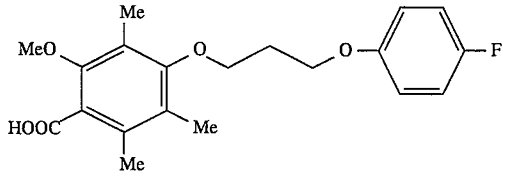

45

(1) Compound 38 was allowed to react with compound 5 obtained in Preparation 2, in the same manner as in Example 1 (1), and the crude product obtained was purified by chromatography on a column of silica gel [$SiO_2$, developed with hexane-ethyl acetate (1:0)-(19:1)] to give compound 44 as a gelatinous substance (yield $^1$H NMR ($CDCl_3$): δ2.02 (s, 3H), 2.09 (s, 3H), 2.14 (s, 3H), 2.25 (quin, d=6.0 Hz, 2H), 3.51 (s, 3H), 3.88 (t, d=6.0 Hz, 2H), 4.19 (t, d=6.0 Hz, 2H), 6.81–7.04 (m, 4H), 7.18 (s, 1H), 7.23–7.47 (m, 10H)

TLC Rf=0.2 (ethyl acetate:hexane=1:4)

(2) Compound 44 was treated in the same manner as in Example 1 (2), and the crude product obtained was recrystallized from methylene chloride-hexane to give compound 45 as a colorless crystals (yield 90%).

Melting point 129°–131° C.

$^1$H NMR ($CDCl_3$:$CD_3OD$=9:1): δ2.13 (s, 3H), 2.17 (s, 3H), 2.19–2.33 (m, 5H), 3.77 (s, 3H), 3.90 (t, J=6.0 Hz, 2H), 4.21 (t, J=6.0 Hz, 2H), 6.83–7.04 (m, 4H)

IR (Nujol): 1696, 1596; 1575, 1508, 1319, 1291, 1251, 1221, 1104, 1063, 987, 832, 746 $cm^{-1}$

EXAMPLE 16

4-[3-(3;5-Di-tert-butyl-4-methoxyphenylthio) propyloxy]-2 -methoxy-3,5,6-trimethylbenzoic acid (47)

38 + 20 (1)

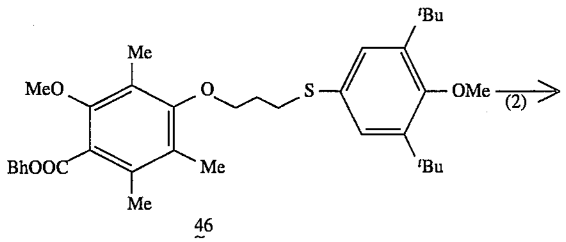

46

-continued

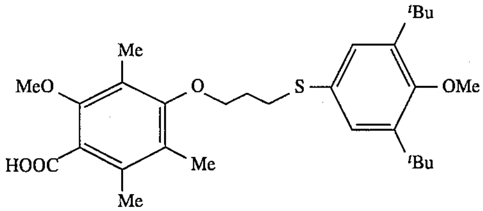

47

(1) Compound 38 was allowed to react with compound 20 obtained in Preparation 7, in the same manner as in Example 1 (1), and the crude product obtained was purified by chromatography on a column of silica gel [$SiO_2$, developed with hexane-ethyl acetate (1:0)–(9:1)] to give compound 46 as gelatinous substances (yield 99%).

$^1$H NMR ($CDCl_3$): δ1.41 (s, 18H), 2.03 (s, 3H), 2.05–2.19 (m, 8H), 3.13 (t, J=6.8 Hz, 2H), 3.52 (s, 3H), 3.67 (s, 3H), 3.80 (t, J=6.0 Hz, 2H), 7.18 (s, 1H), 7.22–7.48 (m, 12H)

TLC Rf=0.45 (ethyl acetate:hexane=1:4)

(2) Compound 46 was treated in the same manner as in Example 1 (2), and the crude product obtained was purified by chromatography on a column of silica gel [$SiO_2$, developed with hexane-ethyl acetate (9:1)—methylene chloride-methanol (4:1)]. The purified product was dissolved in benzene and concentrated, followed by such procedure was repeated once more to give compound 47 as gelatinous substances (yield 83%).

$^1$H NMR ($CDCl_3$: $CD_3OD$=9:1): δ1.42 (s, 18H), 2.04–2.23 (m, 11H), 3.14 (t, J=7.1 Hz, 2H), 3.68 (s, 3H), 3.78 (s, 3H), 3.82 (t, J=6.2 Hz, 2H), 7.29·(s, 2H)

IR (Film): 2960, 2871, 1734, 1700, 1575, 1479, 1459, 1408, 1323, 1292, 1256, 1223, 1110, 1010, 679 $cm^{-1}$ Elementary Analysis (%) for $C_{29}H_{42}O_5S$•0.8 Benzene Calcd: C, 71.83; H, 8.35; S, 5.67

Found: C, 71.83; H, 8.43; S, 5.68

EXAMPLE 17

4-[4-[3-(4-Methoxyphenoxy)propyloxy]-2-methoxy-3,5,6-trimethylphenylcarboxy]-2-methoxy-3,5,6-trimethylbenzoic acid (50)

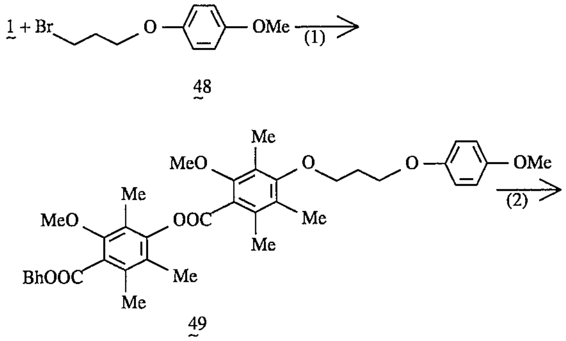

48

49

-continued

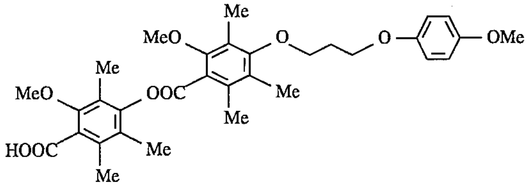

50

(1) Compound 1 was allowed to react with compound 48 obtained in Preparation 12, in the same manner as in Example 1 (1), and the crude product obtained was purified by chromatography on a column of silica gel [$SiO_2$, developed with hexane] to give compound 49 as gelatinous substances (yield 100%).

$^1$H NMR ($CDCl_3$): δ2.04 (s, 3H), 2.17–2.33 (m, 14H), 2.34 (s, 3H), 3.56 (s, 3H), 3.78 (s, 6H), 3.94 (t, J=6.1 Hz, 2H), 4.20 (t, J=6.0 Hz, 2H), 6.80–6.92 (m, 4H), 7.19 (s, 1H), 7.27–7.50 (m, 10H)

TLC Rf=0.15 (ethyl acetate:hexane: 1:4)

(2) Compound 49 was treated in the same manner as in Example 1 (2), and the crude product obtained was purified by chromatography on a column of silica gel [$SiO_2$, developed with hexane-ethyl acetate (19:1)–(0:1)—methylene chloride] and lyophilized from benzene to give compound 50 as powders (yield 82%).

$^1$H NMR ($CDCl_3$:$CD_3OD$=9:1): δ2.16–2.39 (m, 20H), 3.75–3.87 (m, 9H), 3.98 (t, J=6.0 Hz, 2H), 4.22 (t, J=6.0 Hz, 2H), 6.80–6.95 (m, 4H)

IR (Nujol): 1738, 1702, 1575, 1508, 1462, 1323, 1279, 1231, 1156, 1098 $cm^{-1}$ Elementary Analysis (%) for $C_{32}H_{38}O_9$ Calcd: C,67.83; H, 6.76

Found: C, 67.59; H, 6.72

EXAMPLE 18

2-Methoxy-3, 5, 6-trimethyl-4-[3-(2-naphthyloxy)-propyloxy]benzoic acid (53)

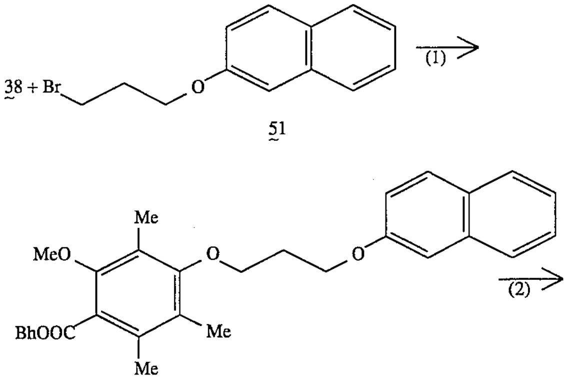

51

52

-continued

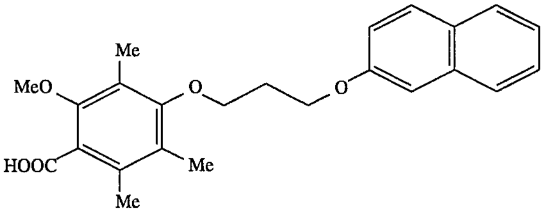

53

(1) Compound 38 was allowed to react with compound 51 obtained in Preparation 13, in the same manner as in Example 1 (1), and the crude product obtained was purified by chromatography on a column of silica gel [$SiO_2$, developed with hexane-ethyl acetate (1:0)–(9:1)] to give compound 52 as an oily (yield 100%).

$^1$H NMR ($CDCl_3$): δ2.02 (s, 3H), 2.11 (s, 3H), 2.16 (s, 3H), 2.23 (quin, J=6.0 Hz, 2H), 3.5](s, 3H), 3.94 (t, J=6.0 Hz, 2H), 4.36 (t, J=6.0 Hz, 2H), 7.11–7.22 (m, 3H), 7.26–7.50 (m, ]2H), 7.70–7.82 (m, 3H)

TLC Rf=0.3 (ethyl acetate:hexane=1:4)

(2) Compound 52 was treated in the same manner as in Example 1 (2), and the crude product obtained was purified by chromatography on a column of silica gel [$SiO_2$, developed with hexane-ethyl acetate (9:1)–(0:1)] and lyophilized from benzene to give compound 53 as powders (yield 97%).

$^1$H NMR ($CDCl_3$: $CD_3OD$=9:1): δ2.15 (s, 3H), 2.18 (s, 3H), 2.22 (s,3H), 2.35 (quin, J=6.0 Hz, 2H), 3.76 (s, 3H), 3.96 (t, J=6.1 Hz, 2H), 4.38 (t, J=6.1 Hz, 2H), 7.12–7.23 (m, 3H), 7.27–7.50 (m, 2H), 7.72–7.89 (m 2H)

IR (Nujol): 1732, 1698, 1629, 1600, 1577, 1511, 1258, 1216, 1181, 1104 $cm^{-1}$ Elementary Analysis (%) for $C_{24}H_{26}O_5$•0.4 Benzene Calcd: C, 74.48; H, 6.72

Found: C, 74.66; H, 6.68

EXAMPLE 19

4-[2-Methoxy-3,5,6-trimethyl-4-[3-(2-naphthyloxy)-propyloxy]phenylcarboxy]-2-methoxy-3,5,6-trimethylbenzoic acid (55)

1 + 51

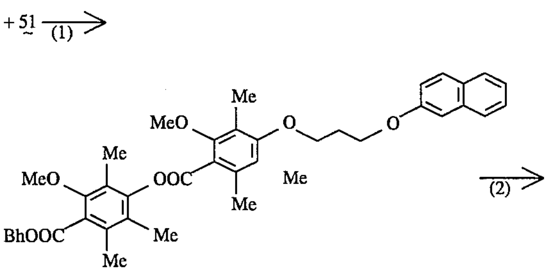

54

-continued

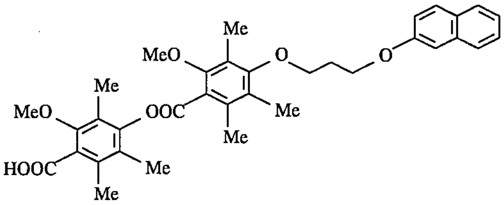

55

(1) Compound 1 was allowed to react with compound 51 obtained in Preparation 13, in the same manner as in Example 1 (1), and the crude product obtained was purified by chromatography on a column of silica gel [$SiO_2$, developed with hexane-ethyl acetate (49:2)–(4:1)] to give compound 54 as gelatinous substances (yield 100%).

$^1$H NMR ($CDCl_3$): δ2.08 (s, 3H), 2.19 (s, 6H), 2.24 (s, 6H), 2.29–2.44 (m, 5H), 3.56 (s, 3H), 3.78 (s, 3H), 3.99 (t, J=6.1 Hz, 2H), 4.39 (t, J=6.1 Hz, 2H), 7.13–7.24 (m, 3H), 7.27–7.51 (m, 12H), 7.71–7.82 (m, 3H)

TLC Rf=0.15 (ethyl acetate:hexane=1:4)

(2) Compound 54 was treated in the same manner as in Example 1 (2), and the crude product obtained was purified by chromatography on a column of silica gel [$SiO_2$, developed with hexane-ethyl acetate (19:1)–(0:1)] and lyophilized from benzene to give compound 55 as powders (yield 75%).

$^1$H NMR ($CDCl_3$: $CD_3OD$=9:1): δ2.17–2.46 (m, 20H), 3.80 (s, 3H), 3.82 (s, 3H), 4.02 (t, J=6.1 Hz, 2H), 4.40 (t, J=6.0 Hz, 2H), 7.13–7.23 (m, 3H), 7.29–7.50 (m, 2H), 7.72–7.84 (m, 2H)

IR (Nujol): 1738, 1702, 1630, 1576, 1323, 1279, 1259, 1217, 1158, 1098 $cm^{-1}$ Elementary Analysis (%) for $C_{35}H_{38}O_8$•0.3 Benzene Calcd: C, 72.45; H, 6.58

Found: C, 72.61; H, 6.57

EXAMPLE 20

4-[4-[3-(3, 4-Dimethoxyphenoxy) propyloxy]-2-methoxy-3, 5, 6-trimethylphenylcarboxy]-2-methoxy-3, 5, 6-trimethylbenzoic acid (58)

1 +

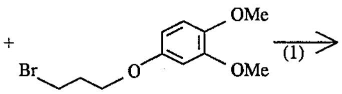

56

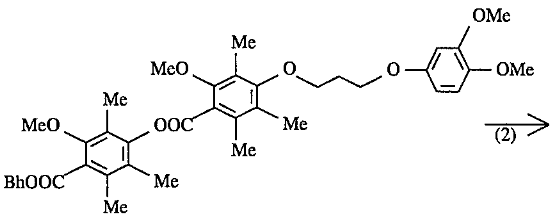

57

-continued

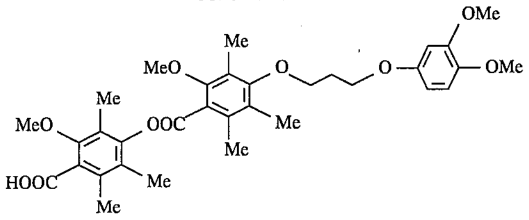

58

(1) Compound 1 was allowed to react with compound 56 obtained in Preparation 14, in the same manner as in Example 1 (1), and the crude product obtained was purified by chromatography on a column of silica gel [$SiO_2$, developed with hexane-ethyl acetate (49:1)–(4:1)] to give compound 57 as gelatinous substances (yield 100%).

$^1$H NMR ($CDCl_3$): δ2.08 (s, 3H), 2.16–2.37 (m, 17H), 3.56 (s, 3H), 3.79 (s, 3H), 3.85 (s, 3H), 3.87 (s, 3H), 3.94 (t, d=6.1 Hz, 2H), 4.21 (t, J=6.0 Hz, 2H), 6.44 (dd, J=8.8 Hz, 3.0 Hz, 1H), 6.55 (d, J=3.0 Hz, 1H), 6.80 (d, J=8.8 Hz, 1H), 7.19 (s, 1H), 7.27–7.48 (m, 10H)

TLC Rf=0.1 (ethyl acetate:hexane=1:4)

(2) To a solution of compound 57 (1.27 g, 1.67 mmol) in ethyl acetate (12 ml) was added a suspension of palladium carbon powder (200 mg) in ethyl acetate (3 ml), and hydrogen gas (37.4 ml, 1.67 mmol) was taken into the mixture at room temperature. The mixture was filtered, concentrated and the crude product obtained was recrystallized from ether-hexane to give compound 58 as colorless crystals (980 mg) (yield 98%).

Melting point 139°–141° C.

$^1$H NMR ($CDCl_3$: $CD_3OD$=9:1): δ2.17–2.38 (m, 20H), 3.80 (s, 3H), 3.82 (s, 3H), 3.85 (s, 3H), 3.87 (s, 3H), 3.97 (t, J=6.0 Hz, 2H), 4.23 (t, J=6.0 Hz, 2H), 6.47 (dd, J=8.8 Hz, 2.8 Hz, 1H), 6.57 (d, J=2.8 Hz, 1H), 6.82 (d, J=8.8 Hz, 1H)

IR (Nujol): 1733, 1595, 1516, 1230, 1166, 1099, 1026 $cm^{-1}$

EXAMPLE 21

4-[4-[3-(2-Benzhydryl-4,5-dimethoxyphenoxy)propyloxy]-2-methoxy-3,5,6-trimethylphenylcarboxy]-2-methoxy-3,5,6-trimethylbenzoic acid (59)

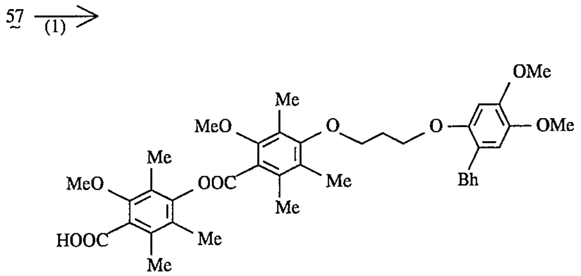

59

(1) Compound 57 obtained in Example 20 (1) was treated in the same manner as in Example 1 (2), and the crude product obtained was recrystallized from ethyl acetate-hexane to give compound 59 as colorless crystals (yield 97%).

Melting point 189°–190° C.

$^1$H NMR ($CDCl_3$: $CD_3OD$=9:1): δ2.01–2.37 (m, 20H), 3.59–3.70 (m, 5H), 3.80 (s, 3H), 3.83 (s, 3H), 3.89 (s, 3H), 4.09 (t, J=6.0 Hz, 2H), 5.82 (s, 1H), 6.41 (s, 1H), 6.60 (s, 1H), 7.01–7.29 (m, 10H)

IR (Nujol): 1746, 1696, 1596, 1576, 1515, 1324, 1211, 1198, 1159, 1096, 1057 $cm^{-1}$ Elementary Analysis (%) for $C_{46}H_{50}O_{10}$•$0.6H_2O$ Calcd: C, 71.41; H, 6.67

Found: C, 71.16; H, 6.60

EXAMPLE 22

4-[4-[3-(4-Trifluoromethylphenylamino)propyloxy]-2-methoxy-3,5,6-trimethylphenylcarboxy]-2-methoxy-3,5,6 trimethylbenzoic acid hydrochloride (62)

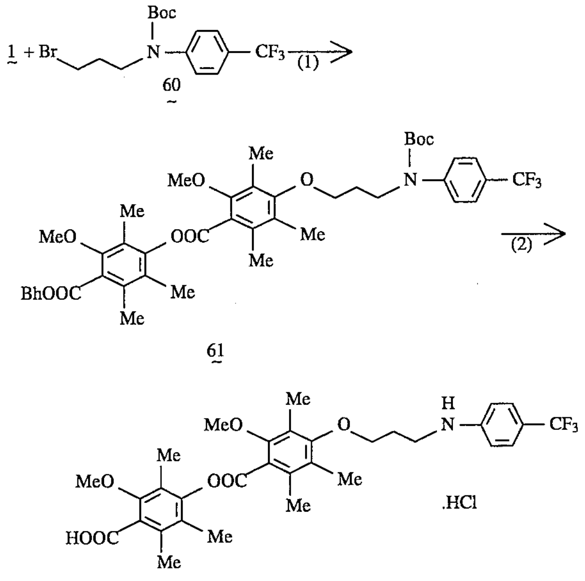

62

(1) Compound 1 was allowed to react with compound 60 obtained in Preparation 15, in the same manner as in Example 1 (1), and the crude product obtained was purified by chromatography on a column of silica gel [$SiO_2$, developed with hexane-ethyl acetate (49:1)–(9:1)] and recrystallized from ether-hexane to give compound 61 as colorless crystals (yield 87%).

Melting point 156°–157° C.

$^1$H NMR ($CDCl_3$): δ1.46 (s, 9H), 2.03–2.26 (m, 17H), 2.33 (s, 3H), 3.56 (s, 3H), 3.70–3.82 (m, 5H), 3.91–4.02 (m, 2H), 7.19 (s, 1H), 7.28–7.50 (m, 12H), 7.57–7.66 (m, 2H)

IR (Nujol): 1731, 1695, 1615, 1275, 1163, 1124, 1063 $cm^{-1}$

Elementary Analysis (%) for $C_{50}H_{54}F_3NO_9$

Calcd: C, 69.03; H, 6.26; N, 1.61; F, 6.55

Found: C, 69.16; H, 6.28; N, 1.55; F, 6.76

(2) Compound 61 was treated in the same manner as in Example 1 (2), and the crude product obtained was partitioned into toluene and 1N aqueous potassium hydroxide solution. The aqueous layer was acidified with 2N hydrochloric acid and extracted with methyl ethyl ketone. The organic layer was washed with water and saturated saline sequentially, dried and concentrated. The residue was crystallized by mixing with ethyl acetate containing hydrogen chloride. The crystals were washed with ethyl acetate-ether to give compound 62 as colorless crystals (yield 73%).

Melting point 109°–114° C.

$^1$H NMR ($CDCl_3$: $CD_3OD$=9:1): δ2.02–2.26 (m, 17H), 2.28 (s, 3H), 3.34 (t, J=7.0 Hz, 2H), 3.73 (s, 6H), 3.88 (t, J=6.1 Hz, 2H), 6.73 (d, J=8.4 Hz, 2H), 7.40 (d, J=8.4 Hz, 2H)

IR (Nujol): 2740, 2630, 2510, 2430, 1736, 1716, 1620, 1576, 1280, 1164, 1138, 1097, 1071, 987 $cm^{-1}$ Preparation 16

Synthesis of benzhydryl 4-(2-methoxy-3,5,6-trimethyl-4-hydroxybenzoyloxy)- 2-methoxy-3,5,6-trimethylbenzoate (referred to as Deg. B-Bh-ester hereinafter)

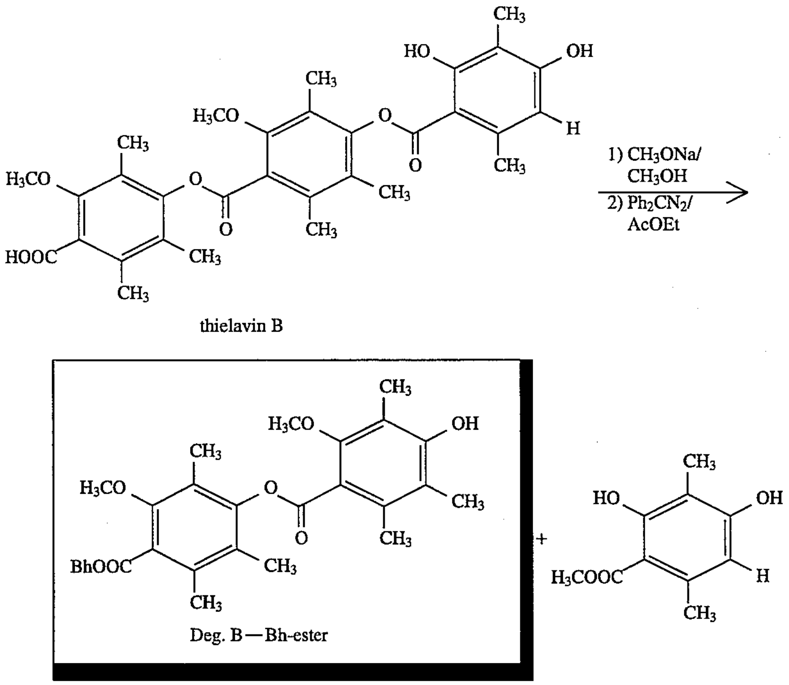

thielavin B

Deg. B—Bh-ester

Fifty g of Thielavin B (about 71 mmol as about 80% purify) which is described in The Journal of Antibiotics, vol 36, No. 5 (1983), p599–600 was dissolved in 200 ml of dry methanol. To the solution was added about 28% NaoMe/MeOH (85 ml, 0.44 mol), and the mixture was stirred at 50° C. for 5 hours. Then, the mixture was concentrated, added with 2N-HCl (90 ml), extracted with ethyl acetate (200 ml), and crystallized. Then, the crystals were suspended in ethyl acetate, and to the suspension was added diphenyl diazomethane at room temperature with stirring. The suspension was stirred at room temperature for 1 hour, concentrated, and crystallized from toluene to give Deg. B-Bh-ester quantitatively.

EXAMPLES 23–43

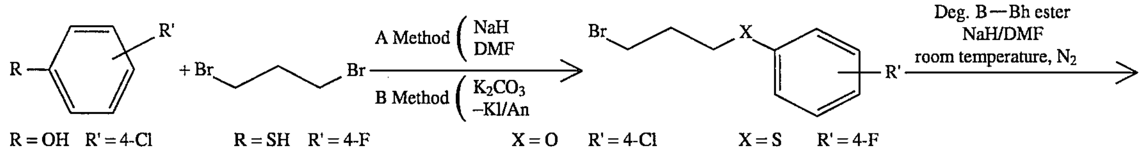

| | | | | | | | |
|---|---|---|---|---|---|---|---|
| R = OH | R' = 4-Cl | R = SH | R' = 4-F | X = O | R' = 4-Cl | X = S | R' = 4-F |
| | 2,4-Cl | R = OH | 2,3-F | | 2,4-Cl | X = $SO_2$ | 4-F |
| | 4-Br | | 2,6-F | | 4-Br | X = O | 2,3-F |
| | 2,4-Br | | 2-$OCH_3$ | | 2,4-Br | | 2,6-F |
| | 4-$CH_3$ | | 2,6-$OCH_3$ | | 4-$CH_3$ | | 2-$OCH_3$ |
| | 4-$CH_2CH_3$ | | 3,5-$OCH_3$ | | 4-$CH_2CH_3$ | | 2,6-$OCH_3$ |
| | 4-$COCH_3$ | | 4-$CONH_2$ | | 4-$COCH_3$ | | 3,5-$OCH_3$ |
| | 4-$CO_2$Bh | | 4-$CO_2CH_3$ | | 4-$CO_2$Bh | | 4-$CONH_2$ |
| | 3,4-$OCH_2O$— | | | | 3,4-$OCH_2O$— | | 4-$CO_2CH_3$ |
| | 2-F | | | | 2-F | | |
| | 3-F | | | | 3-F | | |

-continued

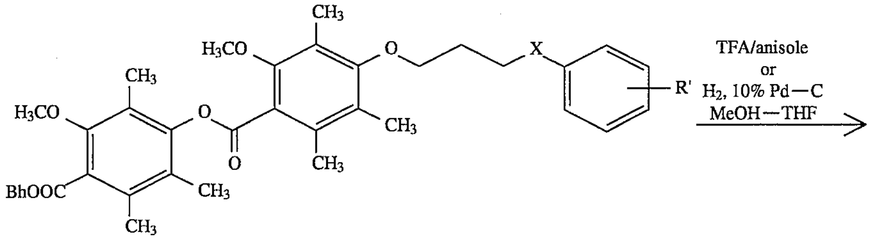

X = O R' = 4-Cl
2,4-Cl
4-Br
2,4-Br
$4-CH_3$
$4-CH_2CH_3$
$4-COCH_3$
$4-CO_2Bh$
$3,4-OCH_2O-$
2-F
3-F

X = S R' = 4-F
$X = SO_2$ 4-F
X = O 2,3-F
2,6-F
$2-OCH_3$
$2,6-OCH_3$
$3,5-OCH_3$
$4-CONH_2$
$4-CO_2CH_3$

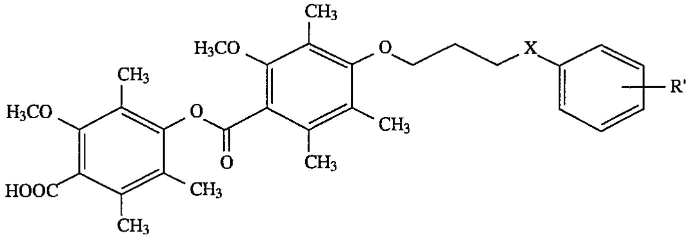

X = O R' = 4-Cl 78
2,4-Cl 79
4-Br 80
2,4-Br 81
$3,4-OCH_2O-$, 6-Bh 82
$3,4-OCH_2O-$ 83
$4-CH_3$ 84
$4-CH_2CH_3$ 85
$4-COCH_3$ 86
$4-CO_2H$ 87
2-F 88
3-F 89

X = S R' = 4-F 90
$X = SO_2$ 4-F 91
X = O 2,3-F 92
2,6-F 93
$2-OCH_3$ 94
$2,6-OCH_3$ 95
$3,5-OCH_3$ 96
$4-CONH_2$ 97
$4-CO_2CH_3$ 98

Method A NaH (1.05 g, 26.25 mmol, 60% in oil, rinsed with hexane) was suspended in 15 ml of dry DMF, and to the suspension were added various phenol derivatives or thiophenol derivatives (25 mmol in 5 ml of DMF solution) under ice cooling in a $N_2$ gas with stirring. 1, 3-Dibromopropane (50.5 g, 0.25 mol in 25 ml of DMF solution) was added to the suspension, and the mixture was stirred at 90°–100° C. for 24–48 hours. Then, the resulting mixture was concentrated to give the residue, which residue was then added with water, and the mixture was extracted with ethyl acetate. The organic layer was washed with water, dried, concentrated, and the residue was dried. The residue was purified by either crystallization from ether-hexane or chromatography on silica gel (developed with hexane-ethyl acetate (1:0–2:1)).

Method B Phenol (10 mmol), $K_2CO_3$ (30 mmol), KI (2 mmol), and 1, 3-dibromopropane (100 mmol) were heated under reflux in 40 ml of acetone for 6–60 hours, and the mixture was treated in the same manner as in Method A.

Then, the resultant compound was etherified with Deg. B-Bh-Ester using NaH/DMF according to the same manner as in Method A. Subsequently, the benzhydryl group was removed by treating the ether with TFA/Anisole or hydrogen gas on 10% Pd-C in MeOH/THF (2:1), to give the title compound (—COOH form).

EXAMPLE 23

4-{4-[3-(4-Chlorophenoxy)propoxy]-2-methoxy-3,5,6-trimethylbenzoyloxy}-2-methoxy-3,5,6-trimethylbenzoic Acid (78)

Melting point 119°–124° C.

$^1$H NMR ($CDCl_3$): δ2.18(3H, s), 2.23(3H, s), 2.25(3H, s), 2.28(3H, s), 2.35(6H, s), 2.34–2.39(2H, m), 3.80(3H, s), 3.86(3H, s), 3.94(2H, t, J=6.0 Hz), 4.24(2H, t, J=6.0 Hz), 6.88(2H, d, J=9.0 Hz), 7.26(2H, d, J=9.0 Hz).

IR ($CHCl_3$) 1732, 1700(sh), 1595, 1575 $cm^{-1}$

Elementary Analysis for $C_{31}H_{35}ClO8$:

Calcd: C, 65.20;H, 6.18;CI, 6.21.

Found: C, 65.35;H, 6.26;CI, 5.92.

EXAMPLE 24

4-{4-[3-(2, 4-Dichlorophenoxy)propoxy]-2-methoxy-3,5,6-trimethylbenzoyloxy}-2-methoxy-3,5,6-trimethylbenzoic Acid (79)

Melting point 162°–164° C.

$^1H$ NMR ($CDCl_3$): δ2.17(3H, s), 2.23(3H, s), 2.25(3H, s), 2.28(3H, s), 2.35(6H, s), 2.17–2.41(2H, m), 3.80(3H, s), 3.86(3H, s), 3.99(2H, t, J=5.8 Hz), 4.31 (2H, t, J=5.8 Hz), 6.92(1 H, d, J=8.8 Hz), 7.21(1H, d, d, J=8.8, 2.6 Hz), 7.39(1H, d, J=2.4 Hz).

IR ($CHCl_3$): 1732, 1700(sh), 1574 $cm^{-1}$.

Elementary Analysis for $C_{31}H_{34}Cl_2O_8$:

Calcd: C, 61.49;H, 5.66;Cl, 11.71.

Found: C, 61.66;H, 5.73;Cl, 11.41.

EXAMPLE 25

4-{4-[3-(4-Bromophenoxy)propoxy]-2-methoxy-3,5,6-trimethylbenzoyloxy}-2-methoxy-3,5,6-trimethylbenzoic Acid (80)

Melting point 126°–131° C.

$^1H$ NMR ($CDCl_3$): δ2.18(3H, s), 2.23(3H, s), 2.25(3H, s), 2.28(3H, s), 2.35(6H, s), 2.18–2.35(2H, m), 3.80(3H, s), 3.86(3H, s), 3.94(2H, t, J=6.0 Hz), 4.24(2H, t, J=6.0 Hz), 6.83(2H, d, J=9.0 Hz), 7.40(2H, d, J=9.0 Hz).

IR ($CHCl_3$): 1732, 1700(sh), 1590, 1570 $cm^{-1}$.

Elementary Analysis for $C_{31}H_{35}BrO_8$:

Calcd: C, 60.49;H, 5.73;Br, 12.98.

Found: C, 60.38;H, 5.73;Br, 13.15.

EXAMPLE 26

4-{4-[3-(2, 4-Dibromophenoxy)propoxy]-2-methoxy-3,5,6-trimethylbenzoyloxy}-2-methoxy-3,5,6-trimethylbenzoic Acid (81)

Melting point 170°–172° C.

$^1H$ NMR ($CDCl_3$): δ2.17(3H, s), 2.23(3H, s), 2.25(3H, s), 2.28(3H, s), 2.35(6H, s), 2.17–2.43(2H, m), 3.80(3H, s), 3.86(3H, s), 4.01(2H, t, J=5.8 Hz), 4.31 (2H, t, J=5.8 Hz), 6.84(1 H, d, J=8.8 Hz), 7.40(1H, d, d, J=8.8, 2.3 Hz), 7.69(1H, d, J=2.3 Hz).

IR ($CHCl_3$): 1732, 1705(sh), 1576 $cm^{-1}$.

Elementary Analysis for $C_{31}H_{34}Br_2O_8$:

Calcd: C, 53.62;H, 4.94;Br, 23.01.

Found: C, 53.88;H, 4.97;Br, 22.78.

EXAMPLE 27

4-{4-[3-(6-Benzhydrylbenzo[1, 3]dioxol-5-yloxy)-propoxy]-2-methoxy-3,5,6-trimethylbenzoyloxy}-2-methoxy-3,5,6-trimethylbenzoic Acid (82)

Melting point 209°–213° C.

$^1H$ NMR ($CDCl_3$+$CD_3OD$): δ1.96–2.31(2H, m), 2.06(3H, s), 2.12(3H, s), 2.17(3H, s), 2.22(6H, s), 2.31(3H, s), 3.61(2H, t, J=6.0 Hz), 3.76(6H, s), 4.03(2H, t, J=6.0 Hz), 5.80(1H, s), 5.89(2H, s), 6.35(1H, s), 6.57(1H, s), 7.03–7.28(10H, m).

IR ($CHCl_3$): 3375, 1733, 1573 $cm^{-1}$.

Elementary Analysis for $C_{45}H_{46}O_{10}$:

Calcd: C, 72.37;H, 6.21.

Found: C, 53.88;H, 4.97;Br, 22.78.

EXAMPLE 28

4-{4-[3-(Benzo[1, 3]dioxol-5-yloxy)propoxy]-2-methoxy-3,5,6-trimethylbenzoyloxy}-2-methoxy-3,5,6-trimethylbenzoic Acid (83)

Melting point 144°–145° C.

$^1H$ NMR ($CDCl_3$): δ2.19(3H, s), 2.24(3H, s), 2.25(3H, s), 2.29(3H, s), 2.35(6H, s), 2.19–2.35(2H, m), 3.80(3H, s), 3.86(3H, s), 3.93(2H, t, J=6.0 Hz), 4.19(2H, t, J=5.8 Hz), 6.37(1H, d, d, J=8.4, 2.6 Hz), 6.54(1H, d, J=2.4 Hz), 6.73(1 H, d, J=8.4 Hz).

IR ($CHCl_3$): 3490, 1733, 1700(sh), 1625, 1600, 1570 $cm^{-1}$.

Elementary Analysis for $C_{32}H_{36}O_{10}$:

Calcd: C, 66.20;H, 6.25.

Found: C, 66.21;H, 6.26.

EXAMPLE 29

4-{4-[3-(4-Methylphenoxy)propoxy]-2-methoxy-3,5,6-trimethylbenzoyloxy}-2-methoxy-3,5,6-trimethylbenzoic Acid (84)

Melting point 127°–129° C.

$^1H$ NMR ($CDCl_3$): δ2.19(3H, s), 2.24(3H, s), 2.25(3H, s), 2.29(3H, s), 2.30(3H, s), 2.35(6H, s), 2.19–2.35(2H, m), 3.80(3H, s), 3.86(3H, s), 3.95(2H, t, J=6.0 Hz), 4.23(2H, t, J=6.0 Hz), 6.85(2H, d, J=8.8 Hz), 7.10(2H, d, J=8.8 Hz).

IR ($CHCl_3$): 3480, 1733, 1700(sh), 1600, 1565 $cm^{-1}$.

Elementary Analysis for $C_{32}H_{38}O_8$:

Calcd: C, 69.80;H, 6.96.

Found: C, 70.04;H, 7.02.

EXAMPLE 30

4-{4-[3-(4-Ethylphenoxy)propoxy]-2-methoxy-3,5,6-trimethylbenzoyloxy}-2-methoxy-3,5,6-trimethylbenzoic Acid (85)

Melting point 118°–121° C.

$^1H$ NMR ($CDCl_3$): δ1.22(3H, t, J=7.6 Hz), 2.20(3H, s), 2.25(6H, s), 2.29(3H, s), 2.35(6H, s), 2.20–2.35(2H, m), 2.61(2H, q, J=7.6 Hz), 3.80(3H, s), 3.86(3H, s), 3.95(2H, t, J=6.0 Hz), 4.24(2H, t, J=6.0 Hz), 6.87(2H, d, J=8.6 Hz), 7.13(2H, d, J=8.6 Hz).

IR ($CHCl_3$): 3480, 1732, 1705(sh), 1605, 1575 $cm^{-1}$.

Elementary Analysis for $C_{33}H_{40}O_8$:

Calcd: C, 70.19;H, 7.14.

Found: C, 70.21;H, 7.13.

EXAMPLE 31

4-{4-[3-(4-Acetylphenoxy)propoxy]-2-methoxy-3,5,6-trimethylbenzoyloxy}-2-methoxy-3,5,6-trimethylbenzoic Acid (86)

Melting point 178°–181° C.

$^1H$ NMR ($CDCl_3$): δ2.18(3H, s), 2.23(3H, s), 2.25(3H, s), 2.28(3H, s), 2.35(6H, s), 2.18–2.35(2H, m), 2.58(3H, s), 3.80(3H, s), 3.86(3H, s), 3.96(2H, t, J=5.8 Hz), 4.35(2H, t, J=5.8 Hz), 6.99(2H, d, J=9.0 Hz), 7.97(2H, d, J=9.0 Hz).

IR ($CHCl_3$): 3475, 1732, 1700(sh), 1672, 1599, 1574 $cm^{-1}$.

Elementary Analysis for $C_{33}H_{38}O_9$:

Calcd: C, 68.50;H, 6.62.

Found: C, 68.29;H, 6.65.

EXAMPLE 32

4-{4-[3-(4-Carboxyphenoxy)propoxy]-2-methoxy-3,5,6-trimethylbenzoyloxy}-2-methoxy-3,5,6-trimethylbenzoic Acid (87)

Melting point 253°–255° C.

$^1$H NMR ($CDCl_3$+$CD_3OD$=14:1): δ2.18(3H, s), 2.22(6H, s), 2.25(3H, s), 2.29(3H, s), 2.34(3H, s), 2.18–2.35(2H, m), 3.80(3H, s), 3.83(3H, s), 3.96(2H, t, J=5.8 Hz), 4.34(2H, t, J=5.8 Hz), 6.98(2H, d, J=8.9 Hz), 8.04(2H, d, J=8.9 Hz).

IR (Nujol): 3175, 2716, 2660, 1741, 1686, 1603, 1574cm$^{-1}$.

Elementary Analysis for $C_{32}H_{36}O_{1}0$:

Calcd: C, 66.20;H, 6.25.

Found: C, 66.24;H, 6.37.

EXAMPLE 33

4-{4-[3-(2-Fluorophenoxy)propoxy]-2-methoxy-3,5,6-trimethylbenzoyloxy}-2-methoxy-3,5,6-trimethylbenzoic Acid (88)

Melting point 150°–151° C.

$^1$H NMR ($CDCl_3$): δ2.19(3H, s), 2.24(3H, s), 2.25(3H, s), 2.29(3H, s), 2.36(6H, s), 2.30–2.41 (2H, m), 3.81(3H, s), 3.87(3H, s), 3.98(2H, t, J=6.0 Hz), 4.34(2H, t, J=6.0 Hz), 6.88–7.18(4H, m).

IR ($CHCl_3$): 1733, 1700(sh), 1600, 1565 cm$^{-1}$.

Elementary Analysis for $C_{31}H_{35}FO_8$:

Calcd: C, 67.14;H, 6.36;F, 3.43.

Found: C, 66.91;H, 6.42;F, 3.41.

EXAMPLE 34

4-{4-[3-(3-Fluorophenoxy)propoxy]-2-methoxy-3,5,6-trimethylbenzoyloxy}-2-methoxy-3,5,6-trimethylbenzoic Acid (89)

Melting point 163°–166° C.

$^1$H NMR ($CDCl_3$): δ2.19(3H, s), 2.24(3H, s), 2.25(3H, s), 2.28(3H, s), 2.35(6H, s), 2.28–2.34(2H, m), 3.80(3H, s), 3.86(3H, s), 3.95(2H, t, J=6.0 Hz), 4.25(2H, t, J=6.0 Hz), 6.63–6.76(3H, m), 7.19–7.31(1H, m).

IR ($CHCl_3$): 1732, 1705(sh), 1610, 1591 cm$^{-1}$.

Elementary Analysis for $C_{31}H_{35}FO_8$:

Calcd: C, 67.14;H, 6.36;F, 3.43.

Found: C, 66.86;H, 6.48;F, 3.41.

EXAMPLE 35

4-{4-[3-(4-Fluorophenylsulfanyl)propoxy]2-methoxy-3,5,6-trimethylbenzoyloxy}2-methoxy-3,5,6-trimethylbenzoic Acid (90)

The same reaction was conducted using thiophenol instead of phenol to give the sulfanyl compound.

Melting point 123°–125° C.

$^1$H NMR ($CDCl_3$): δ2.05–2.18(2H, m), 2.20(3H, s), 2.26(6H, s), 2.29(3H, s), 2.36(6H, s), 3.16(2H, t, J=7.2 Hz), 3.81(3H, s), 3.87(3H, s), 3.83–3.90(2H, m), 6.98–7.07(2H, m), 7.36–7.43(2H, m).

IR ($CHCl_3$): 3475, 1732, 1700(sh), 1588, 1574 cm$^{-1}$.

Elementary Analysis for $C_{31}H_{35}FO_7S$:

Calcd: C, 65.25;H, 6.18;F, 3.33;S, 5.62.

Found: C, 65.10;H, 6.27;F, 3.52;S, 5.42.

EXAMPLE 36

4-{4-[3-(4-Fluorobenzenesulfonyl)propoxy]-2-methoxy-3,5,6-trimethylbenzoyloxy}-2-methoxy-3,5,6-trimethylbenzoic Acid (91)

The sulfanyl compound (1.495 g, 6 mmol) obtained in Example 35 was dissolved in 20 ml of dichloromethane-ether (3:1), and to the solution was added MCPBA (m-Chloroperbenzoic, 85%, 3.7 g, 18 mmol) at room temperature with stirring so as to conduct oxidation, providing sulfonyl compound. The compound was reacted similarly to the above to give sulfonyl compound 91.

Melting point 170°–176° C.

$^1$H NMR ($CDCl_3$): δ2.15(3H, s), 2.21(3H, s), 2.24(3H, s), 2.28(3H, s), 2.35(6H, s), 2.19–2.30(2H, m), 3.40–3.47(2H, m), 3.80(3H, s), 3.86(3H, s), 3.80–3.90(2H, m), 7.25–7.34(2H, m), 7.96–8.03(2H, m).

IR ($CHCl_3$): 3475, 1732, 1700(sh), 1591 cm$^{-1}$.

Elementary Analysis for $C_{31}H_{35}FO_9S$:

Calcd: C, 61.78;H, 5.85;F, 3.15;S, 5.32.

Found: C, 62.01;H, 6.01;F, 3.40;S, 5.36.

EXAMPLE 37

4-{4-[3-(2,3-Difluorophenoxy)propoxy]-2-methoxy-3,5,6-trimethylbenzoyloxy}-2-methoxy-3,5,6-trimethylbenzoic Acid (92)

Melting point 190°–1 91° C.

$^1$H NMR ($CDCl_3$): δ2.19(3H, s), 2.24(3H, s), 2.25(3H, s), 2.29(3H, s), 2.35(6H, s), 2.24–2.41(2H, m), 3.a1(3H, s), 3.86(3H, s), 3.98(2H, t, J=5.8 Hz), 4.36(2H, t, J=5.8 Hz), 6.73–7.07(3H, m).

IR ($CHCl_3$): 1732, 1700(sh), 1610, 1565 cm$^{-1}$.

Elementary Analysis for $C_{31}H_{34}F_2O_8$:

Calcd: C, 65.03;H, 5.98;F, 6.64.

Found: C, 64.97;H, 6.04;F, 6.74.

EXAMPLE 38

4-{4-[3-(2,6-Difluorophenoxy)propoxy]-2-methoxy-3,5,6-trimethylbenzoyloxy}-2-methoxy-3,5,6-trimethylbenzoic Acid (93)

Melting point 107°–113° C.

$^1$H NMR ($CDCl_3$): δ2.20–2.33(2H, m), 2.22(3H, s), 2.26(3H, s), 2.28(3H, s), 2.29(3H, s), 2.36(6H, s), 3.81(3H, s), 3.86(3H, s), 3.99(2H, t, J=6.2 Hz), 4.42(2H, t, J=6.2 Hz), 6.86–7.06(3H, m).

IR ($CHCl_3$): 3475, 3350, 1732, 1703, 1574 cm$^{-1}$.

Elementary Analysis for $C_{31}H_{34}F_2O_8$:

Calcd: C, 65.03;H, 5.98;F, 6.64.

Found: C, 64.95;H, 6.05;F, 6.62.

EXAMPLE 39

4-{4-[3-(2-Methoxyphenoxy)propoxy]-2-methoxy-3,5,6-trimethylbenzoyloxy}-2-methoxy-3,5,6-trimethylbenzoic Acid (94)

Melting point 130°–131° C.

$^1$H NMR ($CDCl_3$): δ2.19(3H, s), 2.25(6H, s), 2.28(3H, s), 2.35(6H, s), 2.19–2.44(2H, m), 3.80(3H, s), 3.86(3H, s), 3.87(3H, s), 3.98(2H, t, J=5.9 Hz), 4.32(2H, t, J=6.2 Hz), 6.93–7.04(4H, m).

IR ($CHCl_3$): 1732, 1700(sh), 1590, 1570 $cm^{-1}$.

Elementary Analysis for $C_{32}H_{38}O_9$•0.2AcOEt:

Calcd: C, 67.43;H, 6.83.

Found: C, 67.48;H, 6.79.

EXAMPLE 40

4-{4-[3-(2, 6-Dimethoxyphenoxy)propoxy]-2-methoxy-3,5,6-trimethylbenzoyloxy}-2-methoxy-3,5,6-trimethylbenzoic Acid (95)

Melting point 155°–158° C.

$^1$H NMR($CDCl_3$): δ2.23(3H, s), 2.25(3H, s), 2.28(6H, s), 2.34(3H, s), 2.36(3H, s), 2.20–2.33(2H, m), 3.81 (3H, s), 3.85(9H, s), 4.01(2H, t, J=6.1 Hz), 4.24(2H, t, J=6.1 Hz), 6.59(2H, d, J=8.4), 7.00(1H, t, J=8.4).

IR ($CHCl_3$): 1732, 1700(sh), 1594 $cm^{-1}$.

Elementary Analysis for $C_{33}H_{40}O_{10}$:

Calcd: C, 66.43;H, 6.76.

Found: C, 66.64;H, 7.04.

EXAMPLE 41

4-{4-[3-(3, 5-Dimethoxyphenoxy)propoxy]-2-methoxy-3,5,6-trimethylbenzoyloxy}-2-methoxy-3,5,6-trimethylbenzoic Acid (96)

Melting point 112°–114° C.

$^1$H NMR ($CDCl_3$): δ2.19(3H, s), 2.24(6H, s), 2.28(3H, s), 2.34(3H, s), 2.35(3H, s), 2.19–2.35(2H, m), 3.78(6H, s), 3.80(3H, s), 3.86(3H, s), 3.94(2H, t, J=5.8 Hz), 4.22(2H, t, J=5.8 Hz), 6.13(2H, s), 7.18–7. 30(1H, m), 8.82(1H, bs).

IR ($CHCl_3$): 1732, 1700(sh), 1599 $cm^{-1}$.

Elementary Analysis for $C_{33}H_{40}O_{10}$:

Calcd: C, 66.43;H, 6.76.

Found: C, 66.23;H, 6.76.

EXAMPLE 42

4-{4-[3-(4-Carbamoylphenoxy)propoxy]-2-methoxy-3,5,6-trimethylbenzoyloxy}-2-methoxy-3,5,6-trimethylbenzoic Acid (97)

Melting point 235°–240° C.

$^1$H NMR ($CDCl_3$+$CD_3OD$): δ2.18(3H, s), 2.22(3H, s), 2.23(3H, s), 2.25(3H, s), 2.28(3H, s), 2.34(3H, s), 2.18–2.40(2H, m), 3.80(3H, s), 3.82(3H, s), 3.96(2H, t, J=5.8 Hz), 4.33(2H, t, J=5.8 Hz), 6.99(2H, d, J=8.8 Hz), 7.82(2H, d, J=8.8 Hz).

IR ($CHCl_3$)3492, 3406, 3310, 2664, 2550, 1731, 1698, 1666, 1605, 1573 $cm^{-1}$.

Elementary Analysis for $C_{32}H_{37}NO_9$•0.9$H_2O$:

Calcd: C, 64.50;H, 6.56;N, 2.35.

Found: C, 64.54;H, 6.31 ;N, 2.44.

EXAMPLE 43

4-{4-[3-(4-Methoxycarbonylphenoxy)propoxy]-2-methoxy-3,5,6-trimethylbenzoyloxy}-2-methoxy-3,5,6 trimethylbenzoic Acid (98)

Melting point 165°–169° C.

$^1$H NMR ($CDCl_3$): δ2.18(3H, s), 2.23(3H, s), 2.25(3H, s), 2.28(3H, s), 2.35(6H, s), 2.18–2.35(2H, m), 3.80(3H, s), 3.86(3H, s), 3.90(3H, s), 3.96(2H, t, J=5.8 Hz), 4.33(2H, t, J=6.2 Hz), 6.97(2H, d, J=9.0 Hz), 8.02(2H, d, J=9.0 Hz).

IR ($CHCl_3$): 3676, 3572, 3490, 2586, 1720(sh), 1711, 1604, 1576 $cm^{-1}$.

Elementary Analysis for $C_{33}H_{38}O_{10}$:

Calcd: C, 66.65;H, 6.44.

Found: C, 66.62;H, 6.48.

EXAMPLES 44–47

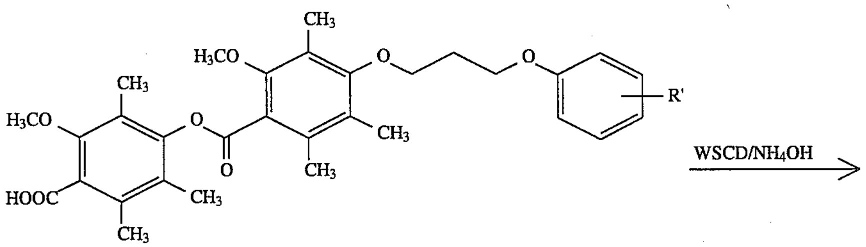

R' = 4-F 7
4-$CO_2H$ 87
4-$CO_2CH_3$ 98

E

-continued

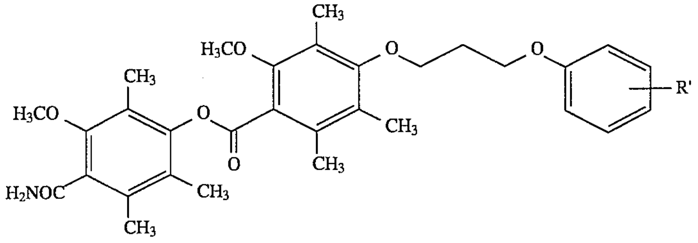

R' = 4-F 99
4-CONH2 100
4-CO2CH3 101
4-CO2H 102

1N-KOH/
DMSO

EXAMPLE 44

4-{4-[3-(4-Fluorophenoxy)propoxy]-2-methoxy-3,5,6-trimethylbenzoyloxy}-2-methoxy-3,5,6-trimethylbenzamide (99)

To a solution of benzoate derivative 7 (1.101 g, 2 mmol) obtained in Example 2 in 20 ml of DMF were added WSCD·HCl (water soluble carbodiimide hydrochloride=1-Ethyl-3-(3-dimethylaminopropyl)-carbodiimide, 422 mg, 2.2 mmol) and HOBt·$H_2O$ (1-hydroxybenzotriazole, 337 mg, 2.2 mmol) under ice cooling with stirring. The mixture was stirred for 1 hour at 0° C., and then aqueous $NH_4OH$ (28%, 1.4 ml, 10 mmol) was added thereto. The mixture was stirred at room temperature for 21 hours, then concentrated in vacuo, washed with water, extracted with ethyl acetate, washed with dilute hydrochloride, washed with water, dried over sodium sulfate, and concentrated. The residue was purified by chromatography on Lobar (B, $CHCl_3$:MeOH:$H_2O$=64:12:1) to give the crude compound (868 mg, 78%), which compound then was crystallized from dichloromethane/ether/hexane to give the title compound 99 (635 mg, 57%).

Melting point 146°–149° C.

$^1$H NMR($CDCl_3$): δ2.18(3H, s), 2.23(6H, s), 2.25(3H, s), 2.32(3H, s), 2.34(3H, s), 2.18–2.34(2H, m), 3.80(3H, s), 3.81(3H, s), 3.94(2H, t, J=6.0 Hz), 4.22(2H, t, J=6.0 Hz), 5.87(2H, s), 6.84–7.04(4H, .m).

IR ($CHCl_3$): 3506, 3390, 1732, 1672, 1585 $cm^{-1}$.

Elementary Analysis for $C_{31}H_{36}FNO_7$:

Calcd: C, 67.26;H, 6.55;F, 3.43;N, 2.53.

Found: C, 66.99;H, 6.59;F, 3.64;N, 2.54.

EXAMPLE 45

4-{4-[3-(4-Carbamoylphenoxy)propoxy]-2-methoxy-3,5,6-trimethylbenzoyloxy}-2-methoxy-3,5,6-trimethylbenzamide (100)

Compound 87 prepared in Example 32 was treated in the same manner as in Example 44 to give compound 100 (65%).

Melting point 284°–286° C.

$^1$HNMR(DMSO): δ2.15(9H, s), 2.18(6H, s), 2.26(3H, s), 2.15–2.26(2H, m), 3.71(6H, s), 3.92(2H, t, J=5.8 Hz), 4.30(2H, t, J=5.8 Hz), 7.03(2H, d, J=8.6 Hz), 7.19(1H, bs), 7.50(1H, bs), 7.76(2H, bs), 7.86(2H, d, J=8.6 Hz).

IR (Nujol): 3352, 3176, 1746, 1647, 1619, 1602, 1569 $cm^{-1}$.

Elementary Analysis for $C_{32}H_{38}N_2O_8$. 0.3$H_2O$:

Calcd: C, 65.81;H, 6.66;N, 4.80.

Found: C, 65.86;H, 6.51 ;N, 4.98.

EXAMPLE 46

4-{4-[3-(4-Methoxycarbonylphenoxy)propoxy]-2methoxy-3,5,6-trimethylbenzoyloxy}-2-methoxy-3,5,6 trimethylbenzamide (101)

Compound 98 prepared in Example 43 was treated in the same manner as in Example 44 to give compound 101 (73%).

Melting point 202°–204° C.

$^1$H NMR (DMSO): δ2.17(3H, s), 2.22(6H, s), 2.25(3H, s), 2.32(3H, s), 2.34(3H, s), 2.25–2.40(2H, m), 3.79(3H, s), 3.81(3H, s), 3.90(3H, s), 3.95(2H, t, J=5.8 Hz), 4.33(2H, t, J=6.2 Hz), 6.97(2H, d, J=9.0 Hz), 8.01 (2H, d, J=9.0 Hz).

IR ($CHCl_3$): 3508, 3390, 1720(sh), 1712, 1673, 1605, 1586 $cm^{-1}$.

Elementary Analysis for $C_{33}H_{39}NO_9$:

Calcd: C, 66.77;H, 6.62;N, 2.36.

Found: C, 66.86;H, 6.61 ;N, 2.39.

EXAMPLE 47

4-{4-[3-(4-Carboxyphenoxy)propoxy]-2-methoxy-3,5,6-trimethylbenzoyloxy}-2-methoxy-3,5,6-trimethylbenzamide (102)

To a solution of the amide-ester prepared in Example 46 (101, 694 mg, 1.17 mmol) in 30 ml of DMSO, was added 1N-KOH (3.5 ml, 3.5 mmol) with stirring, so that the amide-ester was subjected to hydrolysis to give 602 mg of the title compound 102 (89%).

Melting point 267°–268° C.

$^1$H NMR ($CDCl_3$+CD3OD): δ2.19(3H, s), 2.22(3H, s), 2.23(3H, s), 2.25(3H, s), 2.30(3H, s), 2.34(3H, s), 2.25–2.41(2H, m), 3.80(3H, s), 3.81(3H, s), 3.97(2H, t, J=6.0 Hz), 4.34(2H, t, J=5.7 Hz), 6.98(2H, d, J=8.7 Hz), 8.03(2H, d, J=9.3 Hz).

IR (Nujol): 3376, 3182, 2722, 2618, 2498, 1732, 1693, 1636, 1603, 1578 $cm^{-1}$.

Elementary Analysis for $C_{32}H_{37}NO_9$.0.3$H_2O$:

Calcd: C, 65.70;H, 6.48;N, 2.39.

Found: C, 65.72;H, 6.41;N, 2.53.

EXAMPLES 48–50
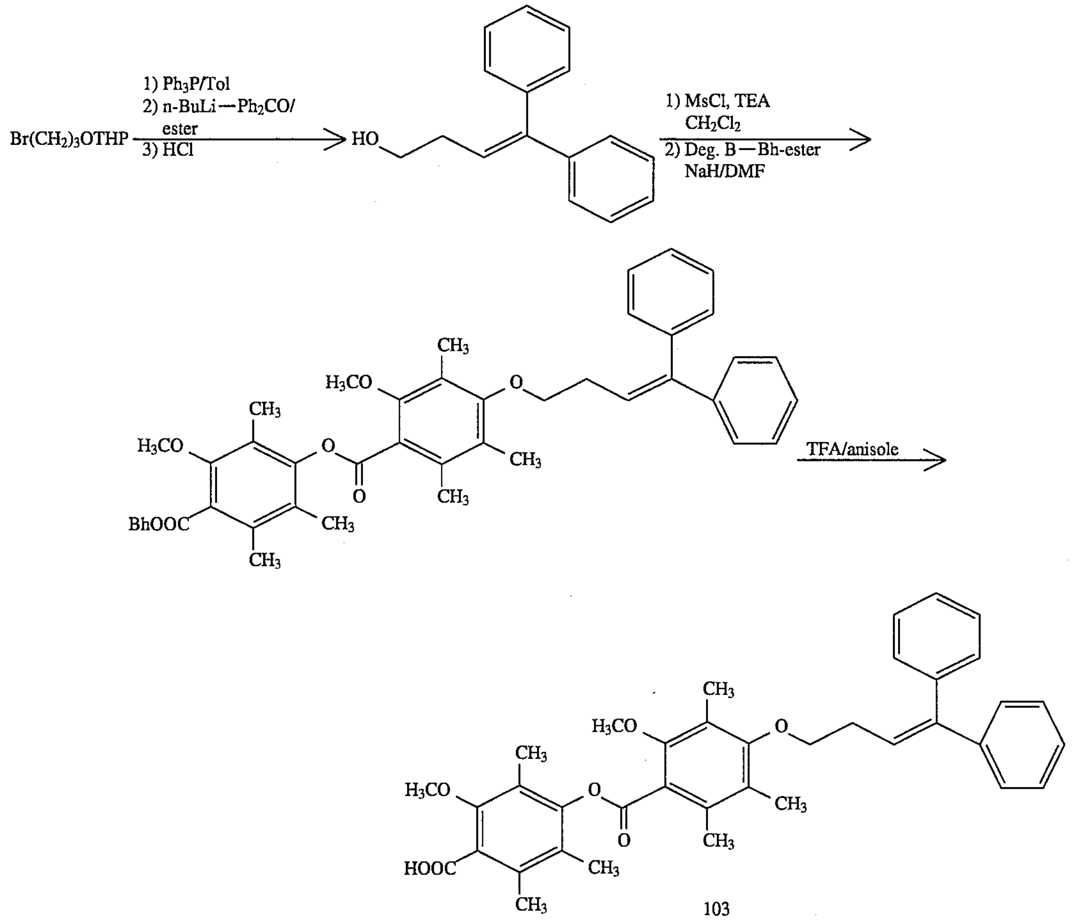
103
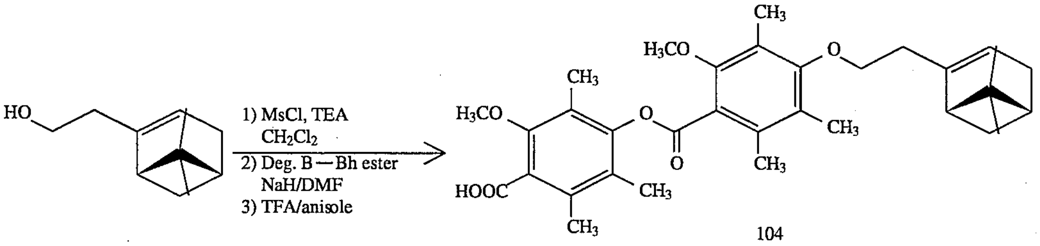
104
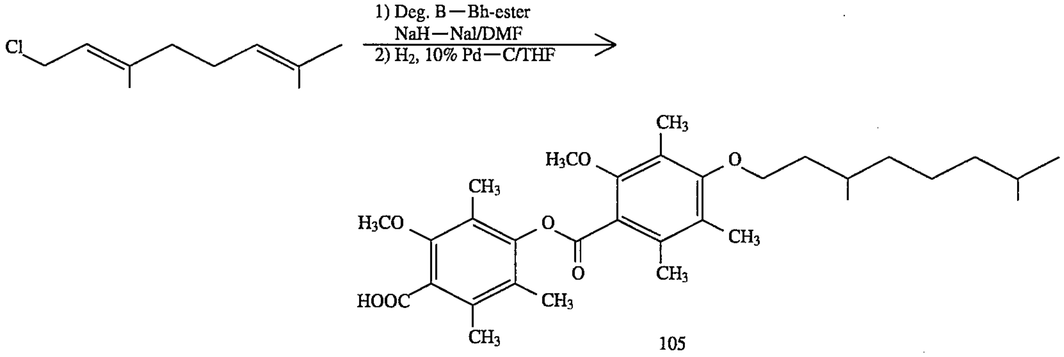
105

EXAMPLE 48

4-[4-(4,4-Diphenylbut-3-enyloxy)-2-methoxy-3,5,6-trimethylbenzoyloxy]-2-methoxy-3,5,6-trimethylbenzoic Acid (103)

i) 1-Bromopropanol (10 g, 71.9 mmol) was reacted with 2,3-dihydropyrane (19.7 ml, 215.7 mmol) in the presence of p-TsOH·$H_2O$ in THF at room temperature with stirring, to give 12.45 g of γ-bromopropyl tetrahydropyranyl-2-ether (78%).

ii) γ-Bromopropyl tetrahydropyranyl-2-ether obtained above (2.23 g, 10 mmol) was dissolved in 13 ml of THF, and to the solution was added 2.62 g of triphenylphosphine (10 mmol). The mixture was heated under reflux in nitrogen gas for 31 hours (Litt. F. Bohlmann, H. Bornowski und P. Herbst Chem. Ber., 93 1931–1937(1960)). The precipitated crystals were removed by filtration, and washed with ether to give 2.904 g of γ-bromotriphenylphosphonium propylalcohol (72%). Melting point 234°–236° C. To a suspension of 889 mg of the resultant phosphonium salt (2.2 mmol) in 25 ml of ether was added n-BuLi (1.64 mol/l Hexane 2.8 ml=4.65 mmol), and the mixture was stirred at room temperature for 1 hour. Benzophenone (404 mg, 2.2 mmol) was added thereto, and the mixture was stirred at room temperature for 3.5 hours. The mixture was poured into dilute hydrochloride, extracted with ethyl acetate, washed with water, dried over sodium sulfate, and concentrated. The residue was purified by flash chromatography on silica gel using toluene-ethyl acetate (9:1) as eluent, to give 285 mg of 4, 4-diphenylbut-3-enylpropyl alcohol (57%). The alcohol (720 mg, 3.21 mmol) was dissolved in 10 ml of dry $CH_2Cl_2$, and the mixture was stirred under ice cooling. To the mixture were added $Et_3N$ (1.34 ml, 9.63 mmol) and MsCl (373 μl, 4.82 mmol), and the resultant mixture was stirred at room temperature for 1 hour. The mixture was poured into water, extracted with $CH_2Cl_2$, washed with water, dried over sodium sulfate, and concentrated to give 914 mg of mesylate (94%). The mesylate was coupled with Deg. B-Bh-Ester by the NaH/DMF method described in Example 23, and then the resultant compound was subjected to deprotection to remove the Bh group by TFA/Anisole method according to a conventional method. This gives the title compound 103 as powders (10% over all).

$^1$H NMR ($CDCl_3$): δ2.19(3H, s), 2.24(3H, s), 2.25(3H, s), 2.29(3H, s), 2.35(6H, s), 2.65(2H, q, J=6.9 Hz), 3.80–3.91(2H, m)+3.80(3H, s), 3.86(3H, s), 6.19(1H, t, J=7.5 Hz), 7.23–7.46(10H, m).

IR ($CHCl_3$): 3676, 3604, 3488, 1731 $cm^{-1}$.

EXAMPLE 49

4-{4-[2-(6, 6-Dimetheylbicyclo[3.1.1]hept-2-en-2-yl)ethoxy]-2-methoxy-3,5,6-trimethylbenzoyloxy}-2-methoxy-3,5,6-trimethylbenzoic Acid (104)

(1R)-(-)-Nopol which is commercially available was converted to mesylate by the MsCl-$Et_3N$/$CH_2Cl_2$ method described in Example 48, and the mesylate was coupled with Deg. B-Bh-Ester by the NaH-NaI/DMF method described in Example 23. The resultant compound was subjected to deprotection to remove the Bh group by TFA/Anisole method according to a conventional method to give the title compound 104 as powders (59% over all).

$^1$H NMR ($CDCl_3$): δ0.85–1.30(2H, m), 1.56(3H, s), 1.57(3H, s), 1.66–2.30(4H, m), 2.21(3H, s), 2.25(3H, s), 2.26(3H, s), 2.28(3H, s), 2.35(6H, s), 2.46–2.53(2H, m), 3.74–3.89(2H, m), 3.81(3H, s), 3.85(3H, s), 5.56(1H, bs).

IR ($CHCl_3$): 3674, 3574, 3486, 1772, 1732 $cm^{-1}$.

EXAMPLE 50

4-[4-(3, 7-Dimethyloctyloxy)-2-methoxy-3,5,6-trimethylbenzoyloxy]-2-methoxy-3, 5,6-trimethylbenzoic Acid 105)

Geranyl chloride and Deg. B-Bh-Ester were coupled with each other by the NaH-NaI/DMF method described in Example 23. Then, the resultant compound was subjected to deprotection to remove the Bh group, and simultaneously, to reduction of the double bond using $H_2$/10% Pd-G/THF method according to a conventional method, to give the title compound 105 (52% over all).

Melting point 145°–148° C.

$^1$H NMR($CDCl_3$): δ0.88(6H, d, J=6.4 Hz), 0.97(3H, d, J=6.4 Hz), 1.13–1.95(8H, m), 2.19–2.39(2H, m), 2.21(3H, s), 2.23(3H, s), 2.26(6H, s), 2.31(3H, s), 2.34(3H, s)3.75–3.86(2H, m), 3.80(3H, s), 3.82(3H, s), 5.00(H, bs).

IR ($CHCl_3$): 3382, 1740, 1700, 1620, 1600 $cm^{-1}$.

Elementary Analysis for $C_{32}H_{46}O_7.H_2O$:

Calcd: C, 69.66;H, 8.59.

Found: C, 69.94;H, 8.39.

EXAMPLES 51–54

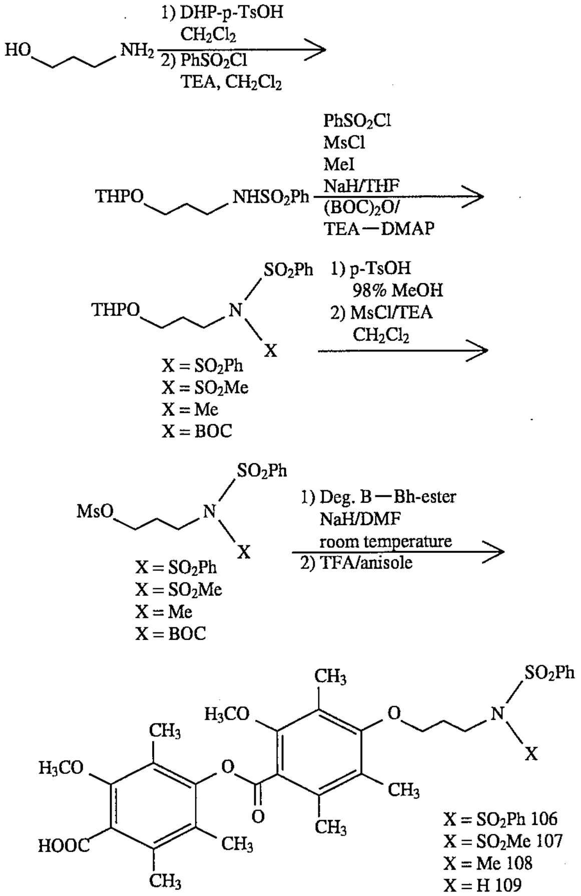

X = $SO_2Ph$ 106
X = $SO_2Me$ 107
X = Me 108
X = H 109

3-Amino-1-propanol (3.756 g, 50 mmol) was dissolved in dry dichloromethan, and 3, 4-dihydro-2H-pyran (6.8 ml, 75 mmol) and p-TsOH·$H_2O$ (10.45 g, 55 mmol) were added thereto. The mixture was stirred at room temperature for 69 hours, neutralized with 2N-NaOH (27.5 ml, 55 mol), portioned, extracted with dichloromethane, washed with water, dried over sodium sulfate, and concentrated to give 7.701 g (97%) of crude residue (THP-3-Aminopropionate ).

The resultant THP-3-Aminopropionate (3.184 g, 20 mmol) was dissolved in 30 ml of dry dichloromethane, and triethylamine (14 ml, 0.1 mol) and benzenesulfonyl chloride (5.1 ml, 0.04 mol) were added thereto under ice cooling with stirring. The mixture was stirred at room temperature for 15 hours, poured into water, extracted with dichloromethane, washed with water, dried over sodium sulfate, and concentrated. The residue was purified by flash chromatography on silica gel to give 1.80 g (30%) of THP-3-phenylsulfonylaminopropionate.

Then, 1.76 g (5.9 mmol) of the propionate was dissolved in THF (15 ml), and Nail (60% in oil, 274 mg, 6.17 mmol) was added thereto. The mixture was stirred at room temperature for 0.5 hours, and cooled. To the mixture was added benzenesulfonyl chloride (0.9 ml, 7.06 mmol)/THF (15 ml), and the resultant mixture was stirred at room temperature for 2.5 hours, poured into ice water, extracted with ethyl acetate, washed with water, dried over sodium sulfate, and concentrated. The residue was purified by flash chromatography on silica gel to give 2.36 g (91%) of THP-3-bisphenylsulfonylaminopropionate. The compound was subjected to deprotection to remove THP by p-TsOH/98% MeOH, and the resultant compound was mesylated using MsCl-$Et_3N$/$CH_2Cl_2$ to give mesyl-3-bisphenylsulfonylaminopropionate. Similarly, the deprotected propionate was reacted with either MsCl or MeI to give mesyl-3-Methylsulfonylphenylsulfonylamino-propionate, or Mesyl-3-Methylphenylsulfonylaminopropionate.

To a solution of THP-3-Phenylsulfonylaminopropionate (1.1 g, 3.67 mmol) in dioxane (5 ml) were added triethylamine (0.56 ml, 4.14 mmol), $(BOC)_2O$ (1.2 g, 5.5 mmol), and DMAP (45 mg, 0.37 mmol) at room temperature with stirring. The mixture was stirred at room temperature for 3 hours, poured into ice water, extracted with dichlorometahen, washed with water, dried over sodium sulfate, and concentrated. The residue was purified by flash chromatography on silica gel to give 1.203 g (82%) of THP-3-BOC-phenylsulfonylaminopropionate. Then, the compound was subjected to deprotection to remove the THP, and resultant compound was mesylated to give Mesyl-3-BOC-phenylsulfonylaminopropionate. Each mesylate was coupled with Deg. B-Bh-Ester by NaH/DMF method described above, and the compound was subjected to deprotection to remove the Bh group by the TFA/Anisole method described above, providing each title compound.

EXAMPLE 51

4-{4-[(3-Bisphenylsulfonylamino)propoxy]-2-methoxy-3,5,6-trimethylbenzoyloxy}-2-methoxy-3,5,6-trimethylbenzoic Acid (106)

Melting point 189°–190° C.

$^1$H NMR ($CDCl_3$): δ2.15(3H, s), 2.20(3H, s), 2.25(3H, s), 2.29(3H, s), 2.35(6H, s), 3.71–3.91(2H, m), 3.80(3H, s), 3.86(3H, s), 3.99–4.07(2H, m), 7.54–7.74(6H, m), 8.05–8.10(4H, m).

IR ($CHCl_3$): 3674, 3572, 3488, 1733, 1710(sh), 1573 $cm^{-1}$.

Elementary Analysis for $C_{37}H_{41}NO_{11}S_2$.0.4$Et_2O$:

Calcd: C, 60.25;H, 5.89;N, 1.82;S, 8.33

Found: C, 60.60;H, 5.63;N, 1.84;S, 8.17.

EXAMPLE 52

4-{4-[(3-Methylsulfonylphenylsulfonylamino)propoxy]-2-methoxy-3,5,6-trimethylbenzoyloxy}-2-methoxy-3,5,6-trimethylbenzoic acid (107)

Melting point 158°–162° C.

$^1$H NMR ($CDCl_3$): δ2.16(3H, s), 2.21(6H, s), 2.24(3H, s), 2.28(3H, s), 2.33(3H, s), 2.16–2.33(2H, m), 3.46(3H, s), 3.73–3.78(2H, m), 3.78(6H, m), 4.00(2H, t, J=7.4 Hz), 7.53–7.73(3H, m), 8.05–8.10(2H, m).

IR ($CHCl_3$): 1734, 1710(sh), 1600(sh), 1574 $cm^{-1}$.

Elementary Analysis for $C_{32}H_{39}NO_{11}$ $_{S2}$.$H_2O$:

Calcd: C, 53.84;H, 6.07;N, 1.96;S, 8.98

Found: C, 53.36;H, 5.51;N, 1.94;S, 8.11

EXAMPLE 53

4-{4-[(3-Methylphenylsulfonylamino)propoxy]-2-methoxy-3,5,6-trimethylbenzoyloxy}-2-methoxy-3,5,6-trimethylbenzoic Acid (108)

$^1$H NMR ($CDCl_3$): δ2.09(2H, t, J=7.2 Hz), 2.21(3H, s), 2.25(6H, s), 2.29(3H, s), 2.36(6H, s), 2.82(3H, s), 3.29(2H, t, J=7.2 Hz), 3.75–3.90(2H, m), 3.81(3H, s), 3.86(3H, s), 7.50–7.66(3H, m), 7.80–7.85(2H, m), 7.54–7.68(3H, m), 8.05–8.10(2H, m).

IR ($CHCl_3$): 1732, 1700(sh), 1600(sh), 1570 $cm^{-1}$.

Elementary Analysis for $C_{32}H_{39}NO_9S{\cdot}0.2C_6H_6$:

Calcd: C, 63.36;H, 6.44;N, 2.23;S, 5.09

Found: C, 63.33;H, 6.44;N, 2.17;S, 4.85.

EXAMPLE 54

4-{4-[(3-Phenylsulfonylamino)propoxy]-2-methoxy-3,5,6-trimethylbenzoyloxy}-2-methoxy-3,5,6-trimethylbenzoic Acid (109)

Foam $^1$H NMR ($CDCl_3$): δ2.00(2H, t, J=6.0 Hz), 2.12(3H, s), 2.17(3H, s), 2.24(3H, s), 2.28(3H, s), 2.34(6H, s), 3.26–3.35(2H, m), 3.76–3.81(2H, m), 3.79(3H, s), 3.86(3H, s), 5.12(1H, t, J=6.0 Hz), 7.53–7.68(3H, m), 7.90–7.94(2H, m).

IR ($CHCl_3$): 3490, 3360, 2586, 1732, 1710(sh), 1573 $cm^{-1}$.

Elementary Analysis for $C_{31}H_{37}NO_9S{\cdot}0.7H_2O$:

Calcd: C, 60.81;H, 6.32;N, 2.29;S, 5.24

Found: C, 60.79;H, 6.28;N, 2.39;S, 5.13.

EXAMPLES 55-63

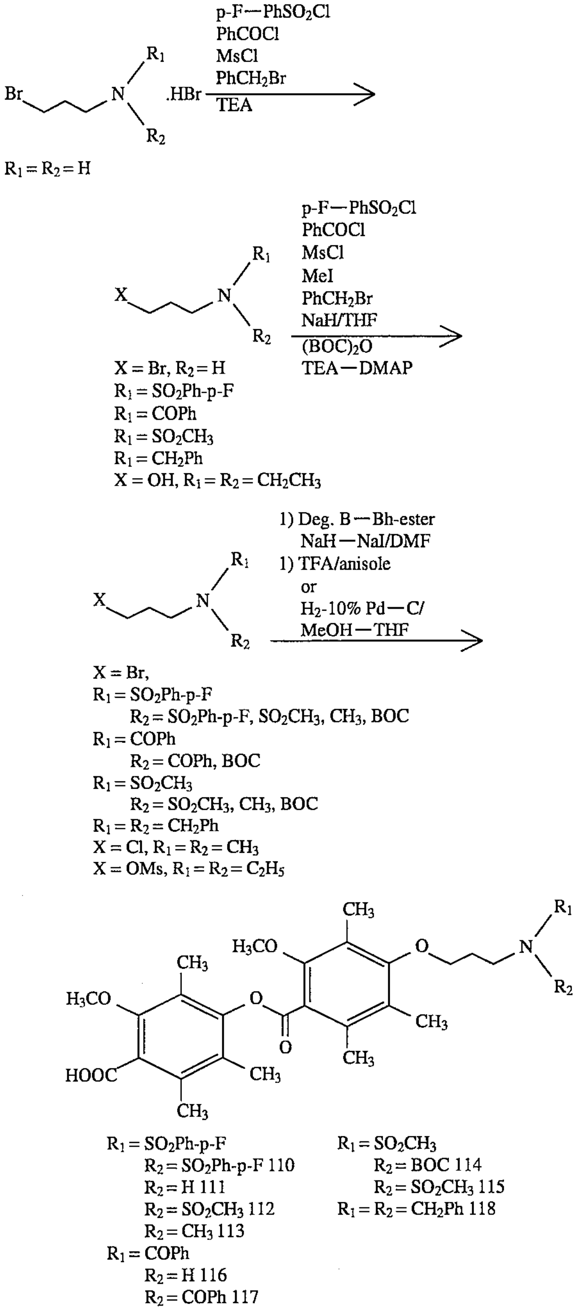

Synthesis of compounds 110, 111, 112, 113, 114, and 115

3-Bromopropylamine hydrochloride was reacted with p-fluorobenzenesulfonyl chloride and mesylchloride in the same manner as in Examples 51–54 to give monosulfonyl compound. Subsequently, the compound was reacted with p-fluorobenzenesulfonyl chloride, mesylchloride, methyliodide, or $(BOC)_2O$ to give the desired sulfonyl compound. Each sulfonyl compound was coupled with Deg. B-Bh-Ester by the NaH/DMF method described in Example 23, and the compound was subjected to deprotection to remove the Bh group by the TFA/Anisole method described above or $H_2$/10% Pd-C/MeOH-THF (1:1) method, providing the respective desired compound.

EXAMPLE 55

4-{4-[3-bis(4-Fluorophenyl)sulfonylaminopropoxy]-2-methoxy-3,5,6-trimethylbenzoyloxy}-2-methoxy-3,5,6-trimethylbenzoic Acid (110)

Melting point 191°–194° C.

$^1$H NMR($CDCl_3$): δ2.16(3H, s), 2.21(3H, s), 2.25(3H, s), 2.29(3H, s), 2.35(6H, s), 2.15–2.29(2H, m), 3.74(2H, t, J=5.8 Hz), 3.81(3H, s), 3.86(3H, s), 4.02(2H, t, J=7.6 Hz), 7.23–7.31(4H, m), 8.08–8.15(4H, m).

IR ($CHCl_3$): 1733, 1700(sh), 1591 $cm^{-1}$.

Elementary Analysis for $C_{37}H_{39}F_2NO_{11}S_2$:

Calcd: C, 57.28;H, 5.07;N, 1.81;F, 4.90;S, 8.27

Found: C, 57.69;H, 5.20;N, 1.79;F, 4.96;S, 8.34.

EXAMPLE 56

4-{4-[3-(4-Fluorophenyl)sulfonylaminopropoxy]-2-methoxy-3,5,6-trimethylbenzoyloxy}-2-methoxy-3,5,6 trimethylbenzoic Acid (111)

Melting point 188°–190° C.

$^1$H NMR ($CDCl_3$): δ2.01(2H, t, J=6.8 Hz), 2.13(3H, s), 2.18(3H, s), 2.24(3H, s), 2.28(3H, s), 2.34(6H, s), 3.26–3.36(2H, bd), 3.76–3.83(2H, m), 3.79(3H, s), 3.85(3H, s), 5.22(1H, bs), 7.18–7.27(2H, m), 7.90–7.97(2H, m).

IR ($CHCl_3$): 3594, 3486, 3334, 1732, 1710(sh), 1592 $cm^{-1}$.

Elementary Analysis for $C_{31}H_{36}FNO_9S \cdot 0.6H_2O$:

Calcd: C, 59.24;H, 5.97;N, 2.23;F, 3.02;S, 5.10

Found: C, 59.16;H, 5.91;N, 2.28;F, 3.10;S, 5.17.

EXAMPLE 57

4-{4-[3-Methylsulfonyl-(4-fluorophenyl) sulfonylaminopropoxy]-2-methoxy-3,5,6-trimethylbenzoyloxy}-2-methoxy-3,5,6-trimethylbenzoic Acid (112)

Melting point 163°–165° C.

$^1$H NMR($CDCl_3$): δ2.18(3H, s), 2.23(3H, s), 2.25(3H, s), 2.28(3H, s), 2.35(6H, s), 2.18–2.35(2H, m), 3.45(3H, s), 3.75–3.83(2H, m), 3.81(3H, m), 3.86(3H, s), 3.99(2H, t, J=7.6 Hz), 7.21–7.29(2H, m), 8.07–8.14(2H, m).

IR ($CHCl_3$): 1732, 1700(sh), 1591 $cm^{-1}$.

Elementary Analysis for $C_{32}H_{38}FNO_{11}S_2 \cdot 0.3H_2O$:

Calcd: C, 54.81;H, 5.55;N, 2.00;S, 9.15;F, 2.71

Found: C, 54.93;H, 5.84;N, 2.02;S, 8.70;F, 2.61.

EXAMPLE 58

4-{4-[3-Methyl-(4-fluorophenyl) sulfonylaminopropoxy]-2-methoxy-3,5,6-trimethylbenzoyloxy}-2-methoxy-3,5,6-trimethylbenzoic Acid (113)

Melting point 142°–144° C.

$^1$H NMR ($CDCl_3$): δ2.03–2.16(2H, m), 2.21(3H, s), 2.25(3H, s), 2.26(3H, s), 2.28(3H, s), 2.35(6H, s), 2.81(3H, s), 3.29(2H, t, J=6.8 Hz), 3.78–3.83(2H, m), 3.81(3H, s), 3.85(3H, s), 7.19–7.28(2H, m), 7.81–7.88(2H, m).

IR ($CHCl_3$): 1732, 1700(sh), 1592 $cm^{-1}$.

Elementary Analysis for $C_{32}H_{38}FNO_9S$:

Calcd: C, 60.84;H, 6.06;N, 2.22;S, 5.08;F, 3.01

Found: C, 60.95;H, 6.14;N, 2.23;S, 5.30;F, 3.19.

EXAMPLE 59

4-[4-(3-t-Butoxycarbonylmethylsulfonylaminopropoxy)-2-methoxy-3,5,6-trimethylbenzoyloxy]-2-methoxy-3,5,6-trimethylbenzoic Acid (114)

Melting point 156°–158° C.

$^1$H NMR ($CDCl_3$): δ1.57(9H, s), 2.20(3H, s), 2.25(3H, s), 2.26(3H, s), 2.28(3H, s), 2.35(6H, s), 2.15–2.28(2H, m), 3.32(3H, s), 3.78–3.86(2H, m) , 3.80(3H, s), 3.86(3H, s), 3.97(2H, t, J=7.2 Hz).

IR ($CHCl_3$): 1727 $cm^{-1}$.

Elementary Analysis for $C_{31}H_{43}NO_{11}S$:

Calcd: C, 58.38;H, 6.80;N, 2.20;S, 5.03;

Found: C, 58.57;H, 6.86;N, 2.31;S, 4.86.

EXAMPLE 60

4-[4-(3-bis-Methylsulfonylaminopropoxy)-2-methoxy-3,5,6-trimethylbenzoyloxy]-2-methoxy-3,5,6-trimethylbenzoic Acid (115)

Melting point 197°–201° C.

$^1$H NMR ($CDCl_3$): δ2.21(3H, s), 2.25(3H, s), 2.26(3H, s), 2.28(3H, s), 2.36(6H, s), 2.32–2.39(2H, m), 3.35(6H, s), 3.81(3H, s), 3.86(3H, s), 3.81–3.84(2H, m), 4.06(2H, t, J=7.6 Hz).

IR ($CHCl_3$): 1734, 1700(sh)$cm^{-1}$.

Elementary Analysis for $C_{27}H_{37}NO_{11}$ $S_2 \cdot 0.8Et_2O$:

Calcd: C, 53.74;H, 6.72;N, 2.08;S, 9.50

Found: C, 53.99;H, 6.07;N, 1.81;S, 9.30.

Synthesis of compounds 116, 117 and 118

3-Bromopropylamine hydrochloride was reacted with benzoyl chloride in the same manner as described above to give monobenzoyl compound. Subsequently, the compound was similarly reacted with benzoyl chloride, or $(BOC)_2O$ to the desired benzoyl compound. Each benzoyl compound was coupled with Deg. B-Bh-Ester by the NaH/DMF method described above, and the resultant compound was subjected to deprotection to remove the Bh group by the TFA/Anisole method described above, providing the desired compound.

EXAMPLE 61

4-[4-(3-Benzoylaminopropoxy)-2-methoxy-3,5,6-trimethylbenzoyloxy}-2-methoxy-3,5,6-trimethylbenzoic Acid (116)

Melting point 140°–143° C.

$^1$H NMR ($CDCl_3$): δ2.15–2.26(2H, m), 2.19(3H, s), 2.20(3H, s), 2.23(3H, s), 2.26(6H, s), 2.34(3H, s), 3.73–3.83(2H, m), 3.79(6H, s), 3.91(2H, t, J=5.4 Hz), 6.22(1H, bs), 6.89(1H, t, J=5.0 Hz), 7.35–7.50(3H, m), 7.75–7.80(2H, m).

IR ($CHCl_3$): 3428, 2542, 1731, 1651, 1600, 1576 $cm^{-1}$.

Elementary Analysis for $C_{32}H_{37}NO_8 \cdot 1.2H_2O$:

Calcd: C, 65.67;H, 6.79;N, 2.39

Found: C, 65.74;H, 6.66;N, 2.43.

EXAMPLE 62

4-[4-(3-Dibenzoylaminopropoxy)-2-methoxy-3,5,6-trimethylbenzoyloxy}-2-methoxy-3,5,6-trimethylbenzoic Acid (117)

Melting point 203°–204° C.

$^1$H NMR ($CDCl_3$): δ2.20(3H, s), 2.22(3H, s), 2.25(6H, s), 2.30(3H, s), 2.34(3H, s), 2.20–2.40(2H, m), 3.79(3H, s), 3.81(3H, s), 3.92(2H, t, J=6.6 Hz), 4.34(2H, t, J=7.0 Hz), 6.09(1H, bs), 7.08–7.25(6H, m), 7.41–7.48(4H, m).

IR ($CHCl_3$): 1730, 1696, 1647, 1600, 1575 $cm^{-1}$.

Elementary Analysis for $C_{39}H_{41}NO_9$:

Calcd: C, 70.15;H, 6.19;N, 2.10

Found: C, 70.15;H, 6.34 ;N, 2.18.

EXAMPLE 63

4-{4-[3-(bis-Benzylamino)propoxy]-2-methoxy-3,5,6-trimethylbenzoyloxy}-2-methoxy-3,5,6-trimethylbenzoic Acid (118)

3-Bromopropylamine hydrochloride (2.19 g, 10 mmol) was dissolved in dry acetonitrile, and triethylamine (12.5 ml, 90 mmol) and benzyl bromide(4.8 ml, 40 mmol) were added thereto with stirring. The mixture was heated at 55° C. for 6 hours, and then, poured into ice water, extracted with ethyl acetate, washed with water, dried over sodium sulfate, and concentrated to give 1.41 g of the benzylamine as the crude residue (44%).

The benzylamine was amino-etherified with Deg. B-Bh-Ester according to NaH/DMF method (82%), and then, the resultant compound was subjected to deprotection to remove the Bh group by $H_2$/10% Pd-C/MeOH-THF (2:1) described above, providing 612 mg of the desired compound 118 (69%).

foam $^1$H NMR ($CDCl_3$): δ2.03–2.32(2H, m), 2.12(3H, s), 2.17(3H, s), 2.19(3H, s), 2.22(3H, s), 2.25(3H, s), 2.32(3H, s), 2.74(2H, t, J=6.6 Hz), 3.65–3.81(2H, m), 3.70(3H, s), 3.76(3H, s), 3.77(4H, s), 6.16(1H, bs), 7.25–7.41(10H, m).

IR ($CHCl_3$) 1731, 1700(sh)$cm^{-1}$.

Elementary Analysis for $C_{39}H_{45}NO_7 \cdot 1.8H_2O$:

Calcd: C, 69.68;H, 7.29;N, 2.08

Found: C, 69.73;H, 6.89;N, 2.37.

EXAMPLES 64 and 65

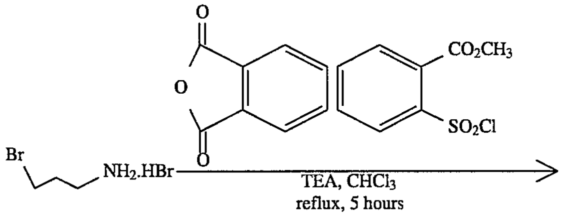

-continued

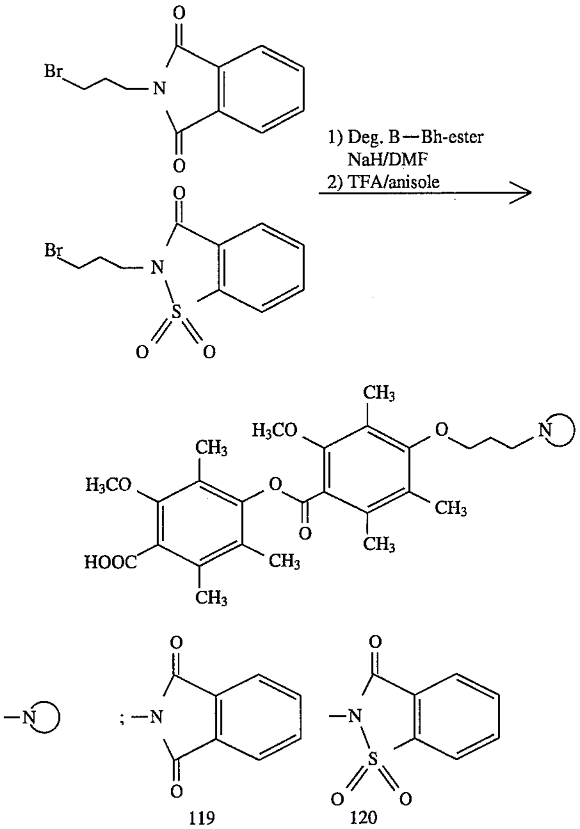

119 120

EXAMPLE 64

4-{4-[3-(1, 3-Dioxo-1, 3-dihydroisoindol-2-yl)-propoxy]-2-methoxy-3,5,6-trimethylbenzoyloxy}-2-methoxy-3,5,6-trimethylbenzoic Acid (119)

To a suspension of 3-Bromopropylamine hydrochloride (2.826 g, 13 mmol) in 130 ml of dry chloroform were added triethylamine (1.84 ml, 13.2 mmol), phthalic anhydride (2.103 g, 14.2 mmol), and 4A Molecular Sieves (5 g) with stirring, and the mixture was heated under reflux for 5 hours. The mixture was poured into ice water, extracted with dichloromethane, washed with dilute aqueous $NaHCO_3$ solution and then water, dried over sodium sulfate, and concentrated, to give 1.308 g of the crude residue (38%).

The resultant phthaloyl imide was coupled with Deg. B-Bh-Ester by the NaH/DMF method described in Example 23, and the compound was subjected to deprotection to remove the Bh group by the TFA/Anisole described above, providing the desired compound 119.

Melting point 197°–200° C.

$^1$H NMR ($CDCl_3$): δ2.21(3H, s), 2.25(3H, s), 2.26(3H, s), 2.28(3H, s), 2.35(6H, s), 2.18–2.31(2H, m), 3.80(3H, s), 3.86(3H, s), 3.81–3.88(2H, m), 3.92(2H, t, J=7.0 Hz), 7.71–7.90(4H, m).

IR ($CHCl_3$): 1769, 1720(sh), 1711, 1600(sh), 1570 $cm^{-1}$.

Elementary Analysis for $C_{33}H_{35}NO_9$:

Calcd: C, 67.22;H, 5.98;N, 2.38

Found: C, 66.85;H, 6.08;N, 2.23.

EXAMPLE 65

4-{4-[3-(1, 1 -Dihydroxy-3-oxo-3H-benzo[d]-isothiazole-2-yl) propoxy]-2-methoxy-3,5,6-trimethylbenzoyloxy}-2-methoxy-3,5,6-trimethylbenzoic Acid (120)

3-Bromopropylamine hydrochloride (2.189 g, 10 mmol) was suspended in 15 ml of dry dichloromethane, and to the suspension were added triethylamine (7 ml, 50 mmol) and methyl 2(chlorosulfonyl)benzoate (2.738 g, 10.5 mmol). The mixture was stirred at room temperature for 66 hours, poured into ice water, extracted with dichloromethane, washed with water, dried over sodium sulfate, and concentrated. The residue was purified by flash chromatography on silica gel to give 617 mg of 1,1-Dihydroxy-3-oxo-3H-benzo[d]isothiazole (20%). The isothiazole was etherified with Deg. B-Bh-Ester by the NaH/DMF method described above, and the compound was subjected to deprotection to remove the Bh group by the TFA/Anisole method described above, providing 309 mg of the desired compound 120 (97%).

Melting point 222°–223° C.

$^1$H NMR ($CDCl_3$): δ2.23(6H, s), 2.26(3H, s), 2.28(3H, s), 2.32(3H, s), 2.35(3H, s), 2.23–2.45(2H, m), 3.80(3H, s), 3.83(3H, s), 3.90(2H, t, J=6.0 Hz), 4.11 (2H, t, J=7.4 Hz), 5.15(1 H, bs), 7.84–8.11 (4H, m).

IR ($CHCl_3$): 3486, 1731, 1590, 1573 $cm^{-1}$.

Elementary Analysis for $C_{32}H_{35}NO_{10}S$:

Calcd: C, 61.43;H, 5.64;N, 2.24;S, 5.12

Found: C, 61.79;H, 5.73;N, 2.19;S, 4.79.

EXAMPLES 66–69

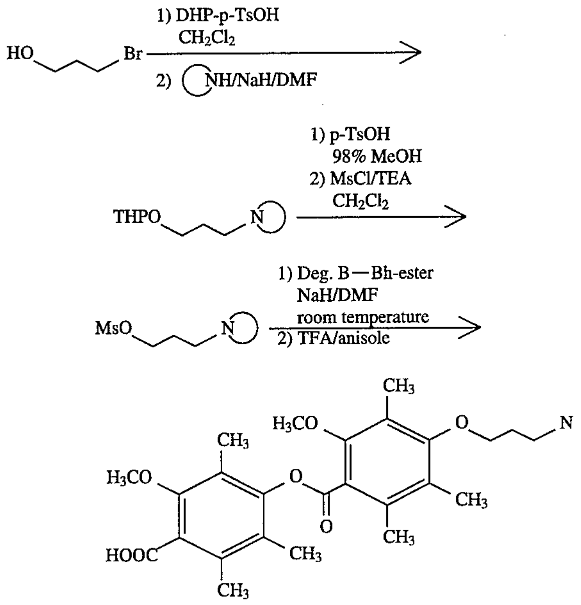

-continued

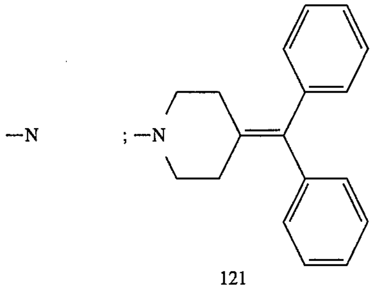

121

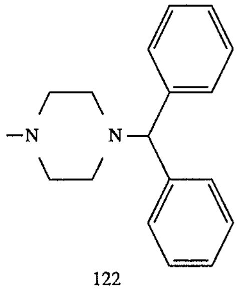

122

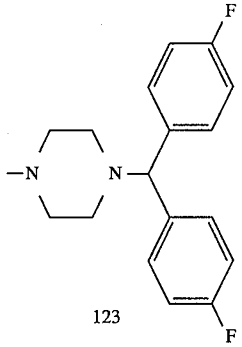

123

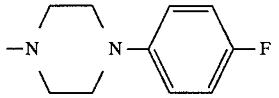

124

Synthesis of compounds of 121,122, 123 and 124

3-Bromopropanol was reacted with DHP (p-TsOH/$CH_2Cl_2$) in the same manner as in Example 48 to give the THP-protecting compound. Subsequently, the compound was reacted with either 4-benzhydrylidenepiperidine, 4-(bisphenylmethyl)piperidine, 4-[bis-(4-fluorophenyl)m-ethyl]piperidine, or 4-(4-Fluorophenyl)-piperazine according to the NaH/DMF method described in Example 23, and each compound was subjected to deprotection to remove the THPs by the p-TsOH/98% MeOH method described in Examples 51–54. Then, each compound was mesylated using MsCl/TEA/$CH_2Cl_2$ to give aminomesylate. The compound was amino-etherified with Deg. B-Bh-Ester by NaH/DMF descried above, and the resultant compound was subjected to deprotection to remove the Bh group by the TFA/Anisole method described above, providing the desired compound.

EXAMPLE 66

4-{4-[3-(4-Benzhydrylidenepiperidin-1-yl)-propoxy]-2-methoxy-3,5,6-trimethylbenzoyloxy}-2-methoxy-3,5,6- trimethylbenzoic Acid (121)

Melting point 153°–156° C.

$^1$H NMR ($CDCl_3$): δ2.16(6H, s), 2.21(6H, s), 2.25(3H, s), 2.30(3H, s), 2.16–2.35(2H, m), 2.72(4H, bs), 2.95(2H, t, J=14.6 Hz), 3.08(4H, bs), 3.74(3H, s), 3.78(3H, s), 3.50–3.78(2H, bm), 5.29(1H, bs), 7.10–7.33(10H, m).

IR ($CHCl_3$): 1731, 1670,–1595, 1573 $cm^{-1}$.

Elementary Analysis for $C_{43}H_{49}NO_7 \cdot 1.6H_2O$:

Calcd: C, 71.66;H, 7.30;N, 1.94

Found: C, 71.59;H, 6.88;N, 1.97.

EXAMPLE 67

4-{4-[3-(Di-Phenylmethylpiperazin-1-yl)propoxy]-2-methoxy-3,5,6-trimethylbenzoyloxy}-2-methoxy-3,5,6 -trimethylbenzoic Acid (122)

Melting point 161°–165° C.

$^1$H NMR ($CDCl_3$+$CD_3OD$): δ2.17(3H, s), 2.19(3H, s), 2.22(6H, s), 2.28(3H, s), 2.31(3H, s), 2.22–2.35(2H, m), 2.71(4H, bs), 2.98(2H, t, J=19.6 Hz), 3.13(4H, bs), 3.76(3H, s), 3.82(3H, s), 3.76–3.83(2H, m), 4.34(1H, s), 7.20–7.44(10H, m).

IR ($CHCl_3$): 1731, 1669, 1573 $cm^{-1}$.

Elementary Analysis for $C_{42}H_{50}N_2O_7 \cdot 2.1H_2O$:

Calcd: C, 68.85;H, 7.46;N, 3.82

Found: C, 68.57;H, 6.99;N, 3.69.

EXAMPLE 68

4-{4-[3-(Di-4-Fluorophenylmethylpiperazin-1-yl)-propoxy]-2-methoxy-3,5,6-trimethylbenzoyloxy}-2-methoxy-3,5,6 -trimethylbenzoic Acid (123)

Melting point 234°–238° C.(dec.)

$^1$H NMR ($CDCl_3$): δ2.14(3H, s), 2.20(6H, s), 2.23(3H, s), 2.28(3H, s), 2.33(3H, s), 2.14–2.29(2H, m), 2.63(2H, bs), 2.93(4H, bs)3.39(2H, bs), 3.63–3.85(4H, bs), 3.78(3H, s), 3.79(3H, s), 4.37(1H, s), 6.95–7.04(4H, m), 7.26–7.39(4H, m).

IR ($CHCl_3$): 3475, 1731, 1668, 1603, 1574 $cm^{-1}$.

Elementary Analysis for $C_{42}H_{48}F_2N_2O_7 \cdot CF_3CO_2H$:

Calcd: C, 62.55;H, 5.85;N, 3.32;F, 11.24

Found: C, 62.28;H, 5.83;N, 3.31 ;F, 11.28.

EXAMPLE 69

4-{4-[3-(4-(4-Fluorophenyl)piperazin-1-yl)propoxy]-2 -methoxy-3,5,6-trimethylbenzoyloxy}-2-methoxy-3,5,6-trimethylbenzoic Acid (124)

Melting point 137°–141° C.

$^1$H NMR (CDCl, sat): δ2.18(3H, s), 2.22(3H, s), 2.24(3H, s), 2.25(3H, s), 2.31(3H, s), 2.34(3H, s), 2.18–2.34(2H, m), 3.28–3.50(10H, m), 3.78–3.88(2H, m), 3.79(3H, s), 3.82(3H, s), 6.89–7.06(4H, m).

IR (Nujol): 3448, 2566, 1724, 1648, 1571 $cm^{-1}$.

Elementary Analysis for $C_{35}H_{43}FN_2O_7$:

Calcd: C, 67.51;H, 6.96;N, 4.50;F, 3.05
Found: C, 62.14;H, 6.72;N, 4.16;F, 5.51.

Effect of the Invention

Phospholipase $A_2$ ($PLA_2$), which is an inhibitory target of the compounds of the present invention specifically hydrolyzes the sn- 2 ester bond of glycerophospholipids to generate lysophospholipids and free fatty acids. The resulting changes in phospholipid integrity and toxic action of the forming free fatty acids and lysophospholipids may be crucial to the altered membrane properties. Further, productions of free fatty acids, arachidonic acids and lysophospholipids are considered to be the rate-limiting step in the generation of a lipidal inflammation transmitter, eicosanoid, and possibly platelet-activating factor.

This enzyme is widespread in nature and exists as both secretory and intracellular types.

Secretory $PLA_2$ of mammalian is classified in two types, namely pancreatic type (I group) and non-pancreatic type (II group). The pancreatic $PLA_2$ is an important enzyme existing richly in the digestive secretion of pancreas. On the other hand, non-pancreatic II type $PLA_2$ is found in inflammatory regions such as synovial fluid of inflammatory arthritic patients or the like, and considered to play an important role in various biological stages in inflammatory process. This enzyme may participate in the inflammatory process in various disorders such as rheumatoid arthritis, osteoarthritis, psoriasis, Gram-negative septic shock, adult respiratory distress syndrome, inflammatory bowel disease. There is substantial evidence which shows that this secretory $PLA_2$ significantly participates in pathogenesis of the inflammatory process. Accordingly, inhibition of secretory $PLA_2$ may become a useful therapeutic modality [Pruzansky W. & Vadas P., Immunol. Today, 12 (5), 143–146 (1991)].

On the other hand, intracellular $PLA_2$ (cytosolic $PLA_2$, $cPLA_2$) has been found in cytosol of various cells including platelets, macrophage, renal mesangial cells, monoblast and macrophage cell lines, kidney or the like. It is considered that $cPLA_2$ preferentially hydrolyzes phospholipids of which 2-position is esterified by arachidonic acid, and its enzymatic activity would be enhanced by translocation to membranes in response to various physiological stimulus in association with phosphorylation. Consequently, $cPLA_2$ is believed to be involved in a series of regulating reactions associated with various pathologic aspects via its ability to regulate the release of arachidonic acid, which is a forerunning stage for biosynthesizing eicosanoid [Clark J. D., Cell, 65, 1043–1051, 1991; Sharp J. D., J. Biol. Chem., 266 (23), 14850–14853 (1991)]. Accordingly, it is considered that any substance enabling to significantly inhibit intracellular $PLA_2$ would provide various therapeutic means.

Both secretory and intracellular type phospholipase $A_2$ inhibitory activity of the compounds of the present invention were examined according to the test methods described below.

Assays of Secretory $PLA_2$ Inhibitory Activity

Secretory $PLA_2$ activity was assayed according to the method described in Penynolds L. J., Hughes L. L., Dennis E. A. et al. Anal. Biochem. 201,190–197 (1992).

Diheptanoyl thiophosphatidylcholine which was prepared according to the procedure described in the literature was used as a substrate. Human secretory $PLA_2$ was used as an enzyme. The diheptanoyl thio PC (1 mM) was reacted with the human secretory $PLA_2$ in the presence of Triton X100 (0.3 mM) and 5,5'-dithiobis-(2-nitrobenzoic acid) (125 μM) in Tris buffer (25 mM, pH 7.3), $CaCl_2$ (10 mM), KCl (100 mM), bovine serum albumin (1.0 mg/ml), and then the change in absorbance at 405 nm at the time of 30 minutes after the reaction was assayed.

Inhibitory activity (%) was estimated by the formula: [(the change in absorbance with the inhibitor and $PLA_2$·the change in absorbance with the inhibitor and without $PLA_2$)/(the change in absorbance without the inhibitor and with $PLA_2$·the change in absorbance without the inhibitor and $PLA_2$)]×100.
IC50 value (μM) was calculated from graph showing inhibitory values on the vertical axis and log of concentrations of the inhibitor on the horizontal axis.

Results are shown in Table 1.

Assays of Intracellular $PLA_2$ Inhibitory Activity $cPLA_2$ activity was assayed according to the method described in R. M. Kramer, E. F. Roberts, J. Manetta and J. E. Putnam, J. Biol. Chem., 268 (8), 5268–5272 (1991). Briefly, intracellular $PLA_2$ activity was assayed using supersonic treated ribosomes which contain 1-palmitoyl-2-[$^{14}C$] arachidonyl-sn-glycero-3-phosphocholine and sn-1, 2-dioleoylglycerol at a molar ratio of 2:1. This test mixture contained 1 mM $CaCl_2$, 2 mM dithiothreitol, 150 mM NaCl, 50 mM Hepes, pH 7.4 and 0.1 mg/ml BSA. A substrate is a 2 μM radioisotope labelled phosphatidylcholine ribosome containing 1 μM dioleoylglycerol. $IC_{50}$ value is calculating in the same manner as in calculating it for secretory $PLA_2$ inhibitory activity.

Results are shown in Table 1.

TABLE 1

| Example No. | s-$PLA_2$ Inhibition [$IC_{50}$ (μM)] | c-$PLA_2$ Inhibition [$IC_{50}$ (μM)] |
|---|---|---|
| 1 | 21 | 20 |
| 2 | 18 | 9.0 |
| 3 | 32 | 3.0 |
| 4 | 27 | 7.4 |
| 5 | 47 | 4.0 |
| 6 | 9.0 | 12 |
| 7 | >50 | 0.54 |
| 8 | 22 | 31 |
| 9 | 45 | 33 |
| 10 | 13 | 13 |
| 11 | 14 | 4.8 |
| 12 | >50 | 2.0 |
| 13 | >50 | 1.9 |
| 14 | 14 | 9.4 |
| 16 | >50 | 2.6 |
| 17 | 12 | 14 |
| 18 | >50 | 19 |
| 19 | 16 | 1.8 |
| 20 | 11 | 35 |
| 21 | 15 | 1.4 |
| 22 | 42 | 4.3 |
| 23 | 9.4 | 4.0 |
| 24 | 12 | 2.8 |
| 25 | 4.6 | 13 |
| 26 | 15 | 2.6 |

TABLE 1-continued

| Example No. | s-$PLA_2$ Inhibition [$IC_{50}$ (μM)] | c-$PLA_2$ Inhibition [$IC_{50}$ (μM)] |
|---|---|---|
| 27 | 13 | 1.5 |
| 28 | 6.9 | 10 |
| 29 | 12 | 8.5 |
| 30 | 16 | 5.4 |
| 31 | 7.0 | 24 |
| 32 | 10 | 38 |
| 33 | 26 | 12 |
| 34 | 50 | 9.7 |
| 36 | 50 | >50 |
| 37 | 12 | 6.6 |
| 38 | 6.7 | 7.1 |
| 39 | 8.9 | 12 |
| 40 | 6.1 | 13 |
| 41 | 7.0 | 5.9 |
| 42 | 5.0 | 31 |
| 43 | 5.1 | 14 |
| 44 | 0.94 | 9.3 |
| 45 | 0.29 | >50 |
| 46 | 0.74 | >50 |
| 47 | 0.22 | 22 |
| 48 | 12 | 3.0 |
| 49 | 44 | 4.1 |
| 50 | 50 | 3.0 |
| 51 | 2.1 | 4.2 |
| 52 | 4.5 | 21 |
| 53 | 6.0 | 20 |
| 54 | 17 | >50 |
| 55 | 6.8 | 6.3 |
| 56 | 14 | >50 |
| 57 | 5.7 | 16 |
| 58 | 5.3 | 26 |
| 59 | 11 | >50 |
| 60 | 28 | >50 |
| 61 | 33 | >50 |
| 62 | 3.8 | 9.5 |
| 63 | 12 | 2.5 |
| 64 | 6.4 | 25 |
| 65 | 6.7 | 21 |
| 66 | 18 | 6.8 |
| 67 | 17 | 5.1 |
| 68 | 17 | 11 |
| 69 | 12 | 36 |

Experimental Protocol of Adjuvant Arthritis

Adjuvant arthritis was induced by subcutaneously administering a suspension of 0.5 mg of *Mycobacterium butyricum* (Difco) in 0.05 ml of liquid paraffin to the pad of left foot of Crj/LEW male rat of 7–8 weeks age weighing 150–170 g. After administering the adjuvant, the volume of edema of both feet was daily measured by a plethysmometer. The adjuvant had been administered, and since the following day, a suspension of the test compound in 0.6% arabic gum was orally administered every day, and 17–18 days after administering the adjuvant, the volume of edema of the foot and that of foot to which no adjuvant had been administered were compared with each other. Volume of the edema in control group was defined as 100%, which value was obtained by subtracting the volume of foot of normal rat (1.2 ml) from the volume measured, and inhibitory percent obtained by using the inhibitor was defined as inhibitory rate. Using the inhibitory rate, effectiveness was determined by Student's-t assay.

TABLE 2

| Example No. | Dose: mg/kg, P.O | Inhibition % (To Nontreated Foot) |
|---|---|---|
| 1 | 10 | 43.4* |
| 2 | 10 | 52.3** |
| 69 | 10 | 24.6* |
| 23 | 10 | 66.0** |
| 25 | 10 | 66.0** |
| 29 | 10 | 33.1 |

*$P < 0.05$, **$P < 0.01$ to vehicle control

What was claimed is:

1. A compound of the formula:

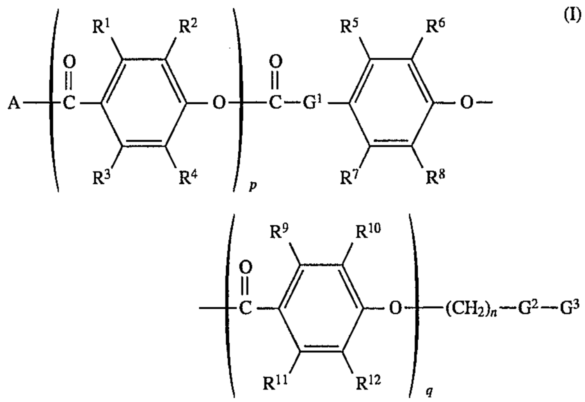

(I)

wherein A is hydroxy, amino, or lower alkylamino;

$R^1$ to $R^{12}$ are independently hydrogen, methyl, methoxy, or hydroxy, provided that only one of $R^1$ to $R^4$ may be hydrogen, only one of $R^5$ to $R^8$ may be hydrogen, and only one of $R^9$ to $R^{12}$ may be hydrogen;

$G^1$ is a single bond, or a group $-(CH_2)_xO(CH_2)_y-$ wherein x and y are independently an integer of from 0 to 5;

$G^2$ is a single bond, oxygen, sulfur, carbonyl, sulfinyl, or sulfonyl;

$G^3$ is alkyl, alkenyl, aryl, arylalkyl, arylalkenyl, bicyclo[3.1.1]heptenyl, bicyclo[2,2,1]heptyl, bornyl, chromanyl, or a group of the formula:

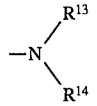

wherein $R^{13}$ and $R^{14}$ are independently hydrogen, alkyl, aryl, $-SO_2-B$ in which B is aryl or alkyl, $-CO-D$ in which D is aryl or alkoxy, or $-CH_2-E$ in which E is aryl or a heterocyclic group; or $R^{13}$ and $R^{14}$ may be taken together with the adjacent nitrogen atom to form a heterocyclic group or a group of the formula:

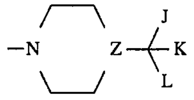

wherein Z is a carbon atom or a nitrogen atom,

J, K, and L are independently hydrogen or aryl, provided that when Z is a carbon atom, one of J, K, or L may be combined with Z to form a double bond;

p and q are independently 0, 1, or 2, provided that p and q are not simultaneously 0; and n is an integer of 1 to 8; or a pharmaceutically acceptable salt thereof.

2. The compound of claim 1 wherein $G^1$ is a single bond, p is 0, and q is 1, or a pharmaceutically acceptable salt thereof.

3. The compound of claim 2 wherein A is amino, or a pharmaceutically acceptable salt thereof.

4. The compound of claim 2 wherein A is hydroxy, or a pharmaceutically acceptable salt thereof.

5. The compound of claim 3 wherein $G^2$ is oxygen, and $G^3$ is phenyl optionally substituted by one or more substituents selected from the group consisting of halogen atom, an alkyl group, an alkoxy group, trifluoromethyl group, an alkylenedioxy group, an acyl group, carboxyl group, an alkoxycarbonyl group, carbamoyl group, hydroxymethyl group, nitrile group and benzhydryl group, or a pharmaceutically acceptable salt thereof.

6. The compound of claim 1 wherein $R^{13}$ and $R^{14}$ are taken together with the adjacent nitrogen atom to form a group of the formula:

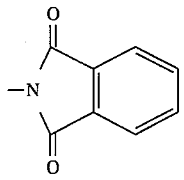

or

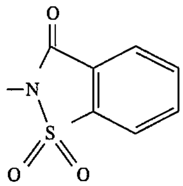

or a pharmaceutically acceptable salt thereof.

7. A pharmaceutical composition useful for inhibiting phospholipase $A_2$, which comprises the compound of claim 1 in association with a pharmaceutically acceptable carrier therefor.

8. The compound of claim 4 wherein $G^2$ is oxygen, and $G^3$ is phenyl optionally substituted by one or more substituents selected from the group consisting of halogen atom, an alkyl group, an alkoxy group, trifluoromethyl group, an alkylenedioxy group, an acyl group, carboxyl group, an alkoxycarbonyl group, carbamoyl group, hydroxymethyl group, nitrile group and benzhydryl group, or a pharmaceutically acceptable salt thereof.

* * * * *